US006897297B1

(12) United States Patent
Pepinsky et al.

(10) Patent No.: US 6,897,297 B1
(45) Date of Patent: May 24, 2005

(54) HYDROPHOBICALLY-MODIFIED PROTEIN COMPOSITIONS AND METHODS

(75) Inventors: R. Blake Pepinsky, Arlington, MA (US); Chenhui Zeng, Sudbury, MA (US); Darren P. Baker, Hingham, MA (US); Dingyi Wen, Waltham, MA (US); Kevin P. Williams, Natick, MA (US); Ellen A. Garber, Cambridge, MA (US); Kathryn L. Strauch, Bedford, MA (US); Frederick R. Taylor, Milton, MA (US); Paul H. Weinreb, Methuen, MA (US); Russell C. Petter, Stow, MA (US); Alphonse Galdes, Lexington, MA (US); Jeffrey Porter, Cambridge, MA (US)

(73) Assignees: Curis, Inc., Cambridge, MA (US); Biogen Idec Inc., Cambridge, MA (US)

( * ) Notice: Subject to any disclaimer, the term of this patent is extended or adjusted under 35 U.S.C. 154(b) by 0 days.

(21) Appl. No.: 09/579,680

(22) Filed: May 26, 2000

Related U.S. Application Data

(63) Continuation of application No. PCT/US98/25676, filed on Dec. 13, 1998.
(60) Provisional application No. 60/099,800, filed on Sep. 10, 1998, provisional application No. 60/089,685, filed on Jun. 17, 1998, provisional application No. 60/078,935, filed on Mar. 20, 1998, and provisional application No. 60/067,423, filed on Dec. 3, 1997.

(51) Int. Cl.[7] ........................ C07K 14/435; C07K 1/107
(52) U.S. Cl. ..................... 530/402; 530/350; 530/399; 530/359; 436/71; 514/12; 514/506; 514/762
(58) Field of Search ........................... 530/402, 350, 530/399, 359, 426, 427; 436/71; 514/12, 506, 762

(56) References Cited

U.S. PATENT DOCUMENTS

| 5,130,297 A | | 7/1992 | Sharma et al. | |
|---|---|---|---|---|
| 5,374,548 A | | 12/1994 | Caras | |
| 5,399,347 A | | 3/1995 | Trentham et al. | |
| 5,480,869 A | * | 1/1996 | Wei et al. | 514/16 |
| 5,516,703 A | * | 5/1996 | Caldwell et al. | 436/532 |
| 5,567,317 A | | 10/1996 | Kauvar | |
| 5,824,315 A | | 10/1998 | Nag et al. | |
| 5,877,309 A | * | 3/1999 | McKay et al. | 536/24.5 |
| 5,935,814 A | * | 8/1999 | Bergsma et al. | 435/69.1 |
| 6,069,128 A | * | 5/2000 | Naccache et al. | 514/15 |
| 6,071,532 A | * | 6/2000 | Chaikof et al. | 424/450 |

FOREIGN PATENT DOCUMENTS

| WO | WO 96/16668 | | 6/1996 |
|---|---|---|---|
| WO | WO 96/29342 | * | 9/1996 |
| WO | WO 97/40852 | | 11/1997 |
| WO | WO 98/30576 | | 7/1998 |
| WO | WO 99/28343 | | 6/1999 |

OTHER PUBLICATIONS

Lehninger, Biochemistry, second edition, Worth Publishers, 1970, p. 72.*
Arimilli, S. et al. Antigen–Specific apoptosis in immortalized T cells by soluble MHC class II–peptide complexes. *Immunology and Cell Biology* 74, 96–104 (1996).
Busconi L. & Denker, B. M. Analysis of the N–terminal binding domain of $G_o\alpha$. *Biochem. J.* 328, 23–31 (1997).
Clark, B. R. et al. Antigen–specific Deletion Cloned T Cells Using Peptide–Toxin Conjugate Complexed with Purified Class II Major Histocompatibility Complex Antigen. *J. Biol. Chem.* 269, 94–99 (1994).
Everett, K. D. E. et al. Characterization of Lipoprotein EnvA in Chlamydia psittaci 6BC. *J. Bacteriology* vol. 176, 6082–6087 (Oct. 1994).
Karin, N. et al. Reversal of Experimental Autoimmune Encephalomyelitis by a Soluble Peptide Variant of a Myelin Basic Protein Epitope: T Cell Receptor Antagonism and Reduction of Interferon Y and Tumor Necrosis Factor α Production. *J. Exp. Med.* 180, 2227–2237 (1994).
Kleuss C. & Gilman A. G.. Gs α contains an unidentified covalent modification that increases its affinity for adenyly cyclase. *PNAS* 94, 6116–6120 (Jun. 1997).
Moll, T. S. & Thompson, T. E. Semisyntheic Proteins: Model Systems for the Study of the Insertion of Hydrophobic Peptides into Preformed Lipid Bilayers. *Biochemistry* 33, 15469–15482 (1994).
Skolnick, J. & Fetrow, J. S. From genes to protein structure and function: novel applications of computational appraoches in the genomic era. *Trends in Biotechnology* 18, 34–39 (Jan. 2000).

* cited by examiner

Primary Examiner—Lorraine Spector
Assistant Examiner—Eileen B O'Hara
(74) Attorney, Agent, or Firm—Ropes & Gray LLP

(57) ABSTRACT

Hydrophobically-modified proteins and methods of making them are described. A hydrophobic moiety is attached to a surface amino acid residue of the protein. The hydrophobic moiety can be a lipid or a peptide. Alternatively, the protein can be derivatized by a wide variety of chemical reactions that append a hydrophobic structure to the protein. The preferred protein is of mammalian origin and is selected from the group consisting of Sonic, Indian, and Desert hedgehog. The hydrophobic moiety is used as a convenient tether to which may be attached a vesicle such as a cell membrane, liposome, or micelle.

51 Claims, 16 Drawing Sheets

```
         1                                                          50
Indian   CGPGRVVGSR  RRPPRK-LVP  LAYKQFSPNV  PEKTLGASGR  YEGKIARSSE
Sonic    CGPGRGFG-K  RRHPKK-LTP  LAYKQFIPNV  AEKTLGASGR  YEGKISRNSE
Desert   CGPGRGPVGR  RRYARKQLVP  LLYKQFVPGV  PERTLGASGP  AEGRVARGSE 51                                                         100
Indian   RFKELTPNYN  PDIIFKDEEN  TGADRLMTQR  CKDRLNSLAI  SVMNQWPGVK
Sonic    RFKELTPNYN  PDIIFKDEEN  TGADRLMTQR  CKDKLNALAI  SVMNQWPGVK
Desert   RFRDLVPNYN  PDIIFKDEEN  SGADRLMTER  CKERVNALAI  AVMNMWPGVR 101                                                        150
Indian   LRVTEGWDED  GHHSEESLHY  EGRAVDITTS  DRDRNKYGLL  ARLAVEAGFD
Sonic    LRVTEGWDED  GHHSEESLHY  EGRAVDITTS  DRDRSKYGML  ARLAVEAGFD
Desert   LRVTEGWDED  GHHAQDSLHY  EGRALDITTS  DRDRNKYGLL  ARLAVEAGFD 151                    176
Indian   WVYYESKAHV  HCSVKSEHSA  AAKTGG        SEQ ID NO: 1
Sonic    WVYYESKAHI  HCSVKAENSV  AAKSGG        SEQ ID NO. 2
Desert   WVYYESRNHV  HVSVKADNSL  AVRAGG        SEQ ID NO. 3
```

Gap(s), indicated by -, added to facilitate alignment

Fig. 8

1                                                                                          40
CGPGR$_{X1}$ $_{X2}$ $_{X3}$ $_{X4}$ $_{X5}$    RR$_{X6}$ $_{X7}$ $_{X8}$K$_{X9}$L$_{X10}$P   L$_{X11}$YKQF$_{X12}$P$_{X13}$V   $_{X14}$EKTLGASGR
                                                                                           80
$_{X15}$EGK$_{X16}$ $_{X17}$R$_{X18}$SE    RFK$_{X19}$L$_{X20}$PNYN    PDIIFKDEEN    $_{X21}$GADRLMT$_{X22}$R
                                                                                          120
CK$_{X23}$ $_{X24}$$_{X25}$NSLAI    $_{X26}$VMN$_{X27}$WPGVK    LRVTEGWDED    GHH$_{X28}$ $_{X29}$ $_{X30}$SLHY
                                                                                          160
EGRAVDITTS    DRDR$_{X31}$KYG$_{X32}$L    ARLAVEA

HYDROPHOBICALLY-MODIFIED PROTEIN COMPOSITIONS AND METHODS

This application is a continuation of and claims priority to PCT/US98/25676, filed Dec. 3, 1998, U.S. provisional application 60/099,800, filed Sep. 10, 1998, U.S. provisional application 60/089,685, filed Jun. 17, 1998, U.S. provisional application 60/078,935, filed Mar. 20, 1998, and U.S. provisional application 60/067,423, filed Dec. 3, 1997. The contents of each of the foregoing applications are hereby incorporated by reference in their entirety.

BACKGROUND OF THE INVENTION

It is known that certain proteins exhibit greater biological activity when attached to other moieties, either by formation of multimeric complexes, where the proteins have an opportunity to act in concert, or through other alterations in the protein's physico-chemical properties, such as the protein's absorption, biodistribution and half life. Thus, one current area of research in biotechnology involves the development of methods to modify the physico-chemical properties of proteins so that they can be administered in smaller amounts, with fewer side effects, by new routes, and with less expense.

For example, the binding affinity of any single protein (such as a ligand for its cognate receptor) may be low. However, cells normally express hundreds to thousands of copies of a particular surface receptor, and many receptor-ligand interactions take place simultaneously. When many surface molecules become involved in binding, the total effective affinity is greater than the sum of the binding affinities of the individual molecules. By contrast, when ligand proteins are removed from the cell surface and purified, or isolated by recombinant DNA techniques for use, e.g., as therapeutics, they act as monomers and lose the advantage of acting in concert with many other copies of the same protein associated closely on the surface of a cell. Thus isolated, the low affinity of a protein for its receptor may become a serious drawback to its effectiveness as a therapeutic to block a particular binding pathway, since it must compete against the high avidity cell-cell interactions. Effective treatment might require constant administration and/or high doses. Such drawbacks might be avoided, however, if a means could be found to provide multimeric forms of an isolated protein.

Similarly, it would be useful to modify other physico-chemical properties of biologically active proteins so that, for instance, a protein is induced to associate with a membrane thus localizing it at the site of administration and enhancing its ability to bind to, or otherwise interact with, a particular target. Such changes may also affect the pharmaco-distribution of the protein.

Several methods of generating coupled proteins have been developed. Many of these methods are not highly specific, i.e., they do not direct the point of coupling to any particular site on the protein. As a result, conventional coupling agents may attack functional sites or sterically block active sites, rendering the coupled proteins inactive. Furthermore, the coupled products may be oriented so that the active sites cannot act synergistically, thereby rendering the products no more effective than the monomeric protein alone.

As an additional motivation to find new methods for protein modification, proteins with an N-terminal cysteine residue are susceptible to oxidation or other chemical modifications that may compromise activity or half-life. Additionally, certain buffers commonly used in protein purification have components or impurities that can modify the N-terminal cysteine. Even when these buffers are avoided, the N-terminal cysteine is modified over time, perhaps due to chemicals in the storage vials or in the air. Consequently, formulation buffers must include a protective agent, such as dithiothreitol, to prevent cysteine modification and/or oxidation. However, protective agents have significant biological activity of their own and they may therefore complicate experiments and adversely affect the therapeutic utility of a formulation.

Accordingly, there is a need in the art to develop more specific means to obtain derivatized products or multimeric forms thereof so as to alter the properties of the protein in order to affect its stability, potency, pharmacokinetics, and pharmacodynamics.

SUMMARY OF THE INVENTION

In one aspect of the invention, we have solved the problem of finding a way to conveniently make modified forms of biologically active proteins. Methods of the invention can be used to derive multimeric forms of the proteins and/or can be used to change their physico-chemical properties. We have found that modifying a protein (i.e, adding or appending a hydrophobic moiety to an existing amino acid or substituting a hydrophobic moiety for an amino acid) so as to introduce the hydrophobic moiety onto a protein can increase the protein's biological activity and/or its stability. For example, an N-terminal cysteine can be used as a convenient "target" to attach a hydrophobic moiety (e.g., a lipid) and thereby modify biologically active proteins.

Alternatively, a hydrophobic moiety can be attached to a C-terminal residue of a biologically active protein, such as hedgehog protein, to modify the protein's activity. A hydrophobic moiety can also be appended to an internal amino acid residue to enhance the protein's activity, provided the modification does not affect the activity of the protein, e.g., the proteins ability to bind to a receptor or co-receptor, or affect the protein's 3 dimensional structure. Preferably, the hydrophobic moiety is appended to an internal amino acid residue that is on the surface of the protein when the protein is in its native form. The hydrophobic modification of the invention provides a generically useful method of creating proteins with altered physico-chemical properties as compared to non-modified forms.

This invention originated from the discovery that when we expressed full-length Sonic hedgehog protein in insect and in mammalian cells, the mature form of the protein (residues 1–174 in the mature sequence), in addition to having cholesterol at the C-terminus, is also derivatized at its N-terminal end with a fatty acid. Significantly, this form of hedgehog exhibited about a 30-fold increase in potency as compared to soluble, unmodified hedgehog in an in vitro assay.

One aspect of the invention is therefore an isolated, protein comprising an N-terminal amino acid and a C-terminal amino acid, wherein the protein is selected from the group consisting of a protein with an N-terminal cysteine that is appended with at least one hydrophobic moiety; a protein with an N-terminal amino acid that is not a cysteine appended with a hydrophobic moiety; and a protein with a hydrophobic moiety substituted for the N-terminal amino acid. The hydrophobic moiety can be a hydrophobic peptide or any lipid or any other chemical moiety that is hydrophobic.

The protein may be modified at its N-terminal amino acid and preferably the N-terminal amino acid is a cysteine or a functional derivative thereof. The protein may be modified at its C-terminal amino acid or at both the N-terminal amino acid and the C-terminal amino acid, or at at least one amino acid internal to (i.e., intermediate between) the N-terminal and C-terminal amino acids, or various combinations of these configurations. The protein can be an extracellular signaling protein and in preferred embodiments, the protein is a hedgehog protein obtainable from a vertebrate source, most preferably obtainable from a human and includes Sonic, Indian, and Desert hedgehog.

Another embodiment is an isolated, protein of the form: A-Cys-[Sp]-B-X, wherein

A is a hydrophobic moiety;

Cys is a cysteine or functional equivalent thereof;

[Sp] is an optional spacer peptide sequence;

B is a protein comprising a plurality of amino acids, including at least one optional spacer peptide sequence; and X is optionally another hydrophobic moiety linked to the protein.

The isolated protein can be an extracellular signaling protein, preferably a hedgehog protein. This protein can be modified at at least one other amino acid with at least one hydrophobic moiety. In other embodiments, the protein is in contact with a vesicle in selected from the group consisting of a cell membrane, micelle and liposome.

Another aspect of the invention is an isolated, protein having a C-terminal amino acid and an N-terminal thiaproline group, the thiaproline group formed by reacting an aldehyde with an N-terminal cysteine of the protein. A further aspect of the invention is isolated, protein having a C-terminal amino acid and an N-terminal amide group, the amide group formed by reacting a fatty acid thioester with an N-terminal cysteine of the protein. Yet another aspect of the invention is an isolated, protein having a C-terminal amino acid and an N-terminal maleimide group, the N-terminal maleimide group formed by reacting a maleimide group with the N-terminal cysteine of the protein. Yet another aspect of the invention is an isolated, protein having a C-terminal amino acid and an N-terminal acetamide group. A further aspect of the invention is an isolated, protein having a C-terminal amino acid and an N-terminal thiomorpholine group.

In these embodiments, the C-terminal amino acid of the protein can be modified with an hydrophobic moiety. The isolated protein can be an extracellular signaling protein, most preferably a hedgehog protein.

Methods of the invention include a method of generating a multivalent protein complex comprising the step of linking, in the presence of a vesicle, a hydrophobic moiety to an N-terminal cysteine of a protein, or a functional equivalent of the N-terminal cysteine. The linking step may include linking a lipid moiety which is selected from saturated and unsaturated fatty acids having between 2 and 24 carbon atoms. The protein can be an extracellular signaling protein, preferably a hedgehog protein selected from the group consisting of Sonic, Indian and Desert hedgehog.

Yet another method of the invention is a method for modifying a physico-chemical property of a protein, comprising introducing at least one hydrophobic moiety to an N-terminal cysteine of the protein or to a functional equivalent of the N-terminal cysteine. The hydrophobic moiety can be a lipid moiety selected from saturated and unsaturated fatty acids having between 2 and 24 carbon atoms. It can also be a hydrophobic protein The protein modified using this method can be an extracellular signaling protein, preferably a hedgehog protein selected from the group consisting of Sonic, Indian and Desert hedgehog. A protein complex, produced by these methods are also encompassed by the present invention.

Other extracellular signaling proteins besides hedgehog include gelsolin; an interferon, an interleukin, tumor necrosis factor, monocyte colony stimulating factor, granulocyte colony stimulating factor, granulocyte macrophage colony stimulating factor, erythropoietin, platelet derived growth factor, growth hormone and insulin.

Another method is a method for modifying a protein (such as an extracellular signaling protein) that has an N-terminal cysteine. This method comprises reacting the N-terminal cysteine with a fatty acid thioester to form an amide, wherein such modification enhances the protein's biological activity.

Yet another method is a method for modifying a protein (such as an extracellular signaling protein) having an N-terminal cysteine, which comprising reacting the N-terminal cysteine with a maleimide group, wherein such modification enhances the protein's biological activity. Other embodiments of this method involve reacting the N-terminal cysteine with either an aldehyde group, an acetamide group or a thiomorpholine group.

A further method is a method for modifying protein (such as an extracellular signaling protein) comprising appending an hydrophobic peptide to the protein. The hydrophobic moiety can be appended to an amino acid of the protein selected from the group consisting of the N-terminal amino acid, the C-terminal amino acid, an amino acid intermediate between the N-terminal amino acid and the C-terminal amino acid, and combinations of the foregoing. In one embodiment, the present invention provides hedgehog polypeptides which are modified with lipophilic moieties. In certain embodiments, the hedgehog proteins of the present invention are modified by a lipophilic moiety or moieties at one or more intenal sites of the mature, processed extracellular domain, and may or may not be also derivatized with lipophilic moieties at the N or C-terminal residues of the mature polypeptide. In other embodiments, the polypeptide is modified at the C-terminal residue with a hydrophobic moiety other than a sterol. In still other embodiments, the polypeptide is modified at the N-terminal residue with a cyclic (preferably polycyclic) lipophilic group. Various combinations of the above are also contemplated. A therapeutic method of the invention is a method for treating a neurological disorder in a patient comprising administering to the patient a hydrophobically-modified protein of the invention.

BRIEF DESCRIPTION OF THE FIGURES

FIG. 8. Alignment of N-terminal fragment of human hedgehog proteins. The 20 kDa human hedgehog proteins (Sonic "Shh", Desert "Dhh" and Indian "Ihh") are aligned with respect to their N-terminal cysteine (Cys-1 in the mature sequence). This cysteine is normally Cys-24 in the full-length Shh precursor protein due to the presence of the natural signal sequence that is removed during secretion. The actual position of the cysteine may vary slightly due to species differences.

FIG. 9. Consensus Sequence of the N-terminal fragment of human hedgehog proteins.

DETAILED DESCRIPTION OF THE INVENTION

Figure 1:
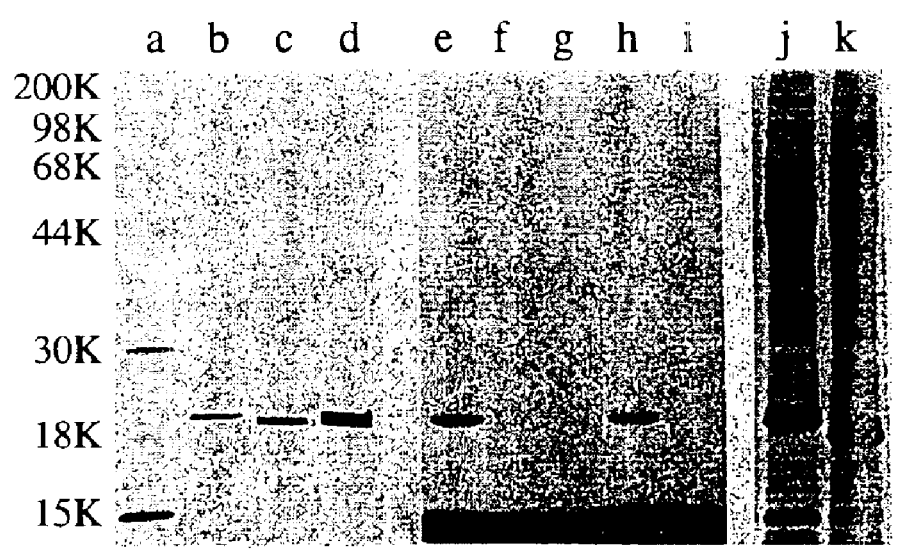
FIG. 1. Characterization of a palmitoylated form of Shh. A tethered form of human Shh was immunoaffinity purified from High Five™ insect cells and analyzed by SDS-PAGE. The protein was stained with Coomassie blue (lane a, Life Technologies, Inc. prestained high molecular weight markers; lane b, soluble Shh (0.6 µg); lane c, tethered Shh (0.6 µg); lane d, mixture of soluble plus tethered Shh (0.6 µg each)). The ability of Shh and Ihh (see lane h) to be modified with palmitic acid was assayed using a cell-free system described in Example 2. Soluble forms of hedgehog protein (3 µg/sample) were incubated for 1 h with rat liver microsomes, ATP, CoenzymeA, and $^3$H-palmitic acid, and then analyzed for palmitoylation by SDS-PAGE. The samples shown in lanes e–i were visualized by fluorography (lane e, Shh; lane f, des 1–10 Shh; lane g, Cys-1 to Ser Shh; lane h, Ihh; lane i, His-tagged Shh) and in lanes j–k by Coomassie staining (lane j, Shh; lane k des 1–10 Shh).

This invention is based, in part, on the discovery that human Sonic hedgehog, expressed as a full-length construct in either insect or in mammalian cells, has a hydrophobic palmitoyl group appended to the α-amine of the N-terminal cysteine. This is the first example, of which the inventors are aware, of an extracellular signaling protein being modified in such a manner, and, in contrast to thiol-linked palmitic acid modifications whose attachment is readily reversible, this novel N-linked palmitoyl moiety is likely to be very stable by analogy with myristic acid modification.

As a direct consequence of this initial discovery, the inventors have found that increasing the hydrophobic nature of a signaling protein can increase the protein's biological activity. In particular, the inventors have found that appending a hydrophobic moiety to a signaling protein, such as a hedgehog protein, can enhance the protein's activity. The inventors have found that the N-terminal cysteine of biologically active proteins not only provides a convenient site for appending a hydrophobic moeity, and thereby modifying the physico-chemical properties of the protein, but modifications to the N-terminal cysteine can also increase the protein's stability. Additionally, addition of a hydrophobic moiety to an internal amino acid residue on the surface of the protein structure enhances the protein's activity. We use as an example, our discovery of hydrophobic (e.g., lipids and hydrophobic amino acid) modifications of hedgehog protein.

One aspect of the present application is directed to the discovery that, in addition to those effects seen by cholesterol-addition to the C-terminus of extracellular fragments of the protein, at least certain of the biological activities of the hedgehog gene products are unexpectedly potentiated by derivativation of the protein with lipophilic moieties at other sites on the protein and/or by moieties other than cholesterol. Certain aspects of the invention are directed to preparations of hedgehog polypeptides which are modified at sites other than N-terminal or C-terminal residues of the natural processed form of the protein, and/or which are modified at such terminal residues with lipophilic moieties other than a sterol at the C-terminus or fatty acid at the N-terminus.

As described in PCT publications WO 95/18856 and WO 96/17924 (all of which are expressly incorporated by reference herein), hedgehog polypeptides in general are useful in the in vitro and in vivo repairing and/or regulating the functional performance of a wide range of cells, tissues and organs, and have therapeutic uses ragning from neuroprotection, neuroregeneration, enhancement of neural function, regulation of bone and cartilage formation and repair, regulation of spermatogenesis, regulation of lung, liver and other organs arising from the primative gut, regulation of hematopoietic function, etc. Accordingly, the methods and compositions of the present invention include the use of the derivatized hedgehog polypeptides for all such uses as hedgehog proteins have been implicated. Moreover, the subject methods can be performed on cells which are provided in culture (in vitro), or on cells in a whole animal (in vivo).

In one aspect, the present invention provides pharmaceutical preparations comprising, as an active ingredient, a hedgehog polypeptide being derivatized by one or more lipophilic moieties such as described herein.

The subject hedgehog treatments are effective on both human and animal subjects. Animal subjects to which the invention is applicable extend to both domestic animals and livestock, raised either as pets or for commercial purposes. Examples are dogs, cats, cattle, horses, sheep, hogs and goats.

The hedgehog proteins are a family of extracellular signaling proteins that regulate various aspects of embryonic development both in vertebrates and in invertebrates (for reviews see 1,2). The most well-characterized hedgehog protein is Sonic hedgehog (Shh), involved in anterior-posterior patterning, formation of an apical ectodermal ridge, hindgut mesoderm, spinal column, distal limb, rib development, and lung development, and in inducing ventral cell types in the spinal cord, hindbrain and forebrain (3–8). While the mechanism of action of hedgehog proteins is not understood fully, the most recent biochemical and genetic data suggest that the receptor for Shh is the product of the tumor suppressor gene, patched (9,10) and that other proteins; smoothened (10,11), Cubitus interruptus (12,13), and fused (14) are involved in the hedgehog signaling pathway.

Human Shh is synthesized as a 45 kDa precursor protein that is cleaved autocatalytically to yield: (1) a 20 kDa N-terminal fragment that is responsible for all known hedgehog signaling activity (SEQ ID NOS. 1–4); and (II) a 25 kDa C-terminal fragment that contains the autoprocessing activity (15–17). The N-terminal fragment consists of amino acid residues 24–197 of the full-length precursor sequence.

The N-terminal fragment remains membrane-associated through the addition of a cholesterol at its C-terminus (18,19). This cholesterol is critical for restricting the tissue localization of the hedgehog signal. The addition of the cholesterol is catalyzed by the C-terminal domain during the processing step.

All references cited in the detailed description are, unless otherwise stipulated, incorporated herein by reference.

I. Definitions

The invention will now be described with reference to the following detailed description of which the following definitions are included:

"amino acid"—a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

"protein"—any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

"N-terminal end"—refers to the first amino acid (amino acid number 1) of the mature form of a protein.

"N-terminal cysteine"—refers to the amino acid residue (number 1) as shown in SEQ ID NOS. 1–4. It also refers to any cysteine at position 1 of any other protein, or functional equivalents of this cysteine (See Section IV).

"spacer" sequence refers to a short sequence that can be as small as a single amino acid that may be inserted between an amino acid to be hydrophobically modified (such as, for example, the N-terminal cysteine or functional equivalent) and the remainder of the protein. A spacer is designed to provide separation between the-hydrophobic modification (e.g., the modified N-terminal cysteine) and the rest of the protein so as to prevent the modification from interfering with protein function and/or make it easier for the modification (e.g., the N-terminal cysteine) to link with a lipid, vesicle, or other hydrophobic moiety. Thus, if a protein is modified at its N-terminal cysteine and at an amino acid at another site, there may be two, or more, spacer sequences.

"tethered" protein—refers to a hydrophobically-modified protein according to the invention.

"multivalent protein complex"—refers to a plurality of proteins (i.e., one or more). A lipid or other hydrophobic moiety is attached to at least one of the plurality of proteins. The lipid or other hydrophobic moiety may optionally be in contact with a vesicle. If a protein lacks a lipid or other hydrophobic moiety, then that protein may be cross-linked or bind to a protein that does have a lipid or other hydrophobic moiety. Each protein may be the same or different and each lipid or other hydrophobic moiety may be the same or different.

"vesicle"—refers to any aggregate of lipophilic molecules. The vesicle may be obtained from a biologic source (e.g., a lipid bilayer such as a cell membrane or a cholic acid-derived detergent preparation) or from a non-biologic source (e.g., a non-biologic detergent vesicle as described in Section VI). The shape, type, and configuration of the vesicle is not intended to limit the scope of this invention.

"functional equivalent" of an amino acid residue (e.g., an N-terminal cysteine)—is (i) an amino acid having similar reactive properties as the amino acid residue that was replaced by the functional equivalent; (ii) an amino acid of a ligand of a polypeptide of the invention, the amino acid having similar hydrophobic (e.g., lipid) moiety binding properties as the amino acid residue that was replaced by the functional equivalent; (iii) a non-amino acid molecule having similar hydrophobic (e.g., lipid) moiety binding properties as the amino acid residue that was replaced by the functional equivalent.

"genetic fusion"—refers to a co-linear, covalent linkage of two or more proteins or fragments thereof via their individual peptide backbones, through genetic expression of a polynucleotide molecule encoding those proteins.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$-$(hh)_m$—$(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and in are preferably no greater than 5 or 10).

"mutant"—any change in the genetic material of an organism, in particular any change (i.e., deletion, substitution, addition, or alteration) in a wild type polynucleotide sequence or any change in a wild type protein.

"wild type"—the naturally-occurring polynucleotide sequence of an exon of a protein, or a portion thereof, or protein sequence, or portion thereof, respectively, as it normally exists in vivo.

"standard hybridization conditions"—salt and temperature conditions substantially equivalent to 0.5×SSC to about 5×SSC and 65° C. for both hybridization and wash. The term "standard hybridization conditions" as used herein is an operational definition and encompasses a range of hybridization conditions. See also Current Protocols in Molecular Biology, John Wiley & Sons, Inc. New York, Sections 6.3.1–6.3.6, (1989).

"expression control sequence"—a sequence of polynucleotides that controls and regulates expression of genes when operatively linked to those genes.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"expression vector"—a polynucleotide, such as a DNA plasmid or phage (among other common examples) which allows expression of at least one gene when the expression vector is introduced into a host cell. The vector may, or may not, be able to replicate in a cell.

"Isolated" (used interchangeably with "substantially pure")—when applied to nucleic acid i.e., polynucleotide sequences that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) synthesized chemically; (iii) produced recombinantly by cloning; or (iv) purified, as by cleavage and gel separation.

Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional hedgehog sequences.

"Isolated" (used interchangeably with "substantially pure")—when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature.

By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"Heterologous promoter"—as used herein is a promoter which is not naturally associated with a gene or a purified nucleic acid.

"Homologous"—as used herein is synonymous with the term "identity" and refers to the sequence similarity between two polypeptides, molecules, or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The percentage homology between two sequences is a function of the number of matching or homologous positions shared by the two sequences divided by the number of positions compared×100. For instance, if 6 of 10 of the positions in two sequences are matched or are homologous, then the two sequences are 60% homologous. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., *J. Mol. Biol.* 48: 443453 (1970), implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354–352, Nat. Biomed. Res. Foundation, Washington, D.C. (1978).

A "hedgehog protein" or "hedgehog polypeptide", as the terms are used interchangeably, of the invention is defined in terms of having at least a portion that consists of the consensus amino acid sequence of SEQ ID NO: 4. The term also means a hedgehog polypeptide, or a functional variant of a hedgehog polypeptide, or homolog of a hedgehog polypeptide, or functional variant, which has biological activity. In particular, the terms encompasses preparations of hedgehog proteins and peptidyl fragments thereof, both agonist and antagonist forms as the specific context will make clear. As used herein the term "bioactive fragment of a hedgehog protein" refers to a fragment of a full-length hedgehog polypeptide, wherein the fragment specifically agonizes or antagonizes inductive events mediated by wild-type hedgehog proteins. The hedgehog biactive fragment preferably is a soluble extracellular portion of a hedgehog protein, where solubility is with reference to physiologically compatible solutions. Exemplary bioactive fragments are described in PCT publications WO 95/18856 and WO 96/17924. In preferred embodiments, the hedgehog polypeptides of the present invention bind to the patched protein.

The term "corresponds to", when referring to a particular polypeptide or nucleic acid sequence is meant to indicate that the sequence of interest is identical or homologous to the reference sequence to which it is said to correspond.

The terms "peptide(s)", "protein(s)" and "polypeptide(s)" are used interchangeably herein. The terms "polynucleotide sequence" and "nucleotide sequence" are also used interchangeably herein. The terms "Hedgehog fragment" and "Hedgehog N-terminal fragment" are used interchangeably with "Hedgehog".

A hedgehog-molecule has "biological activity"-if it has at least one of the following properties: (i) the molecule meets the hedgehog consensus criteria as defined herein (SEQ ID NO: 4) and has the ability to bind to its receptor, patched or it encodes, upon expression, a polypeptide that has this characteristic; (ii) the molecule meets the hedgehog consensus criteria as defined herein or it encodes, upon expression, a polypeptide that has this characteristic; and (iii) it may induce alkaline phosphatase activity in C3H10T1/2 cells. Generally, any protein has "biological activity" if the protein has in vitro effects, properties, or characteristics that persons having ordinary skill in the art would recognize as being representative of, commensurate with, or reasonably predictive of, the protein's in vivo effects.

The term "hydrophobic" refers to the tendency of chemical moieties with nonpolar atoms to interact with each other rather than water or other polar atoms. Materials that are "hydrophobic" are, for the most part, insoluble in water. Natural products with hydrophobic properties include lipids, fatty acids, phospholipids, sphingolipids, acylglycerols, waxes, sterols, steroids, terpenes, prostaglandins, thromboxanes, leukotrienes, isoprenoids, retenoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms. The term includes lipophilic groups.

The term "lipophilic group", in the context of being attached to a polypeptide, refers to a group having high hydrocarbon content thereby giving the group high affinity to lipid phases. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

The phrase "internal amino acid" means any amino acid in a peptide sequence that is neither the N-terminal amino acid nor the C-terminal amino acid.

The phrase "surface amino acid" means any amino acid that is exposed to solvent when a protein is folded in its native form.

The phrase "extracellular signaling protein" means any protein that is either secreted from a cell, or is tethered to the outside of a cell, and upon binding to the receptor for that protein on a target cell triggers a response in the target cell.

An "effective amount" of, e.g., a hedgehog polypeptide, with respect to the subject methods of treatment, refers to an amount of polypeptide in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

A "patient" or "subject" to be treated by the subject method can mean either a human or non-human animal.

The "growth state" of a cell refers to the rate of proliferation of the cell and the state of differentiation of the cell.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature.

II. General Properties of Isolated Hedgehog Proteins

The polypeptide portion of the hedgehog compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

Isolated hedgehog proteins used in the methods of this invention are naturally occurring or recombinant proteins of the hedgehog family and may be obtainable from either invertebrate or from vertebrate sources (see references below). Members of the vertebrate hedgehog protein family share homology with proteins encoded by the *Drosophila* hedgehog (hh) gene (33). To date, the combined screening of mouse genomic and cDNA libraries has identified three mammalian hh counterparts referred to as Sonic hedgehog (Shh), Indian hedgehog (Ihh), and Desert hedgehog (Dhh), which also exist in other mammals, including humans, as well as in fish and in birds. Other members include Moonrat hedgehog (Mhh), as well as chicken Sonic hh and zebrafish Sonic hh.

Mouse and chicken Shh and mouse Ihh genes encode glycoproteins which undergo cleavage, yielding an amino terminal fragment of about 20 kDa (See FIG. 8) and a carboxy terminal fragment of about 25 kDa. The most preferred 20 kDa fragment has the consensus sequence SEQ ID NO: 4 and includes the amino acid sequences of SEQ ID NOS: 1–3. Various other fragments that encompass the 20 kDa moiety are considered within the presently claimed invention. Publications disclosing these sequences, as well as their chemical and physical properties, include (34–38); PCT Patent Applications WO 95/23223 (Jessell, Dodd, Roelink and Edlund), WO 95/18856 (Ingham, McMahon and Tabin) and WO 96/17924 (Beachy et al.).

Family members useful in the methods of the invention include any of the naturally-occurring native hedgehog proteins including allelic, phylogenetic counterparts or other variants thereof, whether naturally-sourced or produced chemically including muteins or mutant proteins, as well as recombinant forms and new, active members of the hedgehog family. Particularly useful hedgehog polypeptides include SEQ ID NOS: 1–4.

Isolated hedgehog polypeptides used in the method of the invention have biological activity. The polypeptides include an amino acid sequence at least 60%, 80%, 90%, 95%, 98%, or 990% homologous to an amino acid sequence from SEQ ID NOS; 1–4. The polypeptide can also include an amino acid sequence essentially the same as an amino acid sequence in SEQ ID NOS: 1–4. The polypeptide is at least 5, 10, 20, 50, 100, or 150 amino acids in length and includes at least 5, preferably at least 10, more preferably at least 20, most preferably at least 50, 100, or 150 contiguous amino acids from SEQ ID NOS: 1–4.

The preferred polypeptides of the invention include a hedgehog polypeptide sequence as well as other N-terminal and/or C-terminal amino acid sequence or it may include all or a fragment of a hedgehog amino acid sequence. The isolated hedgehog polypeptide can also be a recombinant fusion protein having a first hedgehog portion and a second polypeptide portion, e.g., a second polypeptide portion having an amino acid sequence unrelated to hedgehog. The second polypeptide portion can be, e.g., histidine tag, maltose binding protein, glutathione-S-transferase, a DNA binding domain, or a polymerase activating domain.

Polypeptides of the invention include those which arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In a preferred embodiment, isolated hedgehog is a hedgehog polypeptide with one or more of the following characteristics:

(i) it has at least 30, 40, 42, 50, 60, 70, 80, 90 or 95% sequence identity with amino acids of SEQ ID NOS: 1–4;

(ii) it has a cysteine or a functional equivalent as the N-terminal end;

(iii) it may induce alkaline phosphatase activity in C3H10T1/2 cells;

(iv) it has an overall sequence identity of at least 50%, preferably at least 60%, more preferably at least 70, 80, 90, or 95%, with a polypeptide of SEQ ID NO; 1–4

(v) it can be isolated from natural sources such as mammalian cells;

(vi) it can bind or interact with patched; and (vii) it is hydrophobically-modified (i.e., it has at least one hydrophobic moiety attached to the polypeptide).

III. Other Proteins

Since techniques exist for engineering a cysteine residue (or its functional equivalent) into a polypeptide's primary sequence, virtually any protein can be converted into a hydrophobically-modified form using the methods described herein.

Viral receptors, cell receptors, and cell ligands are useful because they bind typically to cells or tissues exhibiting many copies of the receptor. Useful viral-cell protein receptors that can be complexed together using the methods of this invention include ICAM1, a rhinovirus receptor; CD2, the Epstein-Barr virus receptor; and CD4, the receptor for human immunodeficiency virus (HIV). Other proteins include members of the cell adhesion molecule family, such as ELAM-1 and VCAM-1 and VCAM-1b and their lymphocyte counterparts (ligands); the lymphocyte associated antigens LFA1, LFA2 (CD2) and LFA3 (CD58), CD59 (a second ligand of CD2), members of the CD11/CD18 family and very late antigens such as VLA4 and their ligands.

Immunogens from a variety of pathogens (e.g., from bacterial, fungal, viral, and other eukaryotic parasites) may also be used as polypeptides in the methods of the invention. Bacterial immunogens include, but are not limited to, bacterial sources responsible for bacterial pneumonia and *pneumocystis* pneumnonia. Parasitic sources include the *Plasmodium* malaria parasite. Viral sources include poxvirus (e.g., cowpox, herpes simplex, cytomegalovirus); adenoviruses; papovaviruses (e.g., papillomavirus); parvoviruses (e.g., adeno-associated virus); retroviruses (e.g., HTLV 1, HTLV II, HIV I and HIV II) and others. Immunoglobulins, or fragments thereof, may also be polypeptides that can be modified according to the invention. One can generate monoclonal Fab fragments recognizing specific antigens using conventional methods (49) and use the individual Fab domains as functional moieties in multimeric constructs according to this invention. Other useful proteins include, gelsolin (50); cytokines, including the various interferons (interferon-$\alpha$, interferon-$\beta$, and interferon-$\gamma$); the various interleukins (e.g., IL-1, -2, -3, 4, and the like); the tumor necrosis factors-$\alpha$ and -$\beta$; monocyte colony stimulating factor (M-CSF), granulocyte colony stimulating factor (G-CSF), granulocyte macrophage colony stimulating factor (GM-CSF), erythropoietin, platelet-derived growth factor (PDGF), and human and animal hormones, including growth hormone and insulin.

Generally, the structure of the modified proteins of this invention has the general formula: A-Cys-[Sp]-B-[Sp]-X, where A is a hydrophobic moiety; Cys is a cysteine or a functional equivalent thereof; [Sp] is an optional spacer peptide sequence; B is a protein (which optionally may have another spacer peptide sequence as shown); and X is a hydrophobic moiety linked (optionally by way of the spacer peptide) to the a C-terminal end of the protein or another surface site of the protein, wherein the derivatized protein includes at least one of A or X. If X is cholesterol, then B may, or may not be, a hedgehog protein. As discussed above, the purpose of the spacer is to provide separation between the hydrophobic moiety and the rest of the protein so as to make it easier for the hydrophobic moiety (e.g., a modified N-terminal cysteine) to link with another moiety which may be a lipid or a vesicle. The spacer is also intended to make it more difficult for the modification to interfere with protein function. A spacer may be as small as a single amino acid in length. Generally, prolines and glycines are preferred. A particularly preferred spacer sequence is derived from Sonic hedgehog and consists of the amino acid sequence: G-P-G-R.

IV. Production of Recombinant Polypeptides

The isolated polypeptides described herein can be produced by any suitable method known in the art. Such methods range from direct protein synthetic methods to constructing a DNA sequence encoding isolated polypeptide sequences and expressing those sequences in a suitable transformed host.

In one embodiment of a recombinant method, a DNA sequence is constructed by isolating or synthesizing a DNA sequence encoding a wild type protein of interest. Optionally, the sequence may be mutagenized by site-specific mutagenesis to provide functional analogs thereof. See, e.g., (40) and U.S. Pat. No. 4,588,585. Another method of constructing a DNA sequence encoding a polypeptide of interest would be by chemical synthesis using an oligonucleotide synthesizer. Such oligonucleotides may be preferably designed based on the amino acid sequence of the desired polypeptide, and preferably selecting those codons that are favored in the host cell in which the recombinant polypeptide of interest will be produced.

Standard methods may be applied to synthesize an isolated polynucleotide sequence encoding a isolated polypeptide of interest. For example, a complete amino acid sequence may be used to construct a back-translated gene. See Maniatis et al., supra. Further, a DNA oligomer containing a nucleotide sequence coding for the particular isolated polypeptide may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site-directed mutagenesis, or by another method), the mutant DNA sequences encoding a particular isolated polypeptide of interest will be inserted into an expression vector and operatively linked to an expression control sequence appropriate for expression of the protein in a desired host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR1, pBR322, pMB9 and their derivatives, wider host range plasmids, such as M13 and filamentous single-stranded DNA phages. Preferred *E. coli* vectors include pL vectors containing the lambda phage pL promoter (U.S. Pat. No. 4,874,702), pET vectors containing the T7 polymerase promoter (Studier et al., Methods in Enzymology 185: 60–89, 1990 1) and the pSP72 vector (Kaelin et al., supra). Useful expression vectors for yeast cells, for example, include the 2 T and centromere plasmids.

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example pL, the control regions of fd coat protein, the promoter for 3-phosphoglycerate kinase or other glycolytic enzymes, the promoters of acid phosphatase, e.g., Pho5, the promoters of the yeast $\alpha$-mating system and other sequences known to control the expression of genes of prokaryotic or eukaryotic cells and their viruses, and various combinations thereof.

Any suitable host may be used to produce in quantity the isolated hedgehog polypeptides described herein, including bacteria, fungi (including yeasts), plants, insects, mammals, or other appropriate animal cells or cell lines, as well as transgenic animals or plants. More particularly, these hosts may include well known eukaryotic and prokaryotic hosts, such as strains of *E. coli, Pseudomonas, Bacillus, Streptomyces*, fungi, yeast (e.g., *Hansenula*), insect cells such as *Spodoptera frugiperda* (SF9), and High Five™ (see Example 1), animal cells such as Chinese hamster ovary (CHO), mouse cells such as NS/O cells, African green monkey cells COS1, COS 7, BSC 1, BSC 40, and BMT 10, and human cells, as well as plant cells.

It should be understood that not all vectors and expression control sequences will function equally well to express a given isolated polypeptide. Neither will all hosts function equally well with the same expression system. However, one of skill in the art may make a selection among these vectors, expression control systems and hosts without undue experimentation. For example, to produce isolated polypeptide of interest in large-scale animal culture, the copy number of the expression vector must be controlled. Amplifiable vectors are well known in the art. See, for example, (41) and U.S. Pat. Nos. 4,470,461 and 5,122,464.

Such operative linking of a DNA sequence to an expression control sequence includes the provision of a translation start signal in the correct reading frame upstream of the DNA sequence. If the particular DNA sequence being expressed does not begin with a methionine, the start signal will result in an additional amino acid (methionine) eing located at the N-terminus of the product. If a hydrophobic moiety is to be linked to the N-terminal methionyl-containing protein, the protein may be employed directly in the compositions of the invention. Nevertheless, since the preferred N-terminal end of the protein is to consist of a cysteine (or functional equivalent) the methionine must be removed before use. Methods are available in the art to remove such N-terminal methionines from polypeptides expressed with them. For example, certain hosts and fermentation conditions permit removal of substantially all of the N-terminal methionine in vivo. Other hosts require in vitro removal of the N-terminal methionine. Such in vitro and in vivo methods are well known in the art.

The proteins produced by a transformed host can be purified according to any suitable method. Such standard methods include chromatography (e.g., ion exchange, affinity, and sizing column chromatography), centrifugation, differential solubility, or by any other standard technique for protein purification. For immunoaffinity chromatography (See Example 1), a protein such as Sonic hedgehog may be isolated by binding it to an affinity column comprising of antibodies that were raised against Sonic hedgehog, or a related protein and were affixed to a stationary support. Alternatively, affinity tags such as hexahistidine, maltose binding domain, influenza coat sequence, and glutathione-S-transferase can be attached to the protein to allow easy purification by passage over an appropriate affinity column. Isolated proteins can also be characterized physically using such techniques as proteolysis, nuclear magnetic resonance, and X-ray crystallography.

A. Production of Fragments and Analogs

Fragments of an isolated protein (e.g., fragments of SEQ ID NOS: 1–4) can also be produced efficiently by recombinant methods, by proteolytic digestion, or by chemical synthesis using methods known to those of skill in the art. In recombinant methods, internal or terminal fragments of a polypeptide can be generated by removing one or more nucleotides from one end (for a terminal fragment) or both ends (for an internal fragment) of a DNA sequence which encodes for the isolated hedgehog polypeptide. Expression of the mutagenized DNA produces polypeptide fragments. Digestion with "end nibbling" endonucleases can also generate DNAs which encode an array of fragments. DNAs which encode fragments of a protein can also be generated by random shearing, restriction digestion, or a combination or both. Protein fragments can be generated directly from intact proteins. Peptides can be cleaved specifically by proteolytic enzymes, including, but not limited to plasmin, thrombin, trypsin, chymotrypsin, or pepsin. Each of these enzymes is specific for the type of peptide bond it attacks.

Trypsin catalyzes the hydrolysis of peptide bonds in which the carbonyl group is from a basic amino acid, usually arginine or lysine. Pepsin and chymotrypsin catalyse the hydrolysis of peptide bonds from aromatic amino acids, such as tryptophan, tyrosine, and phenylalanine. Alternative sets of cleaved protein fragments are generated by preventing cleavage at a site which is suceptible to a proteolytic enzyme. For instance, reaction of the $\epsilon$-amino acid group of lysine with ethyltrifluorothioacetate in mildly basic solution yields blocked amino acid residues whose adjacent peptide bond is no longer susceptible to hydrolysis by trypsin. Proteins can be modified to create peptide linkages that are susceptible to proteolytic enzymes. For instance, alkylation of cysteine residues with P-haloethylamines yields peptide linkages that are hydrolyzed by trypsin (51). In addition, chemical reagents that cleave peptide chains at specific residues can be used. For example, cyanogen bromide cleaves peptides at methionine residues (52). Thus, by treating proteins with various combinations of modifiers, proteolytic enzymes and/or chemical reagents, the proteins may be divided into fragments of a desired length with no overlap of the fragments, or divided into overlapping fragments of a desired length.

Fragments can also be synthesized chemically using techniques known in the art such as the Merrifield solid phase F moc or t-Boc chemistry. Merrifield, Recent Progress in Hormone Research 23: 451 (1967).

Examples of prior art methods which allow production and testing of fragments and analogs are discussed below. These, or analogous methods may be used to make and screen fragments and analogs of an isolated polypeptide (e.g., hedgehog) which can be shown to have biological activity. An exemplary method to test whether fragments and analogs of hedgehog have biological activity is found in Example 3.

B. Production of Altered DNA and Peptide Sequences: Random Methods

Amino acid sequence variants of a protein (such as variants of SEQ ID NOS: 1–4) can be prepared by random mutagenesis of DNA which encodes the protein or a particular portion thereof. Useful methods include PCR mutagenesis and saturation mutagenesis. A library of random amino acid sequence variants can also be generated by the synthesis of a set of degenerate oligonucleotide sequences. Methods of generating amino acid sequence variants of a given protein using altered DNA and peptides are well-known in the art. The following examples of such methods are not intended to limit the scope of the present invention, but merely serve to illustrate representative techniques. Persons having ordinary skill in the art will recognize that other methods are also useful in this regard.

PCR Mutagenesis: Briefly, Taq polymerase (or another polymerase) is used to introduce random mutations into a cloned fragment of DNA (42). PCR conditions are chosen so that the fidelity of DNA synthesis is reduced by Taq DNA polymers using, for instance, a dGTP/dATP ratio of five and adding $Mn^{2+}$ to the PCR reaction. The pool of amplified DNA fragments is inserted into appropriate cloning vectors to provide random mutant libraries.

Saturation Mutagenesis: One method is described generally in (43). Briefly, the technique includes generation of mutations by chemical treatment or irradiation of single stranded DNA in vitro, and synthesis of a cDNA strand. The mutation frequency is modulated by the severity of the treatment and essentially all possible base substitutions can be obtained.

Degenerate Oligonucleotide Mutagenesis: A library of homologous peptides can be generated from a set of degenerate oligonucleotide sequences. Chemical synthesis of degenerate sequences can by performed in an automatic DNA synthesizer, and the synthetic genes are then ligated into an appropriate expression vector. See for example (44, 45) and Itakura et al., Recombinant DNA, Proc. 3rd Cleveland Symposium on Macromolecules, pp. 273–289 (A. G. Walton, ed.), Elsevier, Amsterdam, 1981.

C. Production of Altered DNA and Peptide Sequences: Directed Methods

Non-random, or directed, mutagenesis provides specific sequences or mutations in specific portions of a polynucleotide sequence that encodes an isolated polypeptide, to provide variants which include deletions, insertions, or substitutions of residues of the known amino acid sequence of the isolated polypeptide. The mutation sites may be modified individually or in series, for instance by: (1) substituting first with conserved amino acids and then with more radical choices depending on the results achieved; (2) deleting the target residue; or (3) inserting residues of the same or a different class adjacent to the located site, or combinations of options 1–3.

Clearly, such site-directed methods are one way in which an N-terminal cysteine (or a functional equivalent) can be introduced into a given polypeptide sequence to provide the attachment site for a hydrophobic moiety.

Alanine scanning Mutagenesis: This method locates those residues or regions of a desired protein that are preferred locations for mutagenesis (46). In alanine screening, a residue or group of target residues are selected and replaced by alanine. This replacement can affect the interaction of the amino acid with neighboring amino acids and/or with the surrounding aqueous or membrane environment. Those having functional sensitivity to the substitutions are then refined by introducing further or other variants at, or for, the sites of substitution.

Oligonucleotide-Mediated Mutagenesis: One version of this method may be used to prepare substitution, deletion, and insertion variants of DNA (47). Briefly, the desired DNA is altered by hybridizing an oligonucleotide primer encoding a DNA mutation to a DNA template which typically is the single stranded form of a plasmid or phage containing the unaltered or wild type DNA sequence template of the desired protein (e.g., the Hedgehog protein). After hybridization, a DNA polymerase is used to make the second and complementary strand of DNA of the template that will incorporate the oligonucleotide primer, and will code for the selected alteration in the desired DNA sequence. Generally, oligonucleotides of at least 25 nucleotides in length are used. An optimal oligonucleotide will have 12 to 15 nucleotides that are completely complementary to the template on either side of the mutation. This ensures that the oligonucleotide will hybridize properly to the single-stranded DNA template molecule.

Cassette Mutagenesis: This method (48) requires a plasmid or other vector that contains the protein subunit DNA to be mutated. The codon(s) in the protein subunit DNA are identified and there is inserted a unique restriction endonuclease site on each side of the identified mutation site(s), using the above-described oligonucleotide-directed mutagenesis method. The plasmid is then cut at these sites to linearize it. A double-stranded oligonucleotide encoding the sequence of the DNA between the restriction sites but containing the desired mutation(s) is synthesized using standard procedures. The two strands are synthesized separately and then hybridized together using standard methods. This double-stranded oligonucleotide is the "cassette" and it has 3' and 5' ends that are compatible with the ends of the linearized plasmid so that it can be directly ligated therein. The plasmid now contains the mutated desired protein subunit DNA sequence.

Combinatorial Mutagenesis: In one version of this method (Ladner et al., WO 88/06630), the amino acid sequences for a group of homologs or other related proteins are aligned, preferably to promote the highest homology possible. All of the amino acids which appear at a given position of the aligned sequences can be selected to create a degenerate set of combinatorial sequences. The variegated library is generated by combinatorial mutagenesis at the nucleic acid level, and is encoded by a variegated gene library. For instance, a mixture of synthetic oligonucleotides can be ligated enzymically into the gene sequence such that the degenerate set of potential sequences are expressible as individual peptides, or alternatively, as a set of proteins containing the entire set of degenerate sequences.

D. Other Variants of Isolated Polypeptides

Included in the invention are isolated molecules that are: allelic variants, natural mutants, induced mutants, and proteins encoded by DNA that hybridizes under high or low stringency conditions to a nucleic acid which encodes a polypeptide such as the N-terminal fragment of Sonic hedgehog (SEQ ID NO: 1) and polypeptides bound specifically by antisera to hedgehog peptides, especially by antisera to an active site or binding site of hedgehog. All variants described herein are expected to: (i) retain the biological function of the original protein and (ii) retain the ability to link to a hydrophobic moiety (e.g, a lipid).

The methods of the invention also feature uses of fragments, preferably biologically active fragments, or analogs of an isolated peptide such as hedgehog. Specifically, a biologically active fragment or analog is one having any in vivo or in vitro activity which is characteristic of the peptide shown in SEQ ID NOS: 1–4 or of other naturally occurring isolated hedgehog. Most preferably, the hydrophobically-modified fragment or analog has at least 10%, preferably 40% or greater, or most preferably at least 90% of the activity of Sonic hedgehog (See Example 3) in any in vivo or in vitro assay.

Analogs can differ from naturally occurring isolated protein in amino acid sequence or in ways that do not involve sequence, or both. The most preferred polypeptides of the invention have preferred non-sequence modifications that include in vivo or in vitro chemical derivatization (e.g., of their N-terminal end), as well as possible changes in acetylation, methylation, phosphorylation, amidation, carboxylation, or glycosylation.

Other analogs include a protein such as Sonic hedgehog or its biologically active fragments whose sequences differ from the wild type consensus sequence (e.g., SEQ ID NO: 4) by one or more conservative amino acid substitutions or by one or more non conservative amino acid substitutions, or by deletions or insertions which do not abolish the isolated protein's biological activity. Conservative substitutions typically include the substitution of one amino acid for another with similar characteristics such as substitutions within the following groups: valine, alanine and glycine; leucine and isoleucine; aspartic acid and glutamic acid; asparagine and glutamine; serine and threonine; lysine and arginine; and phenylalanine and tyrosine. The non-polar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Other conservative substitutions can be readily known by workers of ordinary skill. For example, for the amino acid alanine, a conservative substitution can be taken from any one of D-alanine, glycine, beta-alanine, L-cysteine, and D-cysteine. For lysine, a replacement can be any one of D-lysine, arginine, D-arginine, homo-arginine, methionine, D-methionine, ornithine, or D-ornithine.

Generally, substitutions that may be expected to induce changes in the functional properties of isolated polypeptides are those in which: (i) a polar residue, e.g., serine or threonine, is substituted for (or by) a hydrophobic residue, e.g., leucine, isoleucine, phenylalanine, or alanine; (ii) a cysteine residue is substituted for (or by) any other residue (See Example 10); (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine.

Other analogs used within the methods of the invention are those with modifications which increase peptide stability. Such analogs may contain, for example, one or more non-peptide bonds (which replace the peptide bonds) in the peptide sequence. Also included are: analogs that include residues other than naturally occurring L-amino acids, such as D-amino acids or non-naturally occurring or synthetic amino acids such as beta or gamma amino acids and cyclic analogs. Incorporation of D- instead of L-amino acids into the isolated hedgehog polypeptide may increase its resistance to proteases. See, U.S. Pat. No. 5,219,990 supra.

The term "fragment", as applied to an isolated hedgehog analog, can be as small as a single amino acid provided that it retains biological activity. It may be at least about 20 residues, more typically at least about 40 residues, preferably at least about 60 residues in length. Fragments can be generated by methods known to those skilled in the art. The ability of a candidate fragment to exhibit isolated hedgehog biological activity can be also assessed by methods known to those skilled in the art as described herein.

V. Making Hydrophobic Derivatives

The inventors have discovered that increasing the overall hydrophobic nature of a signaling protein, such as a hedgehog protein, increases the biological activity of the protein. The potency of a signaling protein such as hedgehog can be increased by: (a) chemically modifying, such as by adding a hydrophobic moiety to, the sulfhydryl and/or to the o-amine of the N-terminal cysteine (Examples 8 and 9); (b) replacing the N-terminal cysteine with a hydrophobic amino acid (Example 10); or (c) replacing the N-terminal cysteine with a different amino acid and then chemically modifying the substituted residue so as to add a hydrophobic moiety at the site of the substitution.

Additionally, modification of a protein such as hedgehog protein at an internal residue on the surface of the protein with a hydrophobic moiety by: (a) replacing the internal residue with a hydrophobic amino acid; or (b) replacing the internal residue with a different amino acid and then chemically modifying the substituted residue so as to add a hydrophobic moiety at the site of the substitution (See Example 10), will retain or enhance the biological activity of the protein.

Additionally, modification of a protein such as a hedgehog protein at the C-terminus with a hydrophobic moiety by: (a) replacing the C-terminal residue with a hydrophobic amino acid; or (b) replacing the C-terminal residue with a different amino acid and then chemically modifying the substituted residue so as to add a hydrophobic moiety at the site of the substitution, will retain or enhance the biological activity of the protein.

There are a wide range of lipophilic moieties with which hedgehog polypeptides can be derivatived. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Particularly useful as lipophilic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1–C18)-alkyl phosphate diesters, —O—CH2—CH(OH)—O—(C12–C18)-alkyl, and in particular conjugates with pyrene derivatives. The lipophilic moiety can be a lipophilic dye suitable for use in the invention include, but are not limited to, diphenylhexatriene, Nile Red, N-phenyl-1-naphthyl amine, Prodan, Laurodan, Pyrene, Perylene, rhodamine, rhodamine B, tetramethylrhodamine, Texas Red, sulforhodamine, 1,1'-didodecyl-3,3,3',3'-tetramethylindocarbocyanine perchlorate, octadecyl rhodamine B and the BODIPY dyes available from Molecular Probes Inc.

Other exemplary lipophilic moietites include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(−)-myrtentaneacetyl, 2-norbornaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

Structures of exemplary hydrophobic modifications are shown in FIG. 12. If an appropriate amino acid is not available at a specific position, site-directed mutagenesis can be used to place a reactive amino acid at that site. Reactive amino acids include cysteine, lysine, histidine, aspartic acid, glutamic acid, serine, threonine, tyrosine, arginine, methionine, and tryptophan. Mutagenesis could be used to place the reactive amino acid at the N- or C-terminus or at an internal position.

For example, we have discovered that it is possible to chemically modify an N-terminal cysteine of a biologically active protein, such as a hedgehog protein, or eliminate the N-terminal cysteine altogether and still retain the protein's biological activity, provided that the modified or substituted chemical moiety is hydrophobic. The inventors have found that enhancement of hedgehog's biological activity roughly correlates with the hydrophobicity of the modification. In addition to enhancing the protein's activity, modifying or replacing the N-terminal cysteine eliminates unwanted cross reactions and/or modifications of the cysteine that can occur during production, purification, formulation, and storage of the protein. The thiol of an N-terminal cysteine is very reactive due to its proximity to the α-amine which lowers the pKa of the cysteine and increases proton dissociation and formation of the reactive thiolate ion at neutral or acid pH.

We have demonstrated that replacement of the N-terminal cysteine of hedgehog with a hydrophobic amino acid results in a protein with increased potency in a cell-based signaling assay. By replacing the cysteine, this approach eliminates the problem of suppressing other unwanted modifications of the cysteine that can occur during the production, purification, formulation, and storage of the protein. The generality of this approach is supported by our finding that three different hydrophobic amino acids, phenylalanine, isoleucine, and methionine, each give a more active form of hedgehog. Therefore, replacement of the cysteine with any other hydrophobic amino acid should result in an active protein. Furthermore, since we have found a correlation between the hydrophobicity of an amino acid or chemical modification and the potency of the corresponding modified protein in the C3H10T1/2 assay (e.g. Phe>Met, long chain length fatty acids>short chain length), it could be envisioned that adding more than one hydrophobic amino acid to the hedgehog sequence would increase the potency of the protein beyond that achieved with a single amino acid addition. Indeed, addition of two consecutive isoleucine residues to the N-terminus of human Sonic hedgehog results in an increase in potency in the C3H10T1/2 assay as compared to the mutant with only a single isoleucine added (See Example 10). Thus, adding hydrophobic amino acids at the N- or C-terminus of a hedgehog protein, in a surface loop, or some combination of positions would be expected to give a more active form of the protein. The substituted amino acid need not be one of the 20 common amino acids. Methods have been reported for substituting unnatural amino acids at specific sites in proteins (78, 79) and this would be advantageous if the amino acid was more hydrophobic in character, resistant to proteolytic attack, or could be used to further direct the hedgehog protein to a particular site in vivo that would make its activity more potent or specific. Unnatural amino acids can be incorporated at specific sites in proteins during in vitro translation, and progress is being reported in creating in vivo systems that will allow larger scale production of such modified proteins.

It is unexpected that a protein, such as an hedgehog protein, modified according to the invention, would retain its biological activity. First, the N-terminal cysteine is conserved in all known hedgehog protein sequences including fish, frog, insect, bird, and mammals. Therefore, it is reasonable to expect that the free sulfhydryl of the N-terminal cysteine is important to the protein's structure or activity. Second, hedgehog proteins lacking an N-terminal cysteine, due to proteolytic cleavage or mutation to hydrophilic amino acids (e.g., aspartic acid or histidine) are inactive in a the cell-based C3H10T1/2 assay, such as that described in Example 3.

There are many modifications of the N-terminal cysteine which protect the thiol and append a hydrophobic moiety. These modifications are discussed in more detail below. One of skill in the art is capable of determining which modification is most appropriate for a particular therapeutic use. Factors affecting such a determination include cost and ease of production, purification and formulation, solubility, stability, potency, pharmacodynamics and kinetics, safety, immunogenicity, and tissue targeting.

A. Chemical Modifications of Primary Amino Acid Sequence

The chemical modification of the N-terminal cysteine to protect the thiol, with concomitant activation by a hydrophobic moiety, can be carried out in numerous ways by someone skilled in the art The sulfhydryl moiety, with the thiolate ion as the active species, is the most reactive functional group in a protein. There are many reagents that react faster with the thiol than any other groups. See *Chemistry of Protein Conjugation and Cross-Linking* (S. S. Wong, CRC Press, Boca Raton, Fla., 1991). The thiol of an N-terminal cysteine, such as found in all hedgehog proteins, would be expected to be more reactive than internal cysteines within the sequence. This is because the close proximity to the α-amine will lower the pKa of the thiol resulting in a greater degree of proton dissociation to the reactive thiolate ion at neutral or acid pH. In addition, the cysteine at the N-terminus of the structure is more likely to be exposed than the other two cysteines in the hedgehog sequence that are found buried in the protein structure. We have shown that the N-terminal cysteine is the only amino acid modified after a 1 h reaction with N-ethylmaleimide at pH 5.5 (See Example 9), and after a 18 h reaction with N-isopropyliodoacetamide at pH 7.0 (See Example 9). Other examples of such methods would be reaction with other α-haloacetyl compounds, organomercurials, disulfide reagents, and other N-substituted maleimides. Numerous hydrophobic derivatives of these active species are available commercially (e.g., ethyl iodoacetate (Aldrich, Milwaukee Wis.), phenyl disulfide (Aldrich), and N-pyrenemaleimide (Molecular Probes, Eugene Oreg.)) or could be synthesized readily (e.g., N-alkyliodoacetamides (84), N-alkylmaleimides (85), and organomercurials (86). We have shown that the N-terminal cysteine of human Sonic hedgehog can be specifically modified with N-isopropyliodoacetamide and that the hydrophobically-modified protein is 2-fold more potent in the C3H10T1/2 assay than the unmodified protein (See Example 9). It is expected that modification of Shh with a long-chain alkyl iodoacetamide derivative will result in a modified protein with even greater enhancement of potency. Such N-alkyliodoacetamides can be synthesized readily by ones skilled in the art, using commercially available starting materials.

Another aspect to the reactivity of an N-terminal cysteine is that it can take part in reaction chemistries unique to its 1,2-aminothiol configuration. One example is the reaction with thioester groups to form an N-terminal amide group via a rapid S to N shift of the thioester. This reaction chemistry can couple together synthetic peptides and can be used to add single or multiple, natural or unnatural, amino acids or other hydrophobic groups via the appropriately activated peptide. Another example, demonstrated herein, is the reaction with aldehydes to form the thiazolidine adduct. Numerous hydrophobic derivatives of thiol esters (e.g., $C_2$–$C_{24}$ saturated and unsaturated fatty acyl Coenzyme A esters (Sigma Chemical Co., St. Louis Mo.)), aldehydes (e.g., butyraldehyde, n-decyl aldehyde, and n-myristyl aldehyde (Aldrich)), and ketones (e.g., 2-, 3-, and 4-decanone (Aldrich)) are available commercially or could be synthesized readily (87, 88). In a similar manner, thiomorpholine derivatives exemplified by the 1-bromo-2-butanone chemistry described in Example 9 could be prepared from a variety of α-haloketone starting materials (88). Because of the ease of finding alternative routes to modifying the thiol of the N-terminal cysteine, or any cysteine in a protein, we do not wish to be bound by the specific examples demonstrated here.

The α-amine of a protein can be modified preferentially relative to other amines in a protein because its lower pKa results in higher amounts of the reactive unprotonated form at neutral or acidic pH. We have shown that modification of the N-terminal amine with a long chain fatty amide group, while maintaining a free cysteine thiol group, activates the hedgehog protein by as much as two orders of magnitude (See Example 8). Therefore chemistries that can be directed to react preferentially with the N-terminal amine would be expected to be of use in increasing the potency of the hedgehog proteins. Aryl halides, aldehydes and ketones, acid anhydrides, isocyanates, isothiocyanates, imidoesters, acid halides, N-hydroxysuccinimidyl (e.g., sulfo-NHS-acetate), nitrophenyl esters, acylimidazoles, and other activated esters are among those known to react with amine functions.

By replacing the N-terminal cysteine of hedgehog with certain other amino acids, other chemical methods can be used to add a hydrophobic moiety to the N-terminus. One example is to place a serine or threonine at the N-terminus, oxidize this amino acid to form an aldehyde, and then conjugate the protein with a chemical moiety containing a 1,2 aminothiol structure (e.g., a cysteine). A second example would be to place a histidine at the N-terminus to couple to a C-terminal thiocarboxylic acid.

Chemical Modification of Other Amino Acids.

There are specific chemical methods for the modification of many other amino acids. Therefore another route for synthesizing a more active-form of hedgehog would be to chemically attach a hydrophobic moiety to an amino acid in hedgehog other than to the N-terminal cysteine. If an appropriate amino acid is not available at the desired position, site-directed mutagenesis could be used to place the reactive amino acid at that site in the hedgehog structure, whether at the N- or C-terminus or at another position. Reactive amino acids would include cysteine, lysine, histidine, aspartic acid, glutamic acid, serine, threonine, tyrosine, arginine, methionine, and tryptophan. Thus the goal of creating a more hydrophobic form of hedgehog could be attained by many chemical means and we do not wish to be restricted by a particular chemistry or site of modification since our results support the generality of this approach.

The hedgehog polypeptide can be linked to the hydrophobic moiety in a number of ways including by chemical coupling means, or by genetic engineering.

To illustrate, there are a large number of chemical cross-linking agents that are known to those skilled in the art. For the present invention, the preferred cross-linking agents are heterobifunctional cross-linkers, which can be used to link the hedgehog polypeptide and hydrophobic moiety in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include: succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate 2 HCl (DMP) are examples of useful homobifunctional cross-linking agents, and bis-[β-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a recent review of protein coupling techniques, see Means et al. (1990) *Bioconjugate Chemistry* 1:2–12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-protein conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

The reaction buffer should be free of extraneous amines and sulfhydryls. The pH of the reaction buffer should be 7.0–7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the lipophilic group chosen for reaction with maleimides, activated halogens, or pyridyl disulfides must contain a free sulfhydryl. Alternatively, a primary amine may be modified with to add a sulfhydryl.

In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5–7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing lipophilic group under the appropriate buffer conditions. The conjugates can be isolated from the reaction mixture by methods such as gel filtration or by dialysis.

Exemplary activated lipophilic moieties for conjugation include: N-(1-pyrene)maleimide; 2,5-dimethoxystilbene-4'-maleimide, eosin-5-maleimide; fluorescein-5-maleimide; N-(4-(6-dimethylamino-2-benzofuranyl)phenyl)maleimide; benzophenone-4-maleimide; 4-dimethylaminophenylazophenyl-4'-maleimide (DABMI), tetramethylrhodamine-5-maleimide, tetramethylrhodamine-6-maleimide, Rhodamine Red™ C2 maleimide, N-(5-aminopentyl)maleimide, trifluoroacetic acid salt, N-(2-aminoethyl)maleimide, trifluoroacetic acid salt, Oregon Green™ 488 maleimide, N-(2-((2-((4-azido-2,3,5,6-tetrafluoro)benzoyl)amino)ethyl)dithio)ethyl)maleimide (TFPAM-SS1), 2-(1-(3-dimethylaminopropyl)-indol-3-yl)-3-indol-3-yl) maleimide (bisindolylmaleimide; GF 109203X), BODIPY® FL N-(2-aminoethyl)maleimide, N-(7-dimethylamino-4-methylcoumarin-3-yl)maleimide (DACM), Alexa™ 488 C5 maleimide, Alexa™ 594 C5 maleimide, sodium salt N-(1-pyrene)maleimide, 2,5-dimethoxystilbene-4'-maleimide, eosin-5-maleimide, fluorescein-5-maleimide, N-(4-(6-dimethylamino-2-benzofuranyl)phenyl)maleimide, benzophenone-4-maleimide, 4-dimethylaminophenylazophenyl-4'-maleimide, 1-(2-maleimidylethyl)-4-(5-(4-methoxyphenyl)oxazol-2-yl)pyridinium methanesulfonate, tetramethylrhodamine-5-maleimide, tetramethylrhodamine-6-maleimide, Rhodamine Red™ C2 maleimide, N-(5-aminopentyl)maleimide, N-(2-aminoethyl)maleimide, N-(2-(2-(((4-azido-2,3,5,6-tetrafluoro)benzoyl)amino)ethyl)dithio)ethyl)maleimide, 2-(1-(3-dimethylaminopropyl)-indol-3-yl)-3-(indol-3-yl) maleimide, N-(7-dimethylamino-4-methylcoumarin-3-yl)maleimide (DACM), 11H-Benzo[a]fluorene, Benzo[a]pyrene.

In one embodiment, the hedgehog polypeptide can be derivatived using pyrene maleimide, which can be purchased from Molecular Probes (Eugene, Oreg.), e.g., N-(1-pyrene)maleimide or 1-pyrenemethyl iodoacetate (PMIA ester). As illustrated in FIG. 1, the pyrene-derived hedgehog protein had an activity profile indicating that it was nearly 2 orders of magnitude more active than the unmodified form of the protein.

B. Making Hydrophobic Peptide Derivatives

According to the invention, the protein can also be modified using a hydrophobic peptide. As used herein, the term "peptide" includes a sequence of at least one amino acid residue. Preferably, the peptide has a length between one amino acid and 18–26 amino acids, the latter being the typical length of a membrane spanning segment of a protein. To create a peptide with hydrophobic character, the amino acids are selected predominantly from the following hydrophobic amino acids: phenylalanine, isoleucine, leucine, valine, methionine, tryptophan, alanine, proline, and tyrosine. The hydrophobic peptide can also contain unnatural amino acid analogs with hydrophobic character or D-amino acids, peptoid bonds, N-terminal acetylation or other features that decrease the peptide's susceptibility to proteolysis. Methods for substituting unnatural amino acids at specific sites in proteins are known (78, 79).

Generally, a hydrophobic peptide is appended to various sites on a protein. One site can be the N-terminal residue. Alternatively, the hydrophobic peptide is substituted in place of the N-terminal residue. In another embodiment, a hydrophobic peptide is appended to the C-terminus of the protein. Alternatively, the hydrophobic peptide is substituted in place of the C-terminal residue. The C-terminus can be the native C-terminal amino acid but it may also be the C-terminus of a truncated protein so that the hydrophobic peptide is appended to the final C-terminal amino acid of the truncated form, which is still referred to as the "C-terminus". A truncated hedgehog protein will retain activity when up to eleven amino acids are deleted from the native C-terminal sequence. The hydrophobic peptide may also be inserted between the N-terminal residue and the internal residue immediately adjacent to the N-terminal residue, or between the C-terminal residue and the residue immediately adjacent to the C-terminal residue, or between two internal residues.

In certain embodiments, the lipophilic moiety is an amphipathic polypeptide, such as magainin, cecropin, attacin, melittin, gramicidin S, alpha-toxin of *Staph. aureus*, alamethicin or a synthetic amphipathic polypeptide. Fusogenic coat proteins from viral particles can also be a convenient source of amphipathic sequences for the subject hedgehog proteins.

C. Making Lipid Derivatives

Another form of protein encompassed by the invention is a protein derivatized with a variety of lipid moieties. Generally, a "lipid" is a member of a heterogenous class of hydrophobic substances characterized by a variable solubility in organic solvents and insolubility, for the most part, in water. The principal classes of lipids that are encompassed within this invention are fatty acids and sterols (e.g., cholesterol). Derivatized proteins of the invention contain fatty acids which are cyclic, acyclic (i.e., straight chain), saturated or unsaturated, mono-carboxylic acids. Exemplary saturated fatty acids have the generic formula: $CH_3(CH_2)_n COOH$. The following table lists examples of some fatty acids that can be derivatized conveniently using conventional chemical methods.

TABLE 1

Exemplary Saturated and Unsaturated Fatty Acids

| | Common Name |
|---|---|
| Saturated Acids: $CH_3(CH_2)nCOOH$ | |
| Value of n | |
| 2 | butyric acid |
| 4 | caproic acid |
| 6 | caprylic acid |
| 8 | capric acid |
| 10 | lauric acid |
| 12 | myristic acid* |
| 14 | palmitic acid* |
| 16 | stearic acid* |
| 18 | arachidic acid* |
| 20 | behenic acid |
| 22 | lignoceric acid |
| Unsaturated Acids | |
| $CH_3CH=CHCOOH$ | crotonic acid |
| $CH_3(CH_2)_3CH=CH(CH_2)_7COOH$ | myristoleic acid* |
| $CH_3(CH_2)_5CH=CH(CH_2)_7COOH$ | palmitoleic acid* |
| $CH_3(CH_2)_7CH=CH(CH_2)_7COOH$ | oleic acid* |
| $CH_3(CH_2)_3(CH_2CH=CH)_2(CH_2)_7COOH$ | linoleic acid |
| $CH_3CH_2CH=CH)_3(CH_2)_7COOH$ | linolenic acid |
| $CH_3(CH_2)_3(CH_2CH=CH)_4(CH_2)_3COOH$ | arachidonic acid |

The asterisk (*) denotes the fatty acids that we found in recombinant hedgehog protein secreted from a soluble construct.

Other lipids that can be attached to the protein include branched-chain fatty acids and those of the phospholipid group such as the phosphatidylinositols (i.e., phosphatidylinositol 4-monophosphate and phosphatidylinositol 4,5-biphosphate), phosphatidycholine, phosphatidylethanolamine, phosphatidylserine, and isoprenoids such as farnesyl or geranyl groups.

Figure 7:
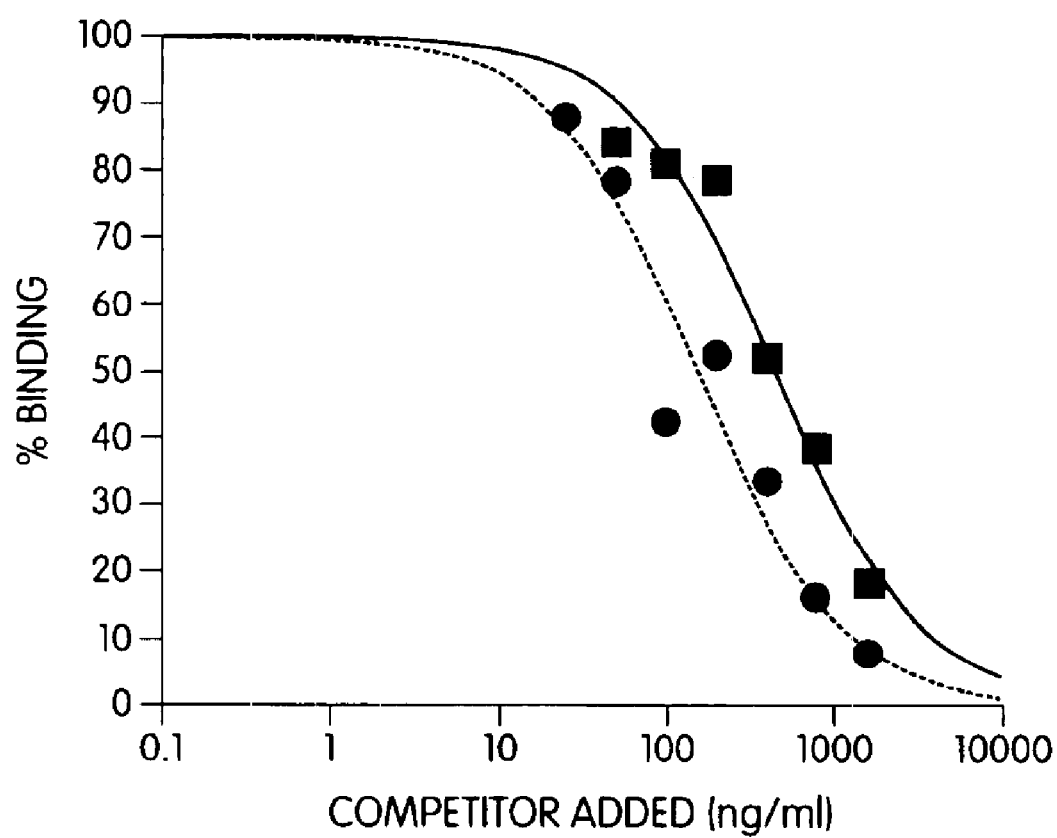
FIG. 7. Analysis of Shh in a receptor binding assay. The relative potency of soluble (6) and tethered (7) Shh for binding to patched was assessed on patched-transfected EBNA-293 cells by FACS analysis. Serial dilutions of the test samples were incubated with the EBNA-293 cells, washed, and then the percent binding measured by the ability of the samples to compete with Shh-Ig for binding to the cells. Bound Shh-Ig was quantified by mean fluorescence using a FITC-labeled anti-Ig antibody probe as the readout. The data were fitted to a hyberbolic curve by non-linear regression.

We have demonstrated that lipid-modified hedgehog proteins can be purified from either a natural source, or can be obtained by chemically modifying the soluble, unmodified protein. For protein purified from a natural source, we showed that when full-length human Sonic hedgehog (Shh) was expressed in insect cells and membrane-bound Shh purified from the detergent-treated cells using a combination of SP-Sepharose chromatography and immunoaffinity chromatography, that the purified protein migrated on reducing SDS-PAGE gels as a single sharp band with an apparent mass of 20 kDa (See Example 1). The soluble and membrane-bound Shh proteins were readily distinguishable by reverse phase HPLC, where the tethered forms eluted later in the acetonitrile gradient (See Example 1 and FIG. 3). We then demonstrated that human Sonic hedgehog is tethered to cell membranes in two forms, one form that contains a cholesterol, and therefore is analogous to the data reported previously for *Drosophila* hedgehog (18), and a second novel form that contains both a cholesterol nd a palmitic acid modification. Soluble and tethered forms of Shh were analyzed by electrospray mass spectrometry using a triple quadrupole mass spectrometer, equipped with an electrospray ion source (Example 1) as well as by liquid chromatography-mass spectrometry (See Example I). The identity of the N-terminal peptide from endoproteinase Lys-C digested tethered Shh was confirmed by MALDI PSD mass spectrometric measurement on a MALDI time of flight mass spectrometer. The site of palmitoylation was identified through a combination of peptide mapping and sequence analysis and is at the N-terminus of the protein (residue 1 of the sequence of the mature protein in SEQ ID NOS: 1–4). Both tethered forms were equally as active in the C3H10T1/2 alkaline phosphatase assay, but interestingly both were about 30-times more potent than soluble human Shh lacking the tether(s). The lipid modifications did not significantly affect the apparent binding affinity of Shh for its receptor, patched (FIG. 7).

We next tested the utility of the derivatized forms by assaying the relative potencies of soluble and tethered Shh alone or in the presence of the anti-hedgehog neutralizing Mab 5E1 on C3H10T1/2 cells measuring alkaline phosphatase induction. Moreover, the relative potency of soluble and tethered Shh for binding to patched was assessed on patched-transfected EBNA-293 cells by FACS analysis (Example 3).

For lipid-modified hedgehog obtained by chemically modifying the soluble, unmodified protein, we have showed that palmitic acid and other lipids can be added to soluble Shh to create a lipid-modified forms with increased potency in the C3H10T1/2 assay (Example 8). We have shown (Examples 1,2, and 8) that the thiol and α-amine on the N-terminal cysteine contribute to the lipid derivatization reaction. Without wishing to be bound by any particular theory, lipid modification on proteins starts with the formation of a thioester intermediate and the lipid moiety is then transferred to the α-amine of the N-terminus through the formation of a cyclic intermediate. Generally, therefore, the reactive lipid moiety can be in the form of thioesters of saturated or unsaturated carboxylic acids such as a Coenzyme A thioesters. Such materials and their derivatives may include, for example, commercially available Coenzyme A derivatives such as palmitoleoyl Coenzyme A, arachidoyl Coenzyme A, arachidonoyl Coenzyme A, lauroyl Coenzyme A and the like. These materials are readily available from Sigma Chemical Company (St. Louis, Mo., 1998 catalog pp. 303–306).

Figure 10:
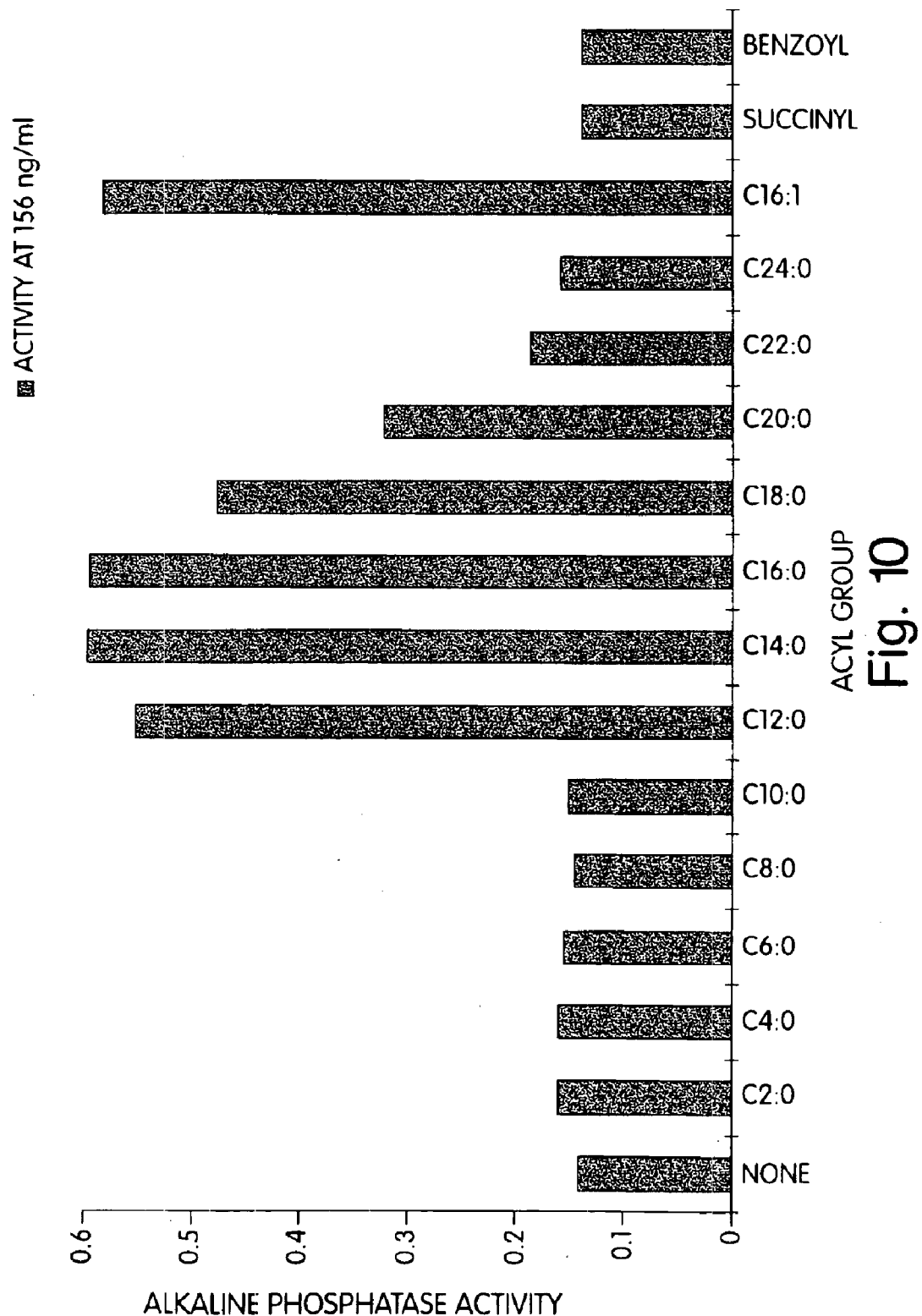
FIG. 10. Effect of lipid chain length on activity of human Sonic hedgehog. A series of fatty acid-modified hedgehog proteins was synthesized according to the present invention and the effect of the fatty acid chain length on hedgehog activity was tested using the C3H10T1/2 alkaline phosphatase induction assay described herein. The results are plotted as a bar graph.
Figure 11:
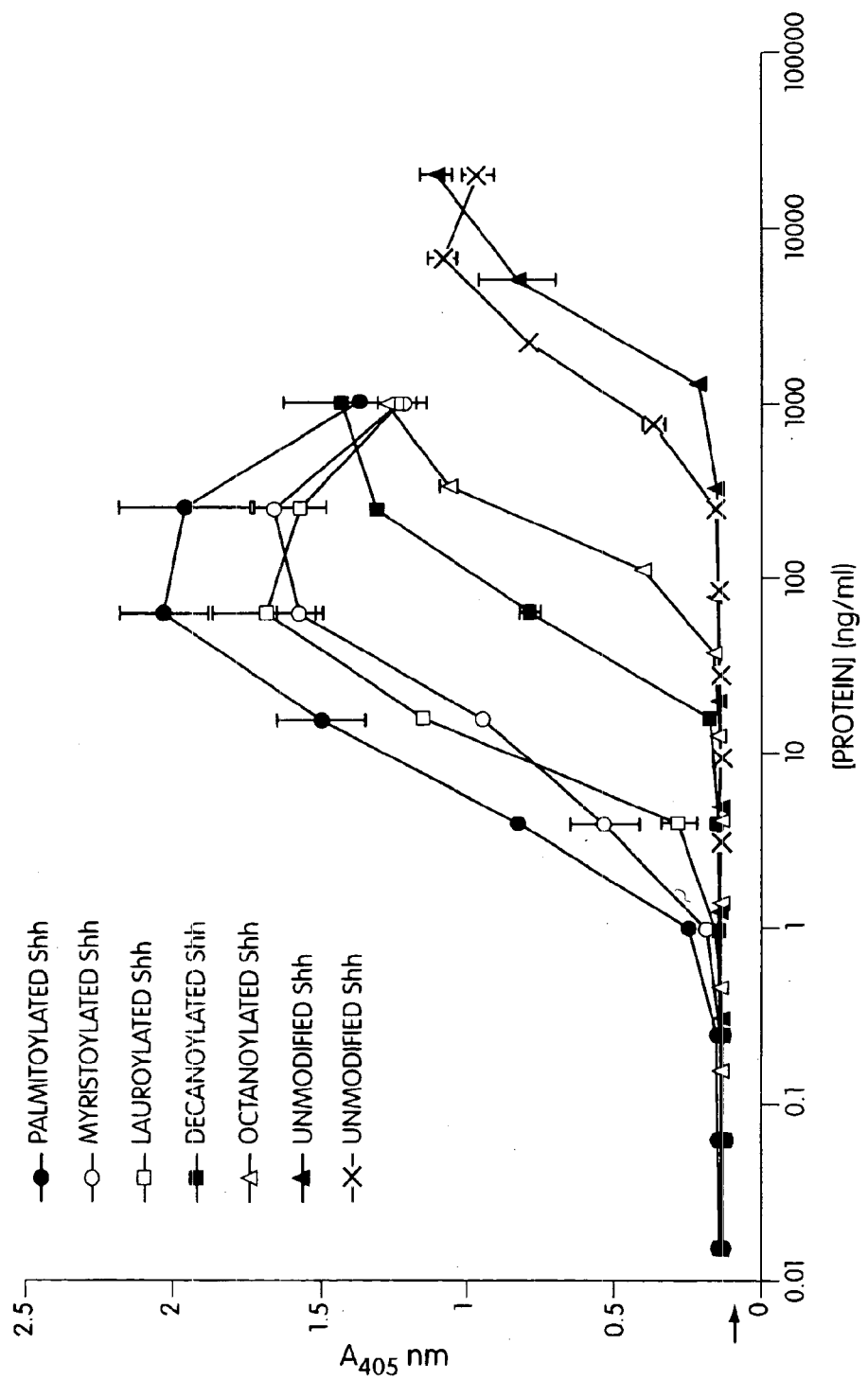
FIG. 11. C3H10T1/2 assay of palmitoylated, myristoylated, lauroylated, decanoylated, and octanoylated human Sonic hedgehog. Palmitoylated, lauroylated, decanoylated, and octanoylated human Sonic hedgehog formulated in 5 mM $Na_2HPO_4$ pH 5.5, 150 mM NaCl, 1% octylglucoside, 0.5 mM DTT, and myristoylated human Sonic hedgehog, formulated in 150 mM NaCl, 0.5 mM DTT, were assayed on C3H10T1/2 cells measuring alkaline phosphatase induction. The numbers represent the mean of duplicate determinations. Serial 3-fold dilutions of palmitoylated (○), myristoylated (●), lauroylated (□), decanoylated (■), octanoylated (Δ), and unmodified (▲ and ×) human Sonic hedgehog were incubated with the cells for 5 days and the resulting levels of alkaline phosphatase measured at 405 nm using the chromogenic substrate p-nitrophenyl phosphate. The palmitoylated, myristoylated, lauroylated, and decanoylated proteins were assayed in one experiment with the unmodified protein shown as (▲), while the octanoylated protein was assayed in another experiment with the unmodified protein shown as (×). The arrow on the y-axis denotes the background level of alkaline phosphatase in the absence of added hedgehog protein.
Figure 12A:
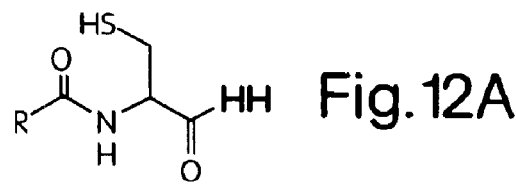
FIG. 12. Generic structures of various hydrophobically-modified forms of hedgehog. (A) Fatty amide derivative where R=a hydrocarbon chain of a fatty acid; (B) thiazolidine derivative where R=a hydrocarbon; (C) amino acid substitution where R=a hydrophobic amino acid side chain; (D) maleimide derivative where R=a hydrocarbon; (E) SH=free thiol on N-terminal cysteine of wild type hedgehog; (F) an iodoacetamide derivative where $R_1$=a hydrocarbon and $R_2$=either H or a hydrocarbon; and (G) thiomorpholinyl derivative where R=a hydrocarbon. For all structures, HH=hedgehog.
Figure 12B:
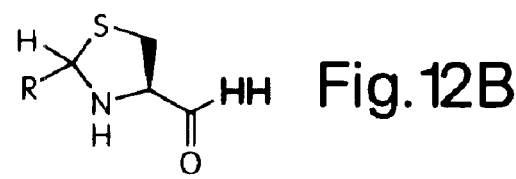
Figure 12C:
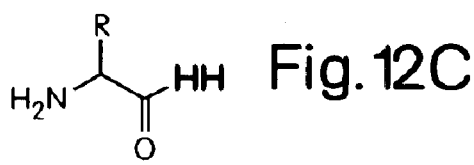
Figure 12D:
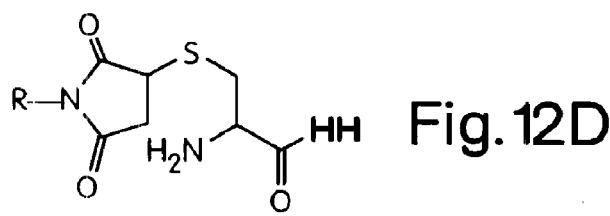
Figure 12E:
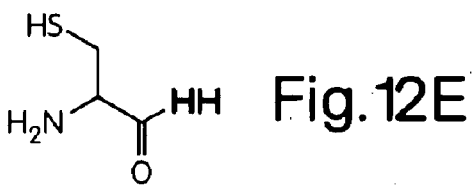
Figure 12F:
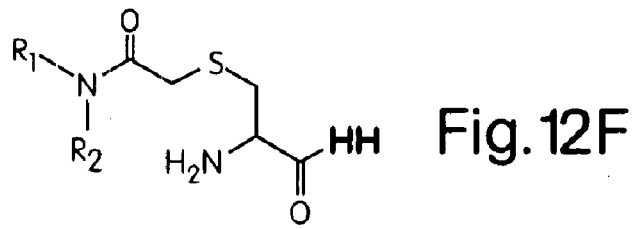
Figure 12G:
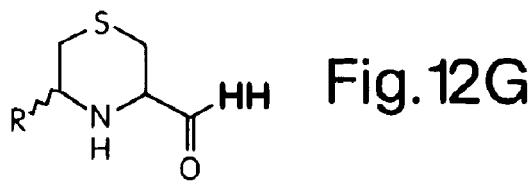

The effect of different lipid moieties on functional activity of hedgehog protein has been assayed (See Example 8 and FIGS. 10 and 11). Similarly, the effect of different lipid moieties on functional activity of other proteins such as those described above in Section III, may be conveniently tested using methods known to workers of ordinary skill. For instance, functional testing of gelsolin (50), various interferons (interferon-α, interferon-β and interferon-γ), the various interleukins (e.g., IL-1, -2, -3, -4, and the like), the tumor necrosis factors-α and -β, and other growth factors that are lipid-modified according to the invention can be accomplished using well known methods.

Although we have established chemical means by which a fatty acid can be attached to the N-terminal cysteine of hedgehog proteins, it might be expected that lipids can be attached to the same or other sites using enzymically catalyzed reactions. Palmitoylation of proteins in vivo is catalyzed by a class of enzymes known as palmitoyl-CoA:protein S-palmitoyltransferases. Using purified enzymes, in vitro acylation of protein substrates has been demonstrated (80, 81). The substrate specificities of the palmitoyltransferase enzymes are not well defined; an analysis of palmitoylation sites of cellular and viral proteins finds little in the way of a consensus sequence surrounding the modified cysteine residue, but suggests a common presence of a lysine or arginine residue within two amino acids of the cysteine, and large, hydrophobic amino acids near the cysteine. The amino-terminal sequence of Shh, CGPGRGFG, may fit this consensus sequence and serve as a recognition site for palmitoylation.

As an alternative, myristoylation of the amino terminus of hedgehog proteins could be carried out using an N-myristoyl transferase (NMT), a number of which have been well characterized in both mammals (82) and in yeast (83). A recognition site for N-myristoyltransferase could be engineered into the hedgehog N-terminal sequence to facilitate recognition by the enzyme. Both of these strategies would require the use of fatty acyl-coenzyme A derivatives as substrates, as are used for the non-enzymic fatty acylation of human Sonic hedgehog described in Example 8. Alternatively, a protein with an engineered recognition sequence may be myristoylated during expression in a suitable cell line. Another method of modifying a protein such as hedgehog with a hydrophobic moiety is to create a recognition site for the addition of an isoprenoid group at the C-terminus of the protein. The recognition site for farnesyl and geranyl-geranyl addition are known and the protein may be modified during expression in a eukaryotic cell (Gelb et al., Cur. Opin. Chem. Biol. 2: 40–48 (1998)).

VI. Multimeric Protein Complexes

Hydrophobically-modified proteins described herein are particularly amenable to being made into multimeric protein complexes. Multimeric protein complexes of the invention include proteins, optionally attached via their hydrophobic (e.g., lipid) moiety to a vesicle. The vesicle may be a naturally occurring biological membrane, purified away from natural material, or the vesicle may be a synthetic construction. Preferred vesicles are substantially spherical structures made of amphiphiles, e.g., surfactants or phospholipids. The lipids of these spherical vesicles are generally organized in the form of lipids having one or more structural layers, e.g., multilamellar vesicles (multiple onion-like shells of lipid bilayers which encompass an aqueous volume between the bilayers) or micelles.

In particular, liposomes are small, spherical vesicles composed primarily of various types of lipids, phospholipids, and secondary lipophilic components. These components are normally arranged in a bilayer formation, similar to the lipid arrangement of biological membranes.

Typically, the polar end of a component lipid or lipid-like molecule is in contact with the surrounding solution, usually an aqueous solution, while the non-polar, hydrophobic end of the lipid or lipid-like molecule is in contact with the non-polar, hydrophobic end of another lipid or lipid-like molecule. The resulting bilayer membrane (i.e., vesicle) is selectively permeable to molecules of a certain size, hydrophobicity, shape, and net charge. Most vesicles are lipid or lipid-like in nature, although alternative liposome bilayer formulations, comprising a surfactant with either a lipid or a cholesterol, exist.

Liposome vesicles may be particularly preferred in that they find many therapeutic, diagnostic, industrial, and commercial applications. They are used to deliver molecules which are not readily soluble in water, or when directed timed release is desired. Because of their selective permeability to many chemical compounds, liposomes are useful as delivery vehicles for drugs and biological materials. Thus, lipid-derivatized proteins such as hedgehog can be made multimeric by being incorporated into the lipid bilayer of liposome vesicles. Upon reaching the target site, the liposomes may be degraded (for example, by enzymes in the gastro-intestinal tract) or they may fuse with the membranes of cells.

Several methods of preparing vesicles such as liposomes are known. The production of phospholipid vesicles is well known (53). For a general review of commonly used methods, see (54). Among the more common of these are (I) sonication of a solution containing lipids sometimes followed by evaporation/lyophilization and rehydration (see, e.g. Stryer, Biochemistry, pp. 290–291, Freeman & Co., New York, (1988), and (55); (2) homogenization of a lipid solution, sometimes at high pressure or high shearing force (see e.g. U.S. Pat. No. 4,743,449 issued 10 May 1988, and U.S. Pat. No. 4,753,788, issued 28 Jun. 1988), (3) hydration and sometimes sonication of a dried film of vesicle-forming lipids wherein the lipid film is prepared by evaporation of a solution of lipids dissolved in an organic solvent (see e.g. U.S. Pat. No. 4,452,747 issued 5 Jun. 1984, U.S. Pat. No. 4,895,719 issued 23 Jan. 1990, and U.S. Pat. No. 4,946,787 issued 7 Aug. 1990), (4) lyophilization or evaporation and rehydration (see e.g. U.S. Pat. No. 4,897,355 issued 30 Jan. 1990, EP 267,050 published 5 Nov. 1988, U.S. Pat. No. 4,776,991 issued 11 Oct. 1988, EP 172,007 published 19 Feb. 1986, and Australian patent application AU-A-48713/85 published 24 Apr. 1986), (5) solvent injection or infusion of a lipid solution into an aqueous medium or vice versa (see e.g. (56); U.S. Pat. No. 4,921,757 issued 1 May 1990, U.S. Pat. No. 4,781,871 issued 1 Nov. 1988, WO 87/02396 published 24 Mar. 1988, and U.S. Pat. No. 4,895,452 issued 23 Jan. 1990), (6) spray drying (see e.g. Australian patent application AU-A-48713/85 published 24 Apr. 1986, and U.S. Pat. No. 4,830,858 issued 16 May 1989), (7) filtration (see e.g. WO 85/01161), (8) reverse-phase evaporation. See e.g. (57); and (9) combinations of the above methods. See e.g. (58) and (59).

Preferred lipids and lipid-like components suitable for use in preparing vesicles include phospholipids, a mixture of phospholipids, polar lipids, neutral lipids, fatty acids, and their derivatives. A preferred lipid has the characteristic that when dispersed alone in water, at a temperature above the lipid transition temperature, they are in a lipid emulsion phase. In certain embodiments, the lipid is a single-aliphatic chain of greater than about 12 carbons and can be either saturated or unsaturated, or substituted in other ways. Suitable lipids include the ester, alcohol, and acid forms of the following fatty acids: stearate, oleic acid, linoleic acid, arachidate, arachidonic acid, and other single-aliphatic chains acids. Further candidates include the ester, alcohol, and acid forms of the retinols, in particular, retinol and retinoic acid. Other preferred lipids include phosphatidylcholine (PC), phosphatidylglycerol (PG) and their derivatives, created synthetically or derived from a variety of natural sources.

In certain embodiments, the vesicle may be stabilized sterically by the incorporation of polyethylene glycol (PEG), or by the PEG headgroups of a synthetic phospholipid (PEG conjugated to distearoyl phosphatidylethanolamine (DSPE), see e.g. (61)). Preferred surfactants are those with good miscibility such as Tween™, Triton™, sodium dodecyl sulfate (SDS), sodium laurel sulfate, or sodium octylglycoside.

Preferred surfactants form micelles when added to aqueous solution above the surfactant's phase transition temperature. The surfactants may be composed of one or more aliphatic chains. These aliphatic chains may be saturated, unsaturated, or substituted in other ways, such as by ethoxylation; typically the aliphatic chain contains greater than about 12 carbons. Additional suitable surfactants include the following: lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT series (Mona Industries, Inc, Paterson, N.J.). See also Example 4.

Preferred sterols and sterol esters suitable for use in preparing multimeric protein complexes include cholesterol, cholestanol, cholesterol sulfate, and other cholesterol analogs and derivatives. The fact that a vesicle may comprise many different lipids and detergents allows great flexibility in engineering a tethered protein-vesicle complex with desired properties. For example, one may produce vesicles that bind different number of proteins by varying the lipid composition of the starting materials to create larger vesicles, or by increasing the percentage of phosphatidylinositol lipids in the vesicle.

VII. Utilities

Generally, the modified proteins described herein are useful for treating the same medical conditions that can be treated with the unmodified forms of the proteins. However, the hydrophobically-modified proteins described herein provide several significant improvements over the unmodified forms. First, their increased potency enables treatment with smaller amounts of protein and over shorter periods of time. This will be important in both systemic and CNS applications. Secondly, replacement of the N-terminal cysteine with a less chemically reactive amino acid allows for easier production, formulation, and storage of a protein for clinical use. Thirdly, the pharmacodynamics of a protein will be altered by hydrophobic modification and this will allow the proteins to be localized in the vicinity of the site of administration, thus increasing their safety, by minimizing systematic exposure, and their effectiveness by increasing their local concentration. The proteins of the invention are also useful in diagnostic compositions and methods to detect their corresponding receptors.

As an example of the first point, it has been found that the half-life of hedgehog is very short after systemic application and that multiple injections are required to achieve a robust response to the protein. The higher potency of the modified forms and the possibility of formulation in liposomes provides a means of achieving a response with fewer treatments. For CNS applications, the higher potency provides a means to supply an adequate amount of protein in the small volumes required for direct injection into the CNS.

The importance of the second point is illustrated by the fact that we have found that the N-terminal cysteine of hedgehog is highly susceptible to chemical attack, either to form other chemical adducts or to oxidatively-dimerize with another hedgehog protein. To prevent this, special buffers and procedures are used during purification, and dithiothreitol is used in the final formulation. These precautions necessitate careful evaluation of the effects of the formulation buffer in animal models.

As an example of the third point, the more limited the range over which a protein diffuses away from the site of administration, the higher the local concentration. This higher local concentration may therefore allow more specific clinical responses during the treatment of neurological disorders after direct injection into the desired region of the brain or spinal cord.

Similarly, the modified proteins can be administered locally to the site of bone fractures to help heal these fractures, in the gonads to treat fertility disorders, intraocularly to treat eye disorders, and under the skin to treat dermatological conditions, and to stimulate local hair growth. Localization of the hydrophobically-modified proteins to the site of administration therefore reduces possibly undesirable systemic exposure to other tissues and organs.

For therapeutic use, hydrophobically-modified proteins of the invention are placed into pharmaceutically acceptable, sterile, isotonic formulations and optionally are administered by standard means well known in the field. The formulation is preferably liquid or may be lyophilized powder. It is envisioned that a therapeutic administration of, for instance, a multimeric protein complex may comprise liposomes incorporating the derivatized proteins described herein.

It will be appreciated by persons having ordinary skill in the art that the particular administration, dosage, and clinical applications of a hydrophobically-modified protein of the invention will vary depending upon the particular protein and its biological activity.

As but one example of the application of the proteins of this invention in a therapeutic context, therapeutic hydrophobically-modified hedgehog proteins can be administered to patients suffering from a variety of neurological conditions. The ability of hedgehog protein to regulate neuronal differentiation during development of the nervous system and also presumably in the adult state indicates that hydrophobically-modified hedgehog can reasonably be expected to facilitate control of adult neurons with regard to maintenance, functional performance, and aging of normal cells; repair and regeneration processes in lesioned cells; and prevention of degeneration and premature death which results from loss of differentiation in certain pathological conditions. In light of this, the present hydrophobically-modified hedgehog compositions, by treatment with a local infusion can prevent and/or reduce the severity of neurological conditions deriving from: (i) acute, subacute, or chronic injury to the nervous system, including traumatic injury, chemical injury, vessel injury, and deficits (such as the ischemia from stroke), together with infectious and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like; and (iv) chronic immunological diseases of the nervous system, including multiple sclerosis. The hydrophobically-modifed protein may also be injected into the cerebrospinal fluid, e.g., in order to address deficiencies of brain cells, or into the lymph system or blood stream as required to target other tissue or organ system-specific disorders.

Hedgehog compositions of the invention may be used to rescue, for example, various neurons from lesion-induced death as well as guiding reprojection of these neurons after such damage. Such damage can be attributed to conditions that include, but are not limited to, CNS trauma infarction, infection, metabolic disease, nutritional deficiency, and toxic agents (such as cisplatin treatment). Certain hedgehog proteins cause neoplastic or hyperplastic transformed cells to become either post-mitotic or apoptotic. Such compositions may, therefore, be of use in the treatment of, for instance, malignant gliomas, medulloblastomas and neuroectodermal tumors.

The proteins may also be linked to detectable markers, such as fluoroscopically or radiographically opaque substances, and administered to a subject to allow imaging of tissues which express hedgehog receptors. The proteins may also be bound to substances, such as horseradish peroxidase, which can be used as immunocytochemical stains to allow visualization of areas of hedgehog ligand-positive cells on histological sections. Hydrophobically-modified proteins of the invention, either alone or as multivalent protein complexes, can be used to specifically target medical therapies against cancers and tumors which express the receptor for the protein. Such materials can be made more effective as cancer therapeutics by using them as delivery vehicles for antineoplastic drugs, toxins, and cytocidal radionuclides, such as yttrium 90.

A toxin may also be conjugated to hydrophobically-modified hedgehog (or vesicle-containing multivalent complexes thereof) to selectively target and kill hedgehog-responsive cells, such as a tumor expressing hedgehog receptor(s). Other toxins are equally useful, as known to those of skill in the art. Such toxins include, but are not limited to, *Pseudomonas* exotoxin, *Diphtheria* toxin, and saporin. This approach should prove successful because hedgehog receptor(s) are expressed in a very limited number of tissues. Another approach to such medical therapies is to use radioisotope labeled, hydrophobically-modified protein (or multivalent complexes thereof). Such radiolabeled compounds will preferentially target radioactivity to sites in cells expressing the protein receptor(s), sparing normal tissues. Depending on the radioisotope employed, the radiation emitted from a radiolabeled protein bound to a tumor cell may also kill nearby malignant tumor cells that do not express the protein receptor. A variety of radionuclides may be used. Radio-iodine (for example, $^{131}$I) has been successful when employed with monoclonal antibodies against CD20 present on B-cell lymphomas (63).

The protein compositions to be used in therapy will be formulated and dosages established in a fashion consistent with good medical practice taking into account the disorder to be treated, the condition of the individual patient, the site of delivery of the isolated polypeptide, the method of administration, and other factors known to practitioners. The therapeutic may be prepared for administration by mixing a protein, a protein-containing vesicle, or a derivatized complex at the desired degree of purity with physiologically acceptable carriers (i.e. carriers which are nontoxic to recipients at the dosages and concentrations employed).

It is envisioned that local delivery to the site will be the primary route for therapeutic administration of the proteins of this invention. Intravenous delivery, or delivery through catheter or other surgical tubing may also be envisioned. Alternative routes include tablets and the like, commercially available nebulizers for liquid formulations, and inhalation of lyophilized or aerosolized formulations. Liquid formulations may be utilized after reconstitution from powder formulations.

The dose administered will be dependent upon the properties of the vesicle and protein employed, e.g. its binding activity and in vivo plasma half-life, the concentration of the vesicle and protein in the formulation, the administration route, the site and rate of dosage, the clinical tolerance of the patient involved, the pathological condition afflicting the patient and the like, as is well known within the skill of the physician. Generally, doses of from about $5 \times 10^{-7}$ to $5 \times 10^{-9}$ Molar of protein per patient per administration are preferred, although the dosage will depend on the nature of the protein. Different dosages may be utilized during a series of sequential administrations.

The invention is also directed towards a pharmaceutical formulation which includes a hedgehog protein modified according to the invention in combination with a pharmaceutically acceptable carrier. In one embodiment, the formulation also includes vesicles.

The hydrophobically-modified hedgehog proteins of the invention are also useful in gene therapy methods. For neurodegenerative disorders, several animal models are available that are believed to have some clinical predicative value. For Parkinson's disease, models involve the protection, or the recovery in rodents or primates in which the nigral-striatal dopaminergic pathway is damaged either by the systemic administration of MPTP or the local (intracranial) administration of 6-hydroxydopamine [6-OHDA], two selective dopaminergic toxins. Specific models are: MPTP-treated mouse model (64); MPTP-treated primate (marmoset or Rhesus) model (65), and the unilateral 6-OHDA lesion rat model (66). For ALS, (Amyotrophic lateral sclerosis) models involve treatment of several mice strains that show spontaneous motor neuron degeneration, including the wobbler (67) and pmn mice (68), and of transgenic mice expressing the human mutated superoxidase dismutase (hSOD) gene that has been linked to familial ALS (69). For spinal cord injury the most common models involve contusion injury to rats, either through a calibrated weight drop, or fluid (hydrodynamic) injury (70). For Huntington's, models involve protection from excitotoxin (NMDA, quinolinic acid, kainic acid, 3-nitro-propionic acid, APMA) lesion to the striatum in rats (71, 72). Recently, a model of transgenic mice overexpressing the human trinucleotide expanded repeat in the huntingtin gene has also been described (73). For multiple sclerosis EAE in mice and rats is induced by immunization with MBP (myelin basic protein), or passive transfer of T cells activated with MBP (74). For Alzheimer's, a relevant murine model is a determination of protection against lesion of the fimbria-fornix in rats (septal lesion), the main nerve bundle supplying the cholinergic innervation of the hippocampus (75), as well as use of transgenic mice overexpressing the human beta-amyloid gene. For peripheral neuropathies, a relevant model is protection against loss of peripheral nerve conductance caused by chemtherapeutic agents such as taxol, vincristine, and cisplatin in mice and rats (76).

This invention will now be described more fully with reference to the following, non-limiting, Examples.

EXAMPLE 1

Human Sonic Hedgehog is Lipid-Modified when Expressed in Insect Cells

A. Expression of Human Sonic Hedgehog

The cDNA for full-length human Sonic hedgehog (Shh) was provided as a 1.6 kb EcoRI fragment subcloned into pBluescript SK$^+$ (20) (a gift of David Bumcrot from Ontogeny, Inc., Cambridge Mass.). The 5' and 3' NotI sites immediately flanking the Shh open reading frame were added by unique site elimination mutagenesis using a Pharmacia kit following the manufacturer's recommended protocol. The 1.4 kb NotI fragment carrying the full-length Shh cDNA was then subcloned into the insect expression vector, pFastBac (Life Technologies, Inc.). Recombinant baculovirus was generated using the procedures supplied by Life Technologies, Inc. The resulting virus was used to create a high titer virus stock. Methods used for production and purification of Shh are described below. The presence of membrane-associated Shh was examined by FACS and by Western blot analysis. Peak expression occurred 48 h post-infection. For Western blot analysis, supernatants and cell lysates from Shh-infected or uninfected cells were subjected to SDS-PAGE on a 10–20% gradient gel under reducing conditions, transferred electrophoretically to nitrocellulose, and the Shh detected with a rabbit polyclonal antiserum raised against an N-terminal Shh 15-mer peptide-keyhole limpet hemocyanin conjugate. The cell lysates were made by incubating the cells for 5 min at 25° C. in 20 mM Na$_2$HPO$_4$ pH 6.5, 1% Nonidet P-40 and 150 mM NaCl or 20 mM Tris-HCl pH 8.0, 50 mM NaCl, 0.5% Nonidet P-40 and 0.5% sodium deoxycholate and then pelleting particulates at 13,000 rpm for 10 min at 4° C. in an Eppendorf centrifuge.

B. Purification of Membrane-Tethered Human Sonic Hedgehog

The membrane-tethered form of Shh was produced in High Five™ insect cells (Invitrogen) using the recombinant baculovirus encoding full-length Shh discussed above. High Five™ cells were grown at 28° C. in sf900 II serum free medium (Life Technologies, Inc.) in a 10 L bioreactor controlled for oxygen. The cells were infected in late log phase at ca. 2×10¹ cells/mL with virus at a MOI of 3 and harvested 48 h after infection (cell viability at the time of harvest was >50%). The cells were collected by centrifugation and washed in 10 mM $Na_2HPO_4$ pH 6.5, 150 mM NaCl pH plus 0.5 mM PMSF. The resulting cell pellet (150 g wet weight) was suspended in 1.2 L of 10 mM $Na_2HPO_4$ pH 6.5, 150 mM NaCl, 0.5 mM PMSF, 5 μM pepstatin A, 10 μg/mL leupeptin, and 2 μg/mL E64, and 120 mL of a 10% solution of Triton X-100 was then added.

After a 30 min incubation on ice, particulates were removed by centrifugation (1500×g, 10 min). All subsequent steps were performed at 4–6° C. The pH of the supernatant was adjusted to 5.0 with a stock solution of 0.5 M MES pH 5.0 (50 mM final) and loaded onto a 150 ml SP-Sepharose Fast Flow column (Pharmacia). The column was washed with 300 mL of 5 mM $Na_2HPO_4$ pH 5.5, 150 mM NaCl, 0.5 mM PMSF, 0.1% Nonidet P-40, then with 200 mL of 5 mM $Na_2HPO_4$ pH 5.5, 300 mM NaCl, 0.1% Nonidet P-40, and bound hedgehog eluted with 5 mM $Na_2HPO_4$ pH 5.5, 800 mM NaCl, 0.1% Nonidet P-40.

The Shh was next subjected to immunoaffinity chromatography on 5E1-Sepharose resin that was prepared by conjugating 4 mg of antibody per mL of CNBr activated Sepharose 4B resin. The SP-Sepharose elution pool was diluted with two volumes of 50 mM HEPES pH 7.5 and batch loaded onto the 5E1 resin (1 h). The resin was collected in a column, washed with 10 column volumes of PBS containing 0.1% hydrogenated Triton X-100 (Calbiochem), and eluted with 25 mM $NaH_2PO_4$ pH 3.0, 200 mM NaCl, 0.1% hydrogenated Triton X-100. The elution fractions were neutralized with 0.1 volume of 1M HEPES pH 7.5 and analyzed for total protein content from absorbance measurements at 240–340 nm and for purity by SDS-PAGE. Fractions were stored at −70° C.

Peak fractions from three affinity steps were pooled, diluted with 1.3 volumes of 50 mM HEPES pH 7.5, 0.2% hydrogenated Triton X-100 and again batch loaded onto the 5E1 resin. The resin was collected in a column, washed with three column volumes of PBS pH 7.2, 1% octylglucoside (US Biochemical Corp.), and eluted with 25 mM $NaH_2PO_4$ pH 3.0, 200 mM NaCl, 1% octylglucoside. The elution fractions were neutralized and analyzed as described above, pooled, filtered through a 0.2 micron filter, aliquoted, and stored at −70° C.

When full-length human sonic hedgehog (Shh) was expressed in High Five™ insect cells, over 95% of the N-terminal fragment was detected by Western blotting in a form that was cell-associated. By SDS-PAGE, the purified protein migrated as a single sharp band with apparent mass of 20 kDa (FIG. 1, lane c). The protein migrated faster by about 0.5 kDa than a soluble version of the protein that had been produced in E. coli (FIG. 1, lanes b–d), consistent with data published previously (19). Similarly as described (19), the soluble and membrane-bound Shh proteins were also readily distinguishable by reverse phase HPLC where the tethered form eluted later in the acetonitrile gradient. The concentration of acetonitrile needed for elution of the membrane-bound form was 60% versus only 45% with the soluble form, indicating a significant increase in the hydrophobicity of the protein.

C. Mass Spectrometry Analysis of Membrane-Tethered Human Sonic Hedgehog

Aliquots of Shh were subjected to reverse phase HPLC on a C₄ column (Vydac, Cat. No. 214TP104, column dimensions 4.6 mm internal diameter×250 mm) at ambient temperature. Bound components were eluted with a 30 min 0–80% gradient of acetonitrile in 0.1% trifluoroacetic acid at a flow rate of 1.4 mL/min. The column effluent was monitored at 280 nm and 0.5 min fractions were collected. 25 μL aliquots of fractions containing protein were dried in a Speed Vac concentrator, dissolved in electrophoresis sample buffer, and analyzed by SDS-PAGE. Hedgehog-containing fractions were pooled, concentrated 4-fold in a Speed Vac concentrator and the protein content assayed by absorbance at 280 nm using an extinction coefficient of 1.33 for a 1 mg/mL solution of Shh. Samples were subjected to ESI-MS on a Micromass Quattro II triple quadrupole mass spectrometer, equipped with an electrospray ion source. A volume of 6 μL of HPLC-purified hedgehog was infused directly into the ion source at a rate of 10 μL/min using 50% water, 50% acetonitrile, 0.1% formic acid as the solvent in the syringe pump. Scans were acquired throughout the sample infusion. All electrospray mass spectral data were acquired and stored in profile mode and were processed using the Micromass MassLynx data system.

Peptides from an endoproteinase Lys-C digest of pyridylethylated-Shh were analyzed by reverse phase HPLC in line with the Micromass Quattro II triple quadrupole mass spectrometer. The digest was separated on a Reliasil $C_{18}$ column using a Michrom™ ultrafast Microprotein Analyzer system at a flow rate of 50 μL/min with a 5–85% acetonitrile gradient in 0.05% trifluoroacetic acid. Scans were acquired from m/z 400–2000 throughout the run and processed as described above.

Sequencing of the N-terminal peptide from tethered Shh was performed by Post Source Decay (PSD)-measurement on a Voyager-DET™ STR (PerSeptive Biosystems, Framingham, Mass.) time-of-flight (TOF) mass spectrometer using α-cyano-4-hydroxycinnamic acid as the matrix (22,23). Exactly 0.5 μL of HPLC-purified endoproteinase Lys-C peptide was mixed with 0.5 μL of matrix on the target plate. To cover the entire spectrum of fragment ions, the mirror voltages were decreased from 20 to 1.2 kv in 11 steps.

Figure 2A:
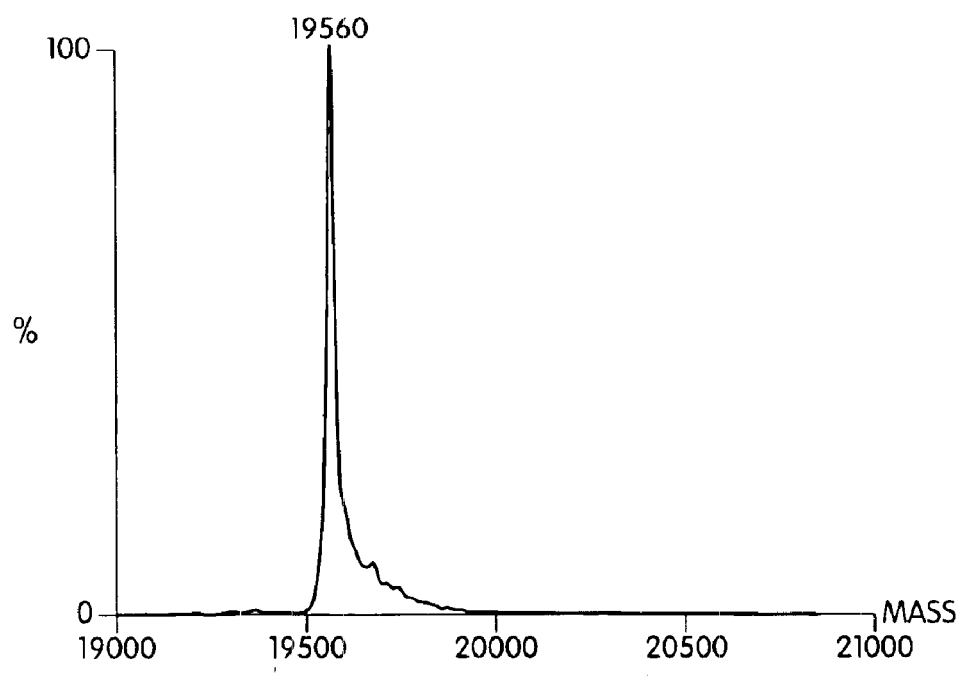
FIG. 2. Analysis of purified Shh by ESI-MS. Soluble human Shh (A) and tethered human Shh (B) were analyzed by ESI-MS on a Micromass Quattro II triple quadrupole mass spectrometer, equipped with an electrospray ion source. All electrospray mass spectral data were acquired and stored in profile mode and were processed using the Micromass MassLynx data system. Molecular mass spectra are shown (mass assignments were generated by the data system).
Figure 2B:
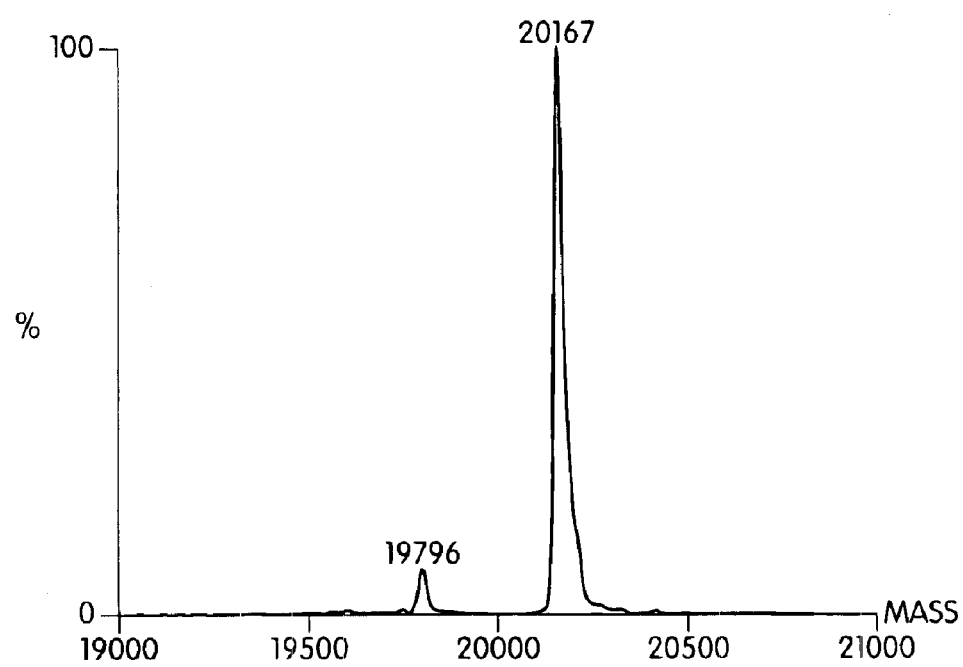
Figure 3A:
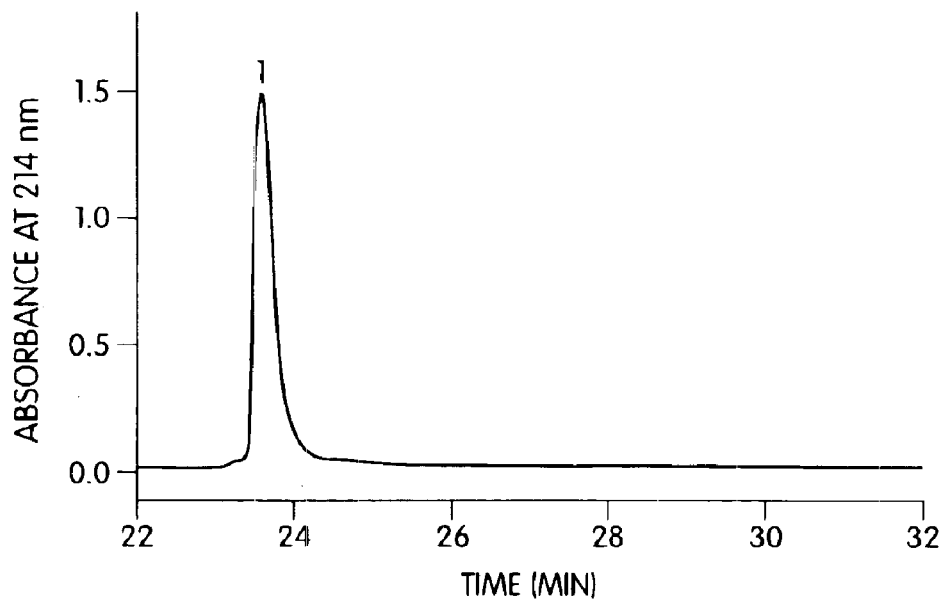
FIG. 3. Analysis of tethered Shh by reverse phase HPLC. Soluble human Shh (A), tethered human Shh from High Five™ insect cells (B), tethered human Shh from EBNA-293 cells (C), and cell-associated rat Shh (D) were subjected to reverse phase HPLC on a narrow bore Vydac $C_4$ column (2.1 mm internal diameter×250 mm). The column was developed with a 30 min, 0–80% acetonitrile gradient in 0.1% trifluoroacetic acid at 0.25 mL/min and the effluent monitored using a photodiode array detector from 200–300 nm (data shown at 214 nm). Peak fractions were collected and characterized further by SDS-PAGE and MS (data summarized in Tables 2, 3, and 4.
Figure 3B:
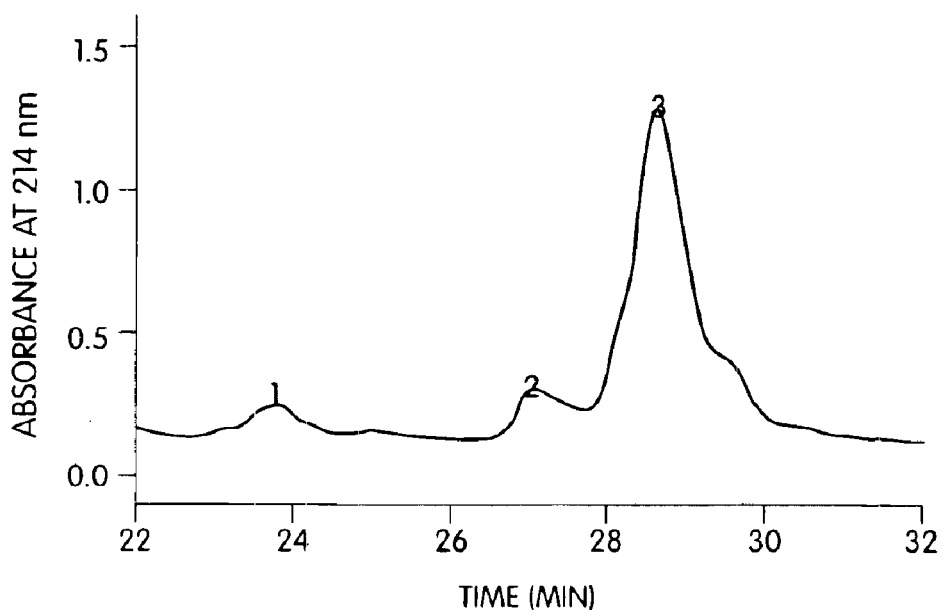
Figure 3C:
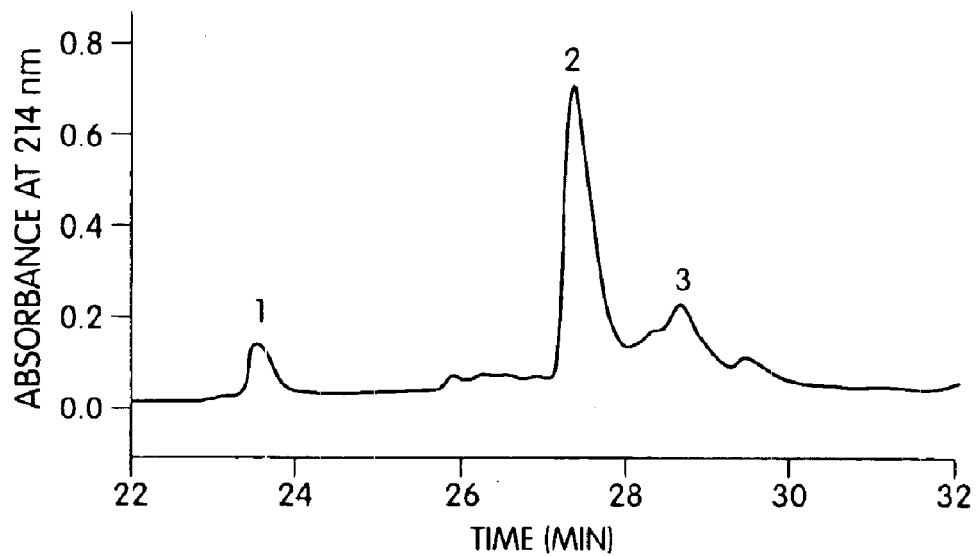
Figure 3D:
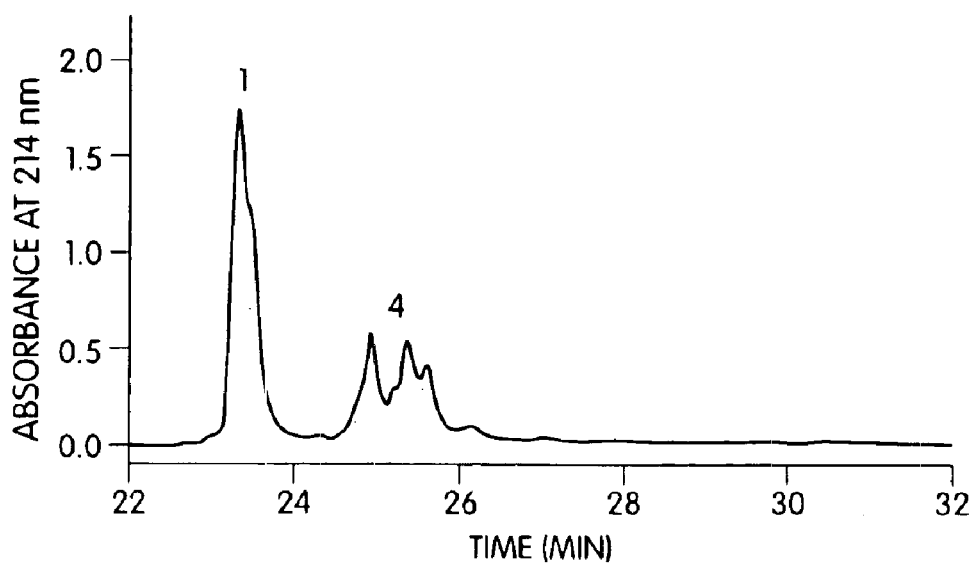

Electrospray ionization mass spectrometry data for the soluble and membrane-bound forms of Shh showed primary species with masses of 19560 and 20167 Da, respectively (FIG. 2). The measured mass of 19560 Da matches the predicted mass for Shh starting with Cys-1 and terminating with Gly-174 (calc. mass of 19560.02 Da). In contrast, the 20167 Da mass did not agree with any available prediction nor could the difference in the masses of the tethered and soluble forms, 607 Da, be accounted for by any known modification or by aberrant proteolytic processing. Previously, Porter et al. (18) demonstrated that *Drosophila* hedgehog contained a cholesterol moiety and thus it was possible that the mass difference in the human system was due, at least in part, to cholesterol (calculated mass for esterified cholesterol is 368.65 Da). The presence of a minor component in the mass spectrum of tethered Shh at 19796 Da, which differs from the primary peak by 371 Da, supported this notion.

Further evidence for cholesterol was obtained by treating the tethered Shh with a mild alkali under conditions that can break the cholesterol linkage without disrupting peptide bonds (18), and then reanalyzing the reaction products by mass spectrometry (MS). Briefly, insect cell-derived Shh was treated with 50 mM KOH, 95% methanol for 1 h at ambient temperature and then analyzed by ESI-MS or digested with endoproteinase Lys-C and subjected to LC (liquid chromatography)-MS on the Micromass Quattro II triple quadrupole mass spectrometer. For samples subjected to LC-MS, the proteins were first treated with 4-vinylpyridine. Base treatment shifted the mass by 387 Da, which is consistent with the loss of cholesterol plus water (see Table 3). The mass of soluble Shh was not affected by base treatment. Together, these observations suggested that the membrane-tethered human Shh contained two modifications, a cholesterol and a second moiety with a mass of 236 Da The similarity in mass between this value and the mass of an added palmitoyl group (238 Da) suggested that the protein might be palmitoylated. More accurate estimates of the mass, discussed below, revealed a correlation within 0.1 Da of the predicted mass of a palmitoyl moiety.

TABLE 2

Characterization of tethered Shh by MS. Calculated mass values were determined using average residue masses in part a and monoisotopic protonated masses in part b.

| Protein | | Mass (Da) Calculated | Measured |
|---|---|---|---|
| a. KOH-treated Shh | | | |
| no tether | (−treatment) | 19560.02 | 19560 |
| no tether | (+treatment) | 19560.02 | 19561 |
| tethered | (−treatment) | 20167.14 | 20167 |
| tethered | (+treatment) | 19798.49 | 19780 |
| b. N-terminal endoproteinase Lys-C peptide (MH+)* | | | |
| no tether | | 983.49 | 983.50 |
| tethered | | 1221.72 | 1221.79 |

*All mass values for peptides described herein are protonated masses

Subsequently, we determined that tethered Shh could be fractionated into subspecies by HPLC with a modified elution gradient and we developed a simple HPLC assay for quantifying the various forms. Results from these analyses are shown in FIG. 3. In this assay, the unmodified Shh elutes first (peak 1), then cholesterol-modified Shh elutes (peak 2), and finally product containing both cholesterol and palmitic acid-modified Shh elutes (peak 3). The complex shape of peak 3 reflects the presence of a modified form of the palmitoyl group that was identified through sequencing by MALDI PSD measurement. The variant was 2 Da smaller than predicted and may therefore contain an unsaturated bond (data not shown).

Figure 4A:
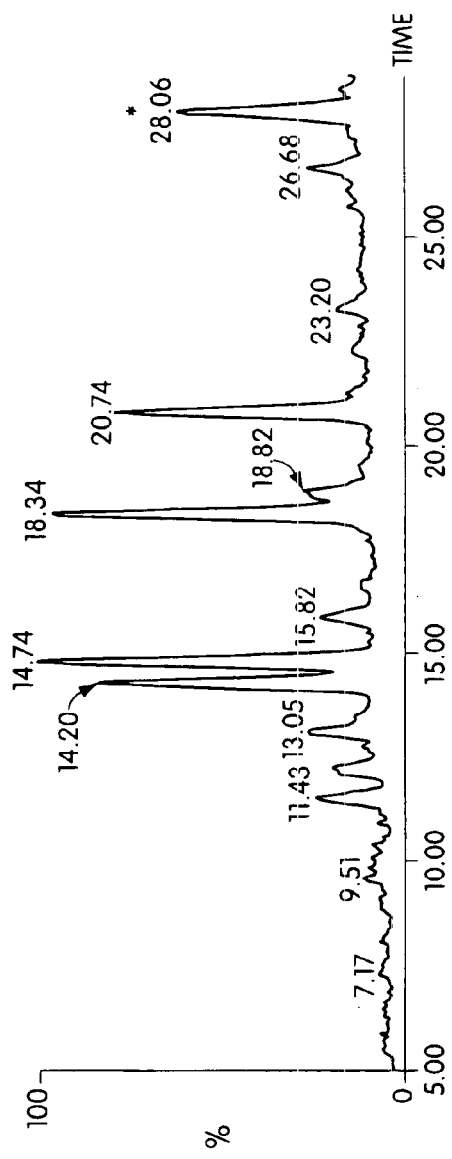
FIG. 4. Characterization of Shh by LC-MS. Tethered human Shh (A) and soluble human Shh (B) were alkylated with 4-vinylpyridine (1 μL/100 μL sample in 6 M guanidine HCl, 1 mM EDTA, 100 mM Tris HCl pH 8.0), ethanol precipitated, and digested with endoproteinase Lys-C in 50 mM Tris HCl pH 7.0, 2 M urea at an enzyme:protein ratio of 1:5 as described previously (27). The digests were analyzed by reverse phase HPLC in line with an electrospray Micromass Quattro II triple quadrupole mass spectrometer. Scans were acquired throughout the run and processed using the Micromass MassLynx data system (total ion chromatograms from the runs are shown). Asterisks indicate the positions of the N-terminal peptide which were verified either by MALDI PSD or N-terminal Edman sequencing.
Figure 4B:
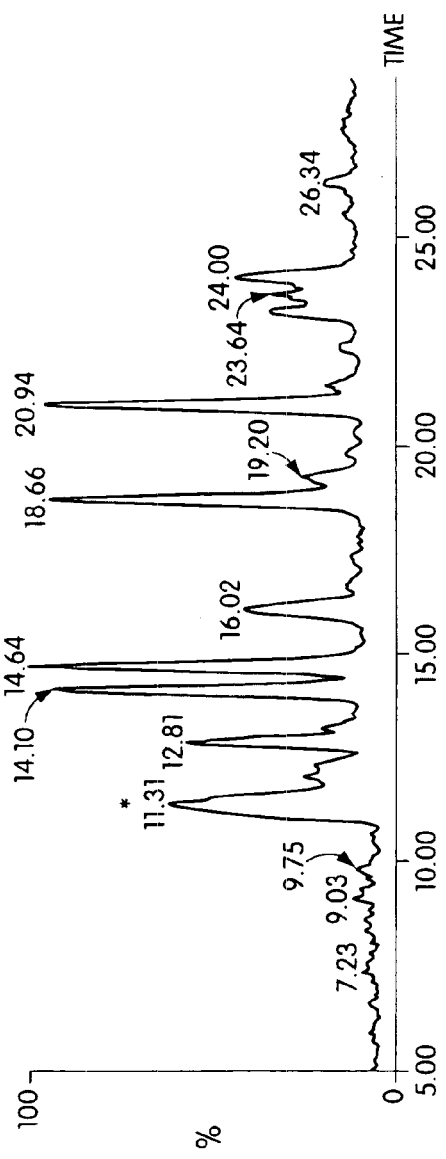

D. Localization of the Palmitic Acid Modification Within the Human Sonic Hedgehog Sequence The site of palmitoylation within the human sequence was identified using a combination of peptide mapping and sequence analysis. FIG. 4B shows results from a peptide mapping analysis of the soluble protein with an LC-MS readout. Mass data accounting for over 98% of the soluble Shh sequence could be accounted for from the analysis. The peak noted with an asterisk corresponds to the N-terminal peptide (residues 1–9 plus 4-vinylpyridine, observed mass 983.50 Da, calculated mass 983.49 Da; Table 2. In the corresponding analysis of the tethered product (FIG. 4A), this peptide was missing and instead a more hydrophobic peptide with mass of 1221.79 Da was observed (noted with asterisk).

Figure 5:
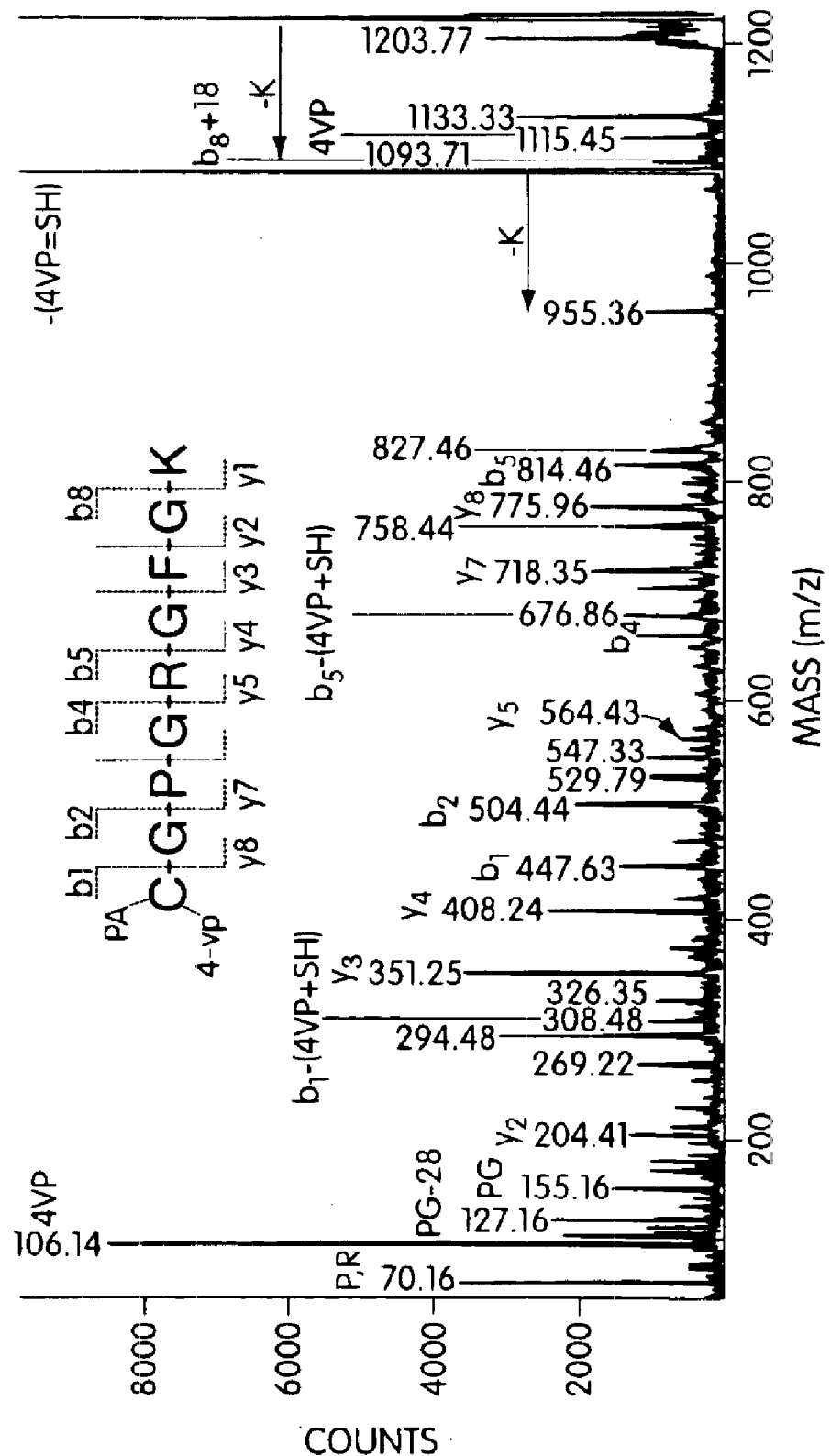
FIG. 5. Sequencing of the N-terminal Shh peptide by MALDI PSD measurement. The N-terminal endoproteinase Lys-C peptide from tethered human Shh was subjected to MALDI PSD measurement on a Voyager-DE™ STR time of flight mass spectrometer. The predicted fragmentation pattern and nomenclature for the detected fragment ions are shown at the top of the panel (PA, palmitoyl acid; 4vp, 4-pyridylethyl group). The remainder of the Figure shows the molecular mass spectrum produced by the run. Relevant ions are denoted using the nomenclature defined in the schematic. Calculated masses (Da) for $b_1$–$b_8$ are 447.3, 504.3, 601.4, 658.4, 814.5, 871.5, 1018.6, and 1075.6, respectively. For $y_1$–$y_8$, the masses (Da) are 147.1, 204.1, 351.2, 408.2, 564.3, 621.3, 718.4, and 775.4, respectively. The calculated mass for $z_8$ is 758.4 Da. The observed mass for $b_8$ contains an additional 18 Da due to an added water.

The 1221.79 Da moiety is consistent with the presence of a modified form of the N-terminal peptide, i.e. 983.49 Da for the peptide component plus 238.23 Da. The 1221.79 Da peptide was next subjected to sequence analysis by MALDI PSD measurement. The resulting PSD spectrum is shown in FIG. 5. Ions corresponding to b1, b2, b4, b5, b8+H$_2$O, y8, y7, y5, y4, y3, y2, and y1 fragments were detected which confirmed the sequence. In addition, the b1 and b2 ions indicated that the pyridylethylated Cys-1 adduct was palmitoylated. Only ions containing Cys-1, contained the added 238.23 Da mass.

Since cysteine is a normal site of palmitoylation for proteins in vivo, it was not surprising to find the novel adduct attached to the N-terminal cysteine. However, two pieces of evidence suggested that the lipid was attached to the amino group on the cysteine and not the thiol. First, in the peptide mapping study, we used 4-vinylpyridine as a spectroscopic tag to monitor free thiol groups (27). Pyridylethylation is highly specific for cysteine thiols and adds a 105 Da adduct that can be detected by MS. The observed Cys-1-containing fragments in the PSD spectrum contained both palmitoyl and pyridylethyl modifications, implying the presence of a free thiol group. Second, the tethered Shh was subjected to automated N-terminal Edman sequencing and no sequence was obtained, suggesting blockage at the N-terminal α-amine. By contrast, the corresponding soluble form of Shh can be sequenced readily.

EXAMPLE 2

Human Sonic Hedgehog can be Modified with Palmitic Acid in a Cell-Free System

Soluble Shh was labeled with $^3$H-palmitic acid in a cell-free system using a modified version of a published procedure (24). A crude microsomal fraction from rat liver was prepared by subjecting a liver homogenate to sequential centrifugation at 3000×g for 10 min, 9000×g for 20 min, and 100,000×g for 30 min. The 100,000×g pellet was suspended in 10 mM HEPES pH 7.4, 10% sucrose and again centrifuged at 100,000×g for 20 min. The final pellet (derived from 10 g of liver) was suspended in 3 mL of 20 mM Tris-HCl pH 7.4, 150 mM NaCl, 1 mM EDTA, 10 μg/mL leupeptin, 0.15% Triton X-100, aliquoted, and stored at −70° C. Reactions containing 3 μg Shh, 1 μL of rat microsomes, 50 ng/mL Coenzyme A (Sigma), 0.3 mM ATP, 20 mM Tris-HCl pH 7.4, 150 mM NaCl, 1 mM EDTA, 10 μg/mL leupeptin, and 0.5 μCi-[9,10-$^3$H]-palmitic acid (50 Ci/mmol; New England Nuclear) were performed at room temperature for 1 h. Reactions were stopped with reducing electrophoresis sample buffer, subjected to SDS-PAGE on a 10–20% gradient gel, and visualized by fluorography.

As shown in FIG. 1 (lane e), Shh is readily labeled with the radioactive tracer. None of the ca. hundred other proteins in the reaction mixture were labeled (see the corresponding Coomassie blue-stained gel profile in lane j), indicating a high degree of specificity of the palmitoylation reaction. As further evidence for the specificity of the palmitoylation reaction, we tested two Shh variants in which the site of palmitoylation had been eliminated. FIG. 1 (lane f) shows results from the analysis of a truncated form of soluble Shh that was lacking the first 10 amino acid residues of the mature sequence) and lane g, of a mutant form of Shh containing, at its N-terminal end, a single Cys-1 to Ser point mutation. Neither of the variants were labeled.

The significance of the N-terminal cysteine as the site of lipid derivatization is highlighted by the fact that wild type soluble Shh is readily labeled while the N-terminal cysteine to serine mutant is not. The inability to label the N-terminal serine mutant argues against a simple reaction mechanism where the palmitoyl moiety is directly attached to the N-terminal α-amine since under the test conditions the serine should have substituted for the cysteine.

We also tested the role of the free N-terminus using a form of soluble Shh with an N-terminal histidine (His)-tag extension. The soluble human Shh used in these studies had been produced initially as a His-tagged fusion protein with an enterokinase cleavage site at the junction of the mature sequence and was then processed with enterokinase to remove the His tag. The His-tagged Shh was not palmitoylated despite the presence of the free thiol group of the cysteine (See FIG. 1, lane i). While we cannot rule out the possibility that the N-terminal extension sterically inhibits palmitoylation from occurring, Cys-1 is at the P1' position of the enterokinase cleavage site and is readily accessible to enzymatic processing. Thus it appears that both the thiol and α-amine of Cys-1 contribute to the palmitoylation reaction. Since all known palmitoylation reactions target the side chains of Cys, Ser, or Thr residues, we infer that the modification on hedgehog starts with the formation of a thioester intermediate, and that the palmitoyl moiety is then transferred to the N-terminus through the formation of a cyclic intermediate. This hypothesis was confirmed during studies of the modification of human Sonic hedgehog using palmityol Coenzyme A (See Example 8).

EXAMPLE 3

Demonstration of Increased Potency of Naturally Ocurring Fatty-Acylated Human Sonic Hedgehog in a Cell-Based (C3H10T1/2) Assay Shh was tested for function in a cell-based assay measuring alkaline phosphatase induction in C3H10T1/2 cells (25) with a 5 day readout. The assay was preformed in a 96-well format. Samples were run in duplicate. For tethered Shh (100 µg/mL), the samples were first diluted 200-fold with normal growth medium then subjected to serial 2-fold dilutions down the plates. Wells were normalized for potential effects of the added octylglucoside by including 0.005% octylglucoside in the culture medium. Blocking studies using the neutralizing murine mAb 5E1 (26) were performed by mixing Shh with serial dilutions of the antibody for 30 min at ambient temperature in culture medium prior to adding the test samples to the plates.

Figure 6A:
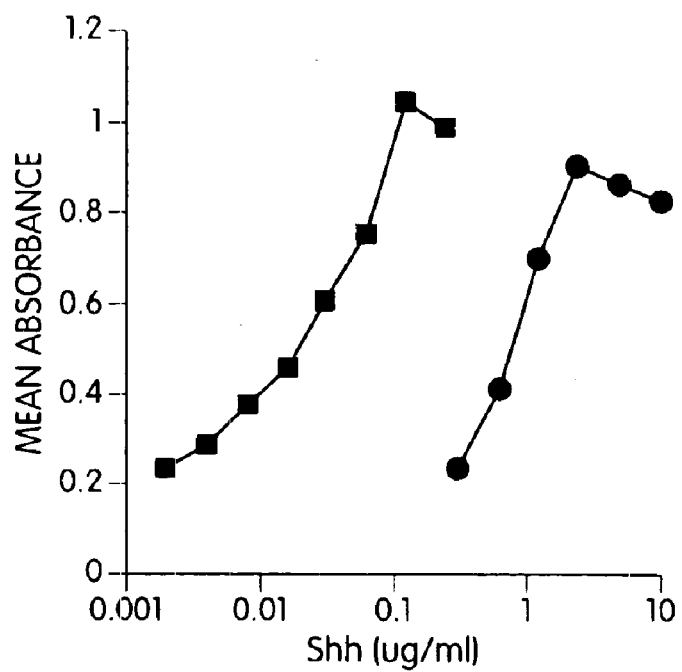
FIG. 6. Increased activity of tethered Shh in the C3H10T1/2 assay. The relative potencies of soluble and tethered human Shh alone (A) or in the presence of the anti-hedgehog neutralizing Mab 5E1 (B) were assessed on C3H10T1/2 cells measuring alkaline phosphatase induction. The numbers presented reflect the averages of duplicate determinations. (A) Serial 2-fold dilutions of soluble (6) and tethered (8) Shh were incubated with the cells for 5 days and the resulting levels of alkaline phosphatase activity measured at 405 nm using the alkaline phosphatase chromogenic substrate p-nitrophenyl phosphate. (B) Serial dilutions of Mab 5E1 were incubated with soluble Shh (5 μg/mL: black bars) or tethered Shh (0.25 μg/mL: gray bars) or vehicle control without Shh added (white bar) for 30 min and then subjected to analysis in the C3HT101/2 assay.
Figure 6B:
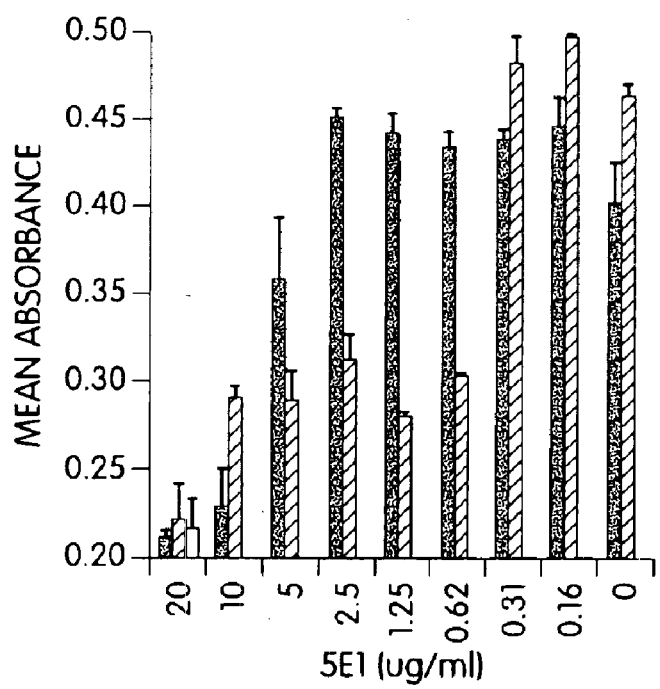

In this assay, soluble human Shh produces a dose-dependent response with an $IC_{50}$ of 1 µg/mL and a maximal signal at 3 µg/mL (FIG. 6A). Tethered human Shh, with a cholesterol attached at the C-terminus and a palmitoyl group at the N-terminus, similarly produced a dose-dependent response in the assay but with an $IC_{50}$ of 0.03 µg/mL and a maximal signal at 0.1 µg/mL, indicating that it was about 30 times as potent as soluble Shh. To verify that the observed activity was hedgehog specific, we tested whether the activity could be inhibited with the anti-hedgehog neutralizing mAb 5E1. Both soluble and tethered Shh were inhibited by 5E1 treatment (FIG. 6B). Inhibition of the tethered Shh required a tenth as much 5E1 consistent with its increased activity in the assay.

Tethered Shh was tested in a receptor binding assay, monitoring its ability to bind patched, using a modified version of a recently published assay (10). The tethered Shh showed dose-dependent binding to cells expressing patched with an apparent $IC_{50}$ of 400 ng/mL (FIG. 7). In the same assay, soluble Shh bound to patched with an apparent $IC_{50}$ of 150 ng/mL, indicating that the tethered form bound only slightly less tightly to its receptor.

EXAMPLE 4

Analysis of Tethered Human Sonic Hedgehog after Reconstitution into Liposomes

This example illustrates that reconstitution experiments into positively and negatively charged liposomes by detergent dilution over a wide range of lipid:protein ratios (w/w) from 1:1 to 100:1 had no effect on tethered Shh activity in the C3H10T1/2 assay.

Reconstitution into phospholipid containing liposomes provides a useful formulation for lipid-containing proteins because it allows a lipid-containing protein to exist in a near normal setting. To test whether such a formulation was viable for tethered Shh we utilized a detergent dilution method to incorporate the protein into a liposome (60), where preformed liposomes are mixed with octylglucoside and the protein of interest, and then the detergent is diluted below its critical micelle concentration, thus driving the reconstitution. While any of a large number of pure or lipid mixtures can be utilized, we selected two commercially available mixtures as models; a negatively charged liposome kit containing egg L-α-phosphatidylcholine, dicetyl phosphate, and cholesterol (Cat. No. L-4262; Sigma, St. Louis, Mo.), and a positively charged liposome kit consisting of egg phosphatidyl choline, stearlyamine, and cholesterol (Cat. No L-4137, Sigma).

Briefly, the lipids were transferred into a Pyrex tube, dried under a stream of nitrogen, and residual solvent removed by lyophilization. The lipid was suspended in 10 mM HEPES pH 7.5, 100 mM NaCl, 2.0% octylglucoside, vortexed, and sonicated until the suspension had turned opalescent in appearance. The lipid was then filtered through a 0.2 micron filter. Aliquots of tethered Shh, from baculovirus-infected High Five™ insect cells, in octylglucoside were treated with a 400-, 1000-, 5000-, and a 20000-fold excess of lipid (w/w) and after a 15 min preincubation the samples were diluted and assayed for activity in the C3H10T1/2 assay.

Neither the positive nor the negative liposome treatment had any affect on the activity of the hedgehog indicating that a lipid carrier was a viable formulation. To verify that the hedgehog indeed had become reconstituted, parallel samples were subjected to centrifugation under conditions where the tethered Shh would normally pellet and the liposomes would float to the surface of the sample. Under these conditions the tethered Shh floated to the surface, indicating that reconstitution had occurred.

EXAMPLE 5

Characterization of Membrane-Tethered Human Sonic Hedgehog from Mammalian (EBNA-293) Cells In order to assess whether palmitoylation was a general modification pathway for Sonic hedgehog or whether it was specific to insect cell production, the protein was also produced in a mammalian system in EBNA-293 cells. For expression of full-length Shh in mammalian cells, the 1.4 kb NotI fragment containing full-length Shh (See Example 1) was cloned into a derivative of the vector, CH269 pCEP4 (Invitrogen, San Diego, Calif. (21)). The construct was transfected into EBNA-293 cells using lipofectamine (Life Technologies, Inc.) and the cells were harvested 48 h post-transfection. The expression of surface Shh was verified by FACS and by Western blot analysis.

Tethered Shh from EBNA-293 cells was fractionated by reverse phase HPLC on a narrow bore $C_4$ column (See FIG. 3). Peaks were analyzed by ESI-MS (parts a and b of Table 3) or by MALDI-TOF MS on a Finnigan LaserMat mass spectrometer using β-cyano-4-hydroxycinnamic acid as the matrix (part c of Table 3. By SDS-PAGE, the protein migrated slightly faster than soluble Shh, it was retarded on the $C_4$ column in the reverse phase HPLC analysis, and, by mass spectrometry, it contained an ion corresponding to the palmitic acid plus cholesterol modification. However, unlike the insect cell-derived product where over 80% of the product contained both the palmitic acid and cholesterol modification, the HPLC elution profile and data from mass spectrometry revealed that most of the mammalian cell-derived protein lacked the palmitoyl moiety (see Table and FIG. 3C). That is, in peak 2 from EBNA-293 cells the ratio of clipped (des-1-10) versus intact protein by MS signal was 50% whereas for peak 1 only about 10% of the Shh was clipped. Interestingly, both the insect cell and mammalian cell-derived products showed comparable activity in the C3H10T1/2 assay suggesting that both the cholesterol, and the cholesterol plus palmitic acid modifications are functional. Whether the second lipid attachment site is used simply to further stabilize the association of the protein with membrane or whether it plays a more active role and affects its conformation or protein-protein contacts remains to be determined.

Fatty acid derivatization of proteins is a common post translational modification that occurs late in the maturation processes (28,29). For cysteine derivatives, the process is dynamic involving separate enzymes that add and remove the modification on the sulfhydryl group. The most common functions of such derivatization (e.g., palmitoylation) are to alter the physico-chemical properties of the protein, i.e., to target a protein to its site of function, to promote protein-protein interactions, and to mediate protein-membrane interactions (30). For hedgehog, while the difference in the extent of palmitoylation in the insect and mammalian cell-derived preparations (80% in insect cells versus 30% in mammalian cells) was surprising, we do not know if it is biologically significant or whether it simply reflects differences in the cellular machinery of the two test systems for adding and removing palmitic acid. The difference in the extent of modification in the insect and mammalian cells is unlikely to be species related since tethered *Drosophila* hedgehog that was produced in insect cells lacked palmitic acid (19) despite having the identical N-terminal sequence.

TABLE 3

Mass spectrometry analysis of EBNA-293-derived tethered human Sonic hedgehog.

| Protein | Mass (Da) | |
| --- | --- | --- |
|  | Calculated | Measured |
| a. bacterial expressed (no tether) | 19560.02 | 19560 |
| b. baculovirus expressed (tethered) | | |
| +palmitic acid | 19798.49 | 19796 |
| +palmitic acid/cholesterol | 20167.14 | 20168 |
| c. EBNA-293 cell expressed (tethered) | | |
| peak 1 (9% of total hedgehog) | | |
| no tether | 19560.02 | 19581 |
| no tether (des 1–9) | 18700.02 | 18712 |
| peak 2 (61% of total hedgehog) | | |
| +cholesterol | 19928.67 | 19934 |
| +cholesterol (des 1–10) | 18912.48 | 18889 |
| peak 3 (30% of total hedgehog) | | |
| +palmitoyl/cholesterol | 20167.14 | 20174 |

EXAMPLE 6

Lipid Modifications of Rat Sonic Hedgehog

This Example illustrates that a variety of lipids become linked to a soluble version of rat Sonic hedgehog when the rat Shh gene encoding residues 1–174 is expressed in High Five™ insect cells, essentially as for the full-length human Shh described in Example 1. The lipid modification renders this fraction membrane-associated. The N-terminal fragment (residues 1–174 of unprocessed rat Sonic hedgehog) differs by only 2 amino acid residues to that of the N-terminal fragment of human Sonic hedgehog. In the rat Sonic hedgehog N-terminal fragment, threonine replaces serine at position 44, and aspartic acid replaces glycine at position 173. When rat Sonic hedgehog lacking the autoprocessing domain is expressed in the High-Five™ insect cell/baculovirus expression system, the majority of the protein is secreted into the culture medium since it lacks the ability to attach a cholesterol moiety to the C-terminus. This soluble form has a specific biological activity (measured by the C3H10T1/2 alkaline phosphatase induction assay of Example 3) that was similar to that of the soluble, N-terminal fragment of human Sonic hedgehog expressed and purified from *E. coli*.

However, a small fraction of the total protein remains associated with the insect cells. The cell-associated rat Sonic hedgehog protein was purified essentially as described in Example 1, and was found to be significantly more active in the alkaline phosphatase assay (data not presented) than the soluble, N-terminal fragments of either human or rat Sonic hedgehog purified from *E. coli* and the High-Five™ insect cell/baculovirus expression system, respectively. Subsequent analyses of the rat Sonic hedgehog N-terminal fragments by HPLC and electrospray mass spectrometry (as described in Example 1) suggests that the protein is lipid-modified and that there was more than one type of lipid modification. Supporting evidence includes the following observations:

1. The cell-associated forms elute later than the soluble, N-terminal fragments of human and rat sonic hedgehog from a $C_4$ reverse phase HPLC column (Vydac catalog number 214TP104) developed with a linear 30 min 0–70% acetonitrile gradient in 0.1% trifluoroacetic acid;

2. The masses of the cell-associated forms are consistent with that expected for the lipid-modified proteins, as shown in Table 4.

TABLE 4

Masses of various lipid-modified forms of rat Sonic hedgehog.

| Protein | Adduct | Expected Mass* ($MH^+$) | Observed Mass ($MH^+$) |
| --- | --- | --- | --- |
| unmodified | none | 19,632.08 | 19,632 |
| myristoyl- | $CH_3(CH_2)_{12}CO-$ | 19,842.50 | 19,841 |
| palmitoyl- | $CH_3(CH_2)_{14}CO-$ | 19,870.55 | 19,868 |
| stearol- | $CH_3(CH_2)_{16}CO-$ | 19,898.60 | 19,896 |
| arachidoyl- | $CH_3(CH_2)_{18}CO-$ | 19,926.66 | 19,925 |

*Average masses were used in calculating the expected masses

The location of the lipid moiety was determined using a combination of sequence analysis and peptide mapping. Automated N-terminal Edman sequencing of the lipid-modified forms indicated that the N-terminus was blocked, suggesting that the lipid was attached to the α-amine of the N-terminal cysteine. Endo-Lys-C peptide mapping, MALDI-TOF mass spectrometry and MALDI PSD analysis (as described in Example 1) of the 4-vinylpyridine alkylated lipid-modified forms, were used to confirm the location of the lipid modifications and to determine their exact masses.

The masses of the N-terminal peptides (residues 1–9 inclusive plus 4-vinylpyridine attached to the thiol side chain of the N-terminal cysteine) carrying the lipid modifications were consistent within 0.1 Da with that expected for the lipid-modified peptides as shown in Table 5.

TABLE 5

Masses of the N-terminal peptides isolated from various lipid-modified forms of rat Sonic hedgehog.

| Protein | Adduct | Expected Mass* (MH$^+$) | Observed Mass (MH$^+$) |
| --- | --- | --- | --- |
| myristoyl- | CH$_3$(CH$_2$)$_{12}$CO— | 1193.69 | 1193.76 |
| palmitoyl- | CH$_3$(CH$_2$)$_{14}$CO— | 1221.72 | 1221.65 |
| stearoyl- | CH$_3$(CH$_2$)$_{16}$CO— | 1249.75 | 1249.71 |

*Monoisotopic masses were used in calculating the expected masses

In addition to the lipid-modified peptides shown in Table 5, peptides with masses of 1191.74, 1219.84 and 1247.82 were also detected. These masses are consistent with unsaturated forms of myristate, palmitate and stearate, respectively, although the position of the double bond in the alkyl chain was not determined. These observations indicate that both saturated and unsaturated fatty acids can be attached covalently to the N-terminal cysteine. For both the saturated and unsaturated lipid-modified peptides, MALDI PSD analysis as described in Example 1 confirmed that the lipids were attached covalently to the N-terminal cysteine residue.

EXAMPLE 7

Lipid Modification of Indian Hedgehog

To assess whether the palmitoylation reaction was unique to human Shh or whether it might occur on other hedgehog proteins, we tested whether human Indian hedgehog (expressed in *E. coli* as a His-tagged fusion protein with an enterokinase cleavage site immediately adjacent to the start of the mature sequence, and purified exactly as for recombinant human Sonic hedgehog (See Example 9)) could be palmitoylated using the assay described in Example 2. Human Indian hedgehog was modified (See FIG. 1, lane h), indicating that palmitoylation is likely to be a common feature of hedgehog proteins. The ability to directly label Shh and Ihh with radioactive palmitic acid in a cell-free system provided a simple screen for amino acids involved in the modification reaction. Moreover, Indian hedgehog palmitoylated by the method described in Example 8 was significantly more potent in the C3H10T1/2 assay than the unmodified Ihh.

EXAMPLE 8

Lipid Modifications of Sonic Hedgehog using Acyl-Coenzyme A

The in vitro acylation of a protein containing an N-terminal cysteine can be accomplished via a two-step, chemical reaction with a fatty acid-thioester donor. In the first step, the acyl group of the thioester donor transfers to the sulfhydryl of the N-terminal cysteine on the protein by a spontaneous transesterification reaction. Subsequently, the acyl moiety undergoes a S to N shift to the 1-amine of the N-terminal cysteine to form a stable amide bond. Direct acylation of an amine function on a protein may also occur with prolonged incubation with a thioester, but the presence of a cysteine on the protein will accelerate the reaction and allow control over the acylation site. In the present examples, commercially available Coenzyme A derivatives (Sigma Chemical Company, St. Louis Mo.) are utilized, but other thioester groups would also achieve the same result. In fact, certain thioester leaving groups, such as thiobenzyl esters, would be expected to react more rapidly. Internal cysteine residues may also promote acylation to neighboring lysines (i.e., as in an internal cysteine-lysine pair) and this can be conveniently tested using synthetic peptides. Secondary acylations occuring on a protein during reaction with thioesters may be prevented by controlling the buffer composition, pH, or by site-directed mutagenesis of the neighboring lysines.

In preliminary analysis of the effect of acylation on the ability of human Sonic hedgehog to induce alkaline phosphatase in C3H10T1/2 cells, reaction mixtures contained 1 mg/mL human Sonic hedgehog (51 $\mu$M), 500 $\mu$M of the particular, commercially available, acyl-Coenzyme A (compounds tested included acetyl-CoA (C2:0), butyryl-CoA (C4:0), hexanoyl-CoA (C6:0), octanoyl-CoA (C8:0), decanoyl-CoA (C10:0), lauroyl-CoA (C12:0), myristoyl-CoA (C14:0), palmitoyl-CoA (C16:0), palmitoleoyl-CoA (C16:1), stearoyl-CoA (C18:0), arachidoyl-CoA (C20:0), behenoyl-CoA (C22:0), lignoceroyl-CoA (C24:0), succinyl-CoA, and benzoyl-CoA), 25 mM DTT, and 50 mM Na$_2$HPO$_4$ pH 7.0. The reactions were incubated at room temperature for 3 h and then analyzed immediately (without purification) for bioactivity in the C3H10T1/2 assay as described in Example 3. Samples for analysis by reverse phase HPLC and other physical methods were usually stored at $-70°$ C. HPLC analysis was carried out on a Vydac C$_4$ reverse phase column (4.6 mm internal diameter$\times$250 mm, 5 micron particle) with a 40 min gradient of 5% acetonitrile to 85% acetonitrile in aqueous 0.1% TFA, at a flow rate of 1 mL/min. The effluent was monitored at 280 nm, and fractions were collected in some experiments and analyzed for hedgehog protein on SDS-PAGE with detection by Coomassie staining and by Western blotting.

Comparison of the activity of the various reaction mixtures (FIG. 10) indicates that a chain length of between 12 and 18 carbons is optimal in inducing high alkaline phosphatase activity as compared to the unmodified protein. Increasing the chain length further resulted in an apparent reduction in activity, and the presence of a double bond in the unsaturated palmitoleoyl-CoA (C16:1) gave the same activity as the fully saturated palmitoyl-CoA (C16:0). Upon reverse phase HPLC analysis of the reaction mixtures, we observed that many of the shorter chain length acyl-CoA derivatives had not reacted with the hedgehog protein, and therefore the dependence of biological activity shown in FIG. 10 was not a true reflection of the acyl chain length.

In order to obtain data on the true activity of the modified proteins, and on the dependence of activity on acyl chain length, we developed methods for the synthesis and purification of the individual N-terminal acylated forms. Palmitoylated, myristoylated, lauroylated, decanoylated, and octanoylated human Sonic hedgehog proteins, carrying a single acyl chain attached to the $\alpha$-amine of the N-terminal cysteine, were produced in reaction mixtures containing 0.80 mg/mL (41 $\mu$M) human Sonic hedgehog, 410 $\mu$M (10-fold Molar excess) of either palmitoyl-CoA, myristoyl-CoA, or lauroyl-CoA, or 4.1 mM (100-fold Molar excess) of either decanoyl-CoA or octanoyl-CoA, 25 mM DTT (for reaction mixtures containing palmitoyl-CoA, myristoyl-CoA, or lauroyl-CoA) or 0.5 mM DTT (for reaction mixtures containing decanoyl-CoA or octanoyl-CoA), and 40 mM Na$_2$HPO$_4$ pH 7.0. Reaction mixtures were incubated at 28° C. for 24 h. Reaction of the N-terminal cysteine with the acyl thioesters results in the transfer of the acyl group to the sulfhydryl by a spontaneous transesterification reaction, which is followed by a S to N shift to the $\alpha$-amine to form a stable amide linkage. The free sulfhydryl then undergoes a second transesterification reaction, yielding a protein with a fatty acyl group attached via a thioester linkage to the sulfhydryl. The thioester-linked acyl group was removed by adding consecutive 0.11 volume of 1 M $Na_2HPO_4$ pH 9.0, and 0.11 volume of 1 M hydroxylamine (0.1 M final concentration) followed by incubation at 28° C. for 18 h, which leaves only the acyl amide attached to the protein (62). 0.25 volume of 5% octylglucoside was then added (1% final concentration) and the mixture incubated for 1 h at room temperature. The proteins were then purified in the presence of 1% octylglucoside using SP-Sepharose Fast Flow (Pharmacia) and Bio Scale S (Biorad) cationic ion exchange chromatographies. The purified proteins were dialyzed against 5 mM $Na_2HPO_4$ pH 5.5, 150 mM NaCl, 1% octylglucoside, 0.5 mM DTT, and were stored at −70° C. The presence of octylglucoside was required to maintain full solubility; removal of the detergent by dilution and dialysis resulted in a 75%, 41%, and 15% loss of the palmitoylated, myristoylated, and lauroylated proteins, respectively. ESI-MS of the HPLC-purified proteins confirmed their integrity: palmitoylated Sonic hedgehog, measured mass=19798, calculated mass=19798.43; myristoylated Sonic hedgehog, measured mass=19770, calculated mass=19770.33; lauroylated Sonic hedgehog, measured mass=19742, calculated mass=19742.33; decanoylated Sonic hedgehog, measured mass=19715, calculated mass=19714.28; octanoylated Sonic hedgehog, measured mass=19686, calculated mass=19686.23.

Analysis of the various acylated forms of human Sonic hedgehog in the C3H10T1/2 assay (FIG. 11) indicated that the activity of the proteins was dependent upon the chain length. The palmitoylated, myristoylated, and lauroylated proteins showed approximately equal activity with $EC_{50}$ values of 5–10 ng/mL (100–200-fold increase in potency as compared to the unmodified protein). Decanoylated human Sonic hedgehog, with an $EC_{50}$ value of 60–70 ng/mL (15–30-fold increase in potency as compared to the unmodified protein), was less active than the palmitoylated, myristoylated, and lauroylated forms, while the octanoylated form was the least active with an $EC_{50}$ of 100–200 ng/mL (10-fold increase in potency as compared to the unmodified protein). All of the acylated forms were more potent than the unmodified protein which had an $EC_{50}$ of 1000–2000 ng/mL. In addition to the decrease in $EC_{50}$, the palmitoylated, myristoylated, and lauroylated proteins induced approximately 2-fold more alkaline phosphatase activity than the unmodified protein, while the decanoylated and octanoylated proteins induced approximately 1.5-fold more.

In addition to the increase in potency of the myristoylated form of human Sonic hedgehog observed in the C3H10T1/2 assay, this form is significantly more potent than the unmodified protein at inducing ventral forebrain neurons in explants of embryonic stage E11 rat brain telencephalon. Incubation of E11 telencephalic explants with various concentrations of unmodified, or myristoylated Sonic hedgehog, and subsequent staining of the explants for the products of the dlx and islet-1/2 genes (markers of ventral forebrain neurons), indicates that while induction by the unmodified protein is observed first at 48 nM, induction by the myristoylated form is observed first at 3 nM. Moreover, while the unmodified protein induces restricted expression at 3070 nM, the myristoylated protein induces widespread expression at only 48 nM. A similar increase in potency was observed when explants of embryonic stage E9 presumptive telencephalon were incubated with either the unmodified, or myristoylated proteins. Staining of the explants for the product of the Nkx2.1 gene (an early marker of ventral forebrain neurons), indicated that the unmodified protein induced Nkx2.1 first at 384 nM, while for the myristoylated protein expression of Nkx2.1 was observed first at 12 nM. Moreover, at 48 nM myristoylated Sonic hedgehog, expression of Nkx2.1 was widespread while it was undetectable at this concentration using the unmodified form.

Additionally, myristoylated human Sonic hedgehog has been shown to be significantly more protective than the unmodified protein in reducing the lesion volume which results from administration of malonate into the striatum of the rat brain (See Example 16).

EXAMPLE 9

Chemical Derivatives of the N-terminal Cysteine of Human Sonic Hedgehog

A. General Methods

Alkylation of Proteins. Samples containing about 20 µg of the protein in 50 µL of 6 M guanidine hydrochloride, 50 mM $Na_2HPO_4$ pH 7.0, were treated with 0.5 µL of 4-vinylpyridine for 2 h at room temperature. The S-pyridylethylated protein was precipitated by addition of 40 volumes of cooled ethanol. The solution was stored at −20° C. for 1 h and then centrifuged at 14,000×g for 8 min at 4° C. The supernatants were discarded and the precipitate was washed with cooled ethanol. The protein was stored at −20° C.

Peptide Mapping. Alkylated protein (0.4 mg/mL in 1 M guanidine hydrochloride, 20 mM $Na_2HPO_4$ pH 6.0) was digested with endo Lys-C (Wako Pure Chemical Industries, Ltd.) at a 1:20 ratio. The digestion was conducted at room temperature for 30 h. The reaction was stopped by acidification with 5 µL of 25% trifluoroacetic acid. The digest was analyzed on a Waters 2690 Separation Module with a Model 996 photodiode array detector. Prior to injection, solid guanidine hydrochloride was added into the digest to a concentration of 6 M to dissolve insoluble material. A reverse phase Vydac $C_{18}$ (2.1 mm internal diameter×250 mm) column was used for separation, with a 90 min gradient of 0.1% trifluoroacetic acid/acetonitrile and 0.1% trifluoroacetic acid/acetonitrile at a flow rate of 0.2 mL/min. Individual peaks were collected manually for mass analysis.

Mass Determination. The molecular masses of intact proteins were determined by electrospray ionization mass spectroscopy (ESI-MS) on a Micromass Quattro II triple quadrupole mass spectrometer. Samples were desalted using an on-line Michrom Ultrafast Microprotein Analyzer system with a Reliasil $C_4$ (1 mm internal diameter×50 mm) column. The flow rate was 20 µL/min. All electrospray mass spectral data were processed using the Micromass MassLynx data system. The molecular masses of peptides were determined by matrix assisted laser desorption ionization time-of-fight mass spectrometry (MALDI-TOF-MS) on a Voyager-DE™ STR (PerSeptive Biosystems, Framingham, Mass.). Sequencing of the modified peptide was performed by Post-source decay (PSD) measurement on the same instrument. α-Cyano-4-hydroxycinnamic acid was used as the matrix.

N-terminal Sequencing. Proteins were sequenced by Edman degradation on a Perkin-Elmer Applied Biosystems model 477A Pulsed-Liquid Protein Sequencer. PTH-thiaproline was made on line by directly loading thiaproline (thiazolidine-4-carboxylic acid) into the sample loading cartridge of the sequencer.

Bacterial expression and purification of wild type soluble human Sonic hedgehog N-terminal fragment used for chemical modification. Bacterial pellets from cells expressing Shh at 4–5% of the total protein were thawed, resuspended in lysis buffer (25 mM Na$_2$HPO$_4$ pH 8, 150 mM NaCl, 1 mM EDTA, 1 mM PMSF, 0.5 mM DTT) at a ratio of 1:4 (w/v) and lysed by two passes through a Gaulin press (mfg. by APV Rannie, Copenhagen, Denmark) at 12,000 p.s.i. All subsequent purification steps were performed at 2–8° C. unless indicated otherwise. The homogenate was centrifuged at 19,000×g for 60 min and MES 0.5 M pH 5, was added to the resulting lysate at a ratio of 1:10 (v/v). The lysate (at pH 5.5) was loaded onto an SP Sepharose Fast Flow (Pharmacia, Piscataway, N.J.) column (4 g *E. coli* wet weight/mL resin) equilibrated with 25 mM Na$_2$HPO$_4$ pH 5.5, 150 mM NaCl. The column was washed with 4 column volumes (CV) of equilibration buffer, then with 3 CV of 25 mM Na$_2$HPO$_4$ pH 5.5, 200 mM NaCl, 0.5 mM DTT, and Histag-Shh was eluted with 800 mM NaCl in the same buffer. Elution fractions were analyzed for absorbance at 280 nm and by SDS-PAGE. Imidazole (1M stock solution at pH 7) and NaCl (5 M stock solution) were added to a pool of the peak Shh containing fractions from the SP Sepharose eluate to give final concentrations of 20 mM and 1 M respectively, and this material was loaded onto a NTA-Ni agarose (Qiagen, Santa Clara, Calif.) column (20 mg/mL resin) equilibrated with 25 mM Na$_2$HPO$_4$ pH 8, 1 M NaCl, 20 mM imidazole, 0.5 mM DTT. The column was washed with 5 CV of the same buffer and Histag-Shh eluted with 3 CV 25 mM Na$_2$HPO$_4$ pH 8, 1 M NaCl, 200 mM imidazole, 0.5 mM DTT. The protein content in the eluate pool from the NTA-Ni column was determined by absorbance at 280 nm. The pool was warmed to room temperature and an equal volume of 2.5 M sodium sulfate was added. The Phenyl Sepharose step was performed at room temperature. The material was loaded onto a Phenyl Sepharose Fast Flow (Pharmacia, Piscataway, N.J.) column (20 mg/mL resin) equilibrated in 25 mM Na$_2$HPO$_4$ pH 8, 400 mM NaCl, 1.25 M sodium sulfate, 0.5 mM DTT. Histag-Shh was eluted with 25 mM Na$_2$HPO$_4$ pH 8, 400 mM NaCl, 0.5 mM DTT. Typically, we recovered 2–3 g of His-tagged Shh from 0.5 kg of bacterial paste (wet weight). The product was filtered through 0.2 μm filter, aliquoted, and stored at −70° C. The His-tagged Shh was about 95% pure as determined by SDS-PAGE. As a further assessment of the characteristics of the purified product, samples were subjected to evaluation by electrospray ionization mass spectrometry (ESI-MS). Approximately 50% of the protein was missing the N-terminal methionine.

To cleave off the hexahistidine tag, enterokinase (Biozyme, San Diego, Calif.) was incubated with the Histag-Shh at an enzyme: Shh ratio of 1:1000 (w/w) for 2 h at 28° C. Uncleaved Histag-Shh and free Histag were removed by passing the digest through a second NTA-Ni agarose column (20 mg Shh/mL resin). Prior to loading, imidazole (1 M stock solution at pH 7) and NaCl (5M stock solution) were added to the digest to give final concentrations of 20 mM and 600 mM, respectively. This material was loaded onto a NTA-Ni column equilibrated in 25 nM Na$_2$HPO$_4$ pH 8, 600 mM NaCl, 20 mM imidazole, 0.5 mM DTT and the flow through collected. The column was washed with 1 CV of the same buffer and pooled with the flow through. MES (0.5 M stock solution at pH 5) was added to the NTA-Ni agarose unbound fraction to a final concentration of 50 mM and two volumes of water were added. This material was loaded onto a second SP Sepharose Fast Flow column (20 mg/mL resin) equilibrated with 5 mM Na$_2$HPO$_4$ pH 5.5, 150 mM NaCl, 0.5 mM DTT. The column was washed with 3 CV of equilibration buffer and 1 CV of the same buffer containing 300 mM NaCl. Shh was eluted with 5 mM Na$_2$HPO$_4$ pH 5.5, 800 mM NaCl, 0.5 mM DTT. Atomic absorption data revealed that Shh at this stage contained 0.5 mol equivalent of Zn$^{2+}$. An equimolar concentration of ZnCl$_2$ was added to the Shh eluant and the protein dialyzed against 5 mM Na$_2$HPO$_4$ pH 5.5, 150 mM NaCl, 0.5 mM DTT. The resulting Shh was >98% pure as characterized by SDS-PAGE, size exclusion chromatography (SEC), and ESI-MS and, by atomic absorption, contained between 0.9 and 1.1 Zn$^{2+}$/Shh.

ESI-MS data for Histag Shh and products resulting after removal of the histag are summarized in Table 6.

TABLE 6

Characterization of Shh by ESI-MS.

| Protein | | Mass (Da) | |
| --- | --- | --- | --- |
| | | Calculated | Measured |
| Histag-Shh | (-Met) | 21433.82 | 21434 |
| | (Intact) | 21565.01 | 21565 |
| Enterokinase-cleaved Shh | | 19560.02 | 19560 |

B. Specific Chemical Modifications

Modification of human Sonic hedgehog with N-ethylmaleimide. Purified Shh in 5 mM Na$_2$HPO$_4$ pH 5.5, 150 mM NaCl, 0.5 mM DTT was treated with 10 mM N-ethylmaleimide for 1 h on ice and then dialyzed into 5 mM Na$_2$HPO$_4$ pH 5.5, 150 mM NaCl. The MALDI-TOF-MS data showed that the N-ethylmaleimide (NEM)-modified protein had an increase in mass of 126 Da, which indicates that only one cysteine residue in Shh was modified by the reagent. N-terminal sequencing data showed that the protein is sequencible and that an unusual peak, probably PTH-NEM-Cys related, was detected at the first cycle (data not shown). Mass spectrometric analysis of the pyridylethylated-NEM-Shh under denaturing conditions showed that only two cysteine residues in the protein were alkylated, confirming that only the thiol group of the N-terminal cysteine residue was modified by NEM under native conditions (Table 7. The other two cysteine residues, which are apparently buried in the hydrophobic core of the protein, cannot be modified without prior denaturation.

TABLE 7

Characterization of NEM-modified Shh by MS.

| Protein | Mass (Calculated) | Mass (Measured) |
| --- | --- | --- |
| Pyridylethylated NEM Shh | | 19895 Da |
| if containing 2 free Cys residues | 19895 Da | |
| if containing 3 free Cys residues | 20000 Da | |

When tested in the C3H10T1/2 assay (See Example 3) the N-ethylmaleimide-modified hedgehog protein was equal in activity to the unmodified protein. This demonstrates that a free sulfhydryl at the N-terminus of hedgehog is not required for activity and that the N-ethylmaleimide moiety is hydrophobic enough to confer some activity on hedgehog compared to other more hydrophilic modifications, such as conversion of Cys-1 to His or Asp, which produce a reduction in activity.

Modification of human Sonic hedgehog with formaldehyde to form an N-terminal thiaproline, and with acetaldehyde and butyraldehyde to form N-terminal thiaproline derivatives. For formaldehyde modification, purified Shh at 3 mg/mL in 5 mM Na$_2$HPO$_4$ pH 5.5, 150 mM NaCl, 0.5 mM DTT was treated with 0.1% formaldehyde, with or without 10% methanol, at room temperature for 1 to 6 h. The protein was either dialyzed against 5 mM $Na_2HPO_4$ pH 5.5, 150 mM NaCl, or was purified on a CM-Poros column (Perseptive Biosystems) as described below and then dilayzed against 5 mM $Na_2HPO_4$ pH 5.5, 150 mM NaCl. For modification with acetaldehyde or butyraldehyde, purified Shh at 3 mg/mL in 5 mM $Na_2HPO_4$ pH 5.5, 150 mM NaCl, 0.5 mM DTT was treated with 0.1% acetaldehyde or butyraldehyde at room temperature for 1 h and then the protein purified on a CM-Poros column. ESI-MS data for the formaldehyde, acetaldehyde-, and butyraldehyde-treated forms of the protein indicated that their masses were 13 Da, 27 Da, and 54 Da higher, respectively, than the unmodified protein (Table 9).

TABLE 8

Expected and observed masses of human Sonic hedgehog treated with formaldehyde, acetaldehyde, and butyraldehyde.

| Protein | Expected mass*($MH^+$) | Observed mass*($MH^+$) |
|---|---|---|
| Unmodified | 19560.02 | 19560 |
| Formaldehyde-treated | 19572.03 | 19573 |
| Acetaldehyde-treated | 19586.06 | 19587 |
| Butyraldehyde-treated | 19614.11 | 19614 |

*Average masses were used in calculating the expected masses

For the formaldehyde-treated protein, peptide mapping, as described above, demonstrated that the site of the modification occurred in the peptide spanning the first 9 N-terminal residues, and that the exact mass increase was 12 Da. The results of MALDI-PSD MS studies of this peptide indicated that the modification occurred on Cys-1, and could be explained by a modification of the N-terminal α-amine and the thiol side chain of Cys-1 to form a thiaproline (See FIG. 12). The structure of the thiaproline was confirmed by automated N-terminal Edman sequencing using "on-line" prepared PTH-thiaproline as a standard. For the acetaldehyde- and butyraldehyde-treated proteins, the ESI-MS data were consistent with the modifications occuring by means of the same chemistry as for the reaction with formaldehyde, although the exact site of modification has not been established. When tested in the C3H10T1/2 cell-based assay, the formaldehyde-, acetaldehyde-, and butyraldehyde-modified proteins were approximately 8-fold, 2-fold, and 3-fold, respectively, more potent than unmodified Shh.

Modification of human Sonic hedgehog with N-isopropyliodoacetamide. This example shows that modification of human Shh with a hydrophobic derivative of iodoacetamide can enhance the potency of the protein as compared to the unmodified Shh. Purified Shh (1 mg/mL in 5 mM $Na_2HPO_4$ pH 7.0, 150 mM NaCl, 0.1 mM DTT) was incubated with 1 mM N-isopropyliodoacetamide (NIPIA) at 4° C. for 18 h. DTT was then added to 10 mM final concentration and the sample was dialyzed extensively against 5 mM $Na_2HPO_4$ pH 5.5, 150 mM NaCl, 0.5 mM DTT. The sample was purified on SP Sepharose Fast Flow resin and dialyzed further against 5 mM $Na_2HPO_4$ pH 5.5, 150 mM NaCl, 0.5 mM DTT. ESI-MS data indicated complete conversion to a species with a mass of 19660, corresponding to the predicted mass value (19659) for the singly modified protein. Specific modification of the N-terminal cysteine was confirmed by peptide mapping of proteolytic fragments. When tested in the C3H10T1/2 cell-based assay, the NIPIA-modified human Shh was approximately 2-fold more potent than the unmodified protein. While the modification of the protein resulted in only a modest increase in potency, it is expected that modification of the protein with long chain alkyl iodoacetamide derivatives will result in hydrophobically-modified forms of the protein with much greater increases in potency, possibly akin to the 100–200-fold increase observed for the palmitoylated, myristoylated, and lauroylated Shh proteins (See Example 8).

Modification of human Sonic hedgehog with 1-bromo-2-butanone to form a six-membered hydrophobic ring at the N-terminus. A thiomorpholinyl-(tetrahydrothiazinyl-) derivative of Shh was prepared by incubating human Shh-N (3 mg/mL in 5 mM $Na_2HPO_4$ pH 5.5, 150 mM NaCl, 0.15 mM DTT) with 11 mM 1-bromo-2-butanone at room temperature for 60 min, followed by reduction with 5 mM $NaCNBH_3$ at room temperature for 60 min. The reaction product was purified on a CM-Poros column (Perseptive Biosystems) as described below and was dialyzed against 5 mM $Na_2HPO_4$ pH 5.5, 150 mM NaCl, 0.5 mM DTT. ESI-MS and proteolytic peptide mapping data indicated that the product was a mixture of the expected thiomorpholinyl derivative (calculated mass=19615, observed mass=19615) and two forms of the protein both with 16 additional mass units. One of these forms is presumably the uncyclized keto-thioether intermediate. The mixture was tested in the C3H10T1/2 assay which indicated that it was approximately 5-fold more potent than the unmodified protein.

EXAMPLE 10

Genetically Engineered Mutations of Human Sonic Hedgehog A. Genetically Engineered Mutations of the N-terminal Cysteine In this example, we show that specific replacement of the N-terminal cysteine of human Sonic hedgehog (Cys-1) by single and multiple hydrophobic amino acid residues results in increased potency as compared to the wild type protein in the C3H10T1/2 cell-based assay described in Example 3.

Construction of Shh Cys-1 mutants. The 584 bp NcoI-XhoI restriction fragment carrying the His-tagged wild type Shh N-terminal fragment from p6H-SHH was subcloned into the pUC-derived cloning vector pNN05 to construct the plasmid pEAG649. Cys-1 mutants of soluble human Shh were made by unique site elimination mutagenesis of the pEAG649 plasmid template using a Pharmacia kit following the manufacturer's recommended protocol. In designing the mutagenic primers, if a desired mutation did not produce a restriction site change, a silent mutation producing a restriction site change was introduced into an adjacent codon to facilitate identification of mutant clones following mutagenesis. To avoid aberrant codon usage, substituted codons were selected from those occurring at least once elsewhere in the human Shh cDNA sequence. The following mutagenic primers were used: (1) for C1F: 5' GGC GAT GAC GAT GAC AAA TTC GGA CCG GGC AGG GGG TTC 3' (SEQ ID NO: 5), which introduces an ApoI site to make pEAG837; (2) for C1I: 5' GGC GAT GAC GAT GAC AAA ATA GGA CCG GGC AGG GGG TTC 3' (SEQ ID NO: 6), which loses an RsrII site to make pEAG838; and (3) for C1M: 5' GGC GAT GAC GAT GAC AAA ATG GGC CCG GGC AGG GGG TTC GGG 3' (SEQ ID NO: 7), which loses both RsrII and AvaII sites to make pEAG839. Mutations were confirmed by DNA sequencing through a 180 bp NcoI-BglII restriction fragment carrying the mutant SHH proteins' N-termini in plasmids pEAG837–839. Expression vectors were constructed by subcloning each mutant plasmid's 180 bp NcoI-BglII fragment and the 404 bp BglII-XhoI fragment from pEAG649 into the phosphatase-treated 5.64 kb XhoI- NcoI pET11d vector backbone of p6H-SHH. Presence of the introduced restriction site change was reconfirmed in the expression vector for each Cys-1 mutant (C1F in pEAG840, C1I in pEAG841, and C1M in pEAG842). Expression vectors were transformed into competent *E. coli* BL21 (DE3)pLysS (Stratagene) following the manufacturer's recommended protocol and selected on LB agar plates containing 100 µg/ml ampicillin and 30 µg/mL chloramphenicol. Individual colonies were selected and transformed bacteria were grown to an $A_{600}$ of 0.4–0.6 and induced for 3 h with 0.5 mM IPTG. Bacterial pellets were analyzed for expression of the mutant proteins by reducing SDS-PAGE and by Western blotting.

A soluble human Shh mutant with multiple N-terminal hydrophobic substitutions (C1II) was made by unique site elimination mutagenesis using a Pharmacia kit following the manufacturer's recommended protocol. In designing the mutagenic primers, if a desired mutation did not produce a restriction site change, a silent mutation producing a restriction site change was introduced into an adjacent codon to facilitate identification of mutant clones following mutagenesis. To avoid aberrant codon usage, substituted codons were selected from those occurring at least once elsewhere in the human Shh cDNA sequence. The following mutagenic primer was used on the C1F template plasmid pEAG837 for C1II: 5' GCG GCG ATG ACG ATG ACA AAA TCA TCG GAC CGG GCA GGG GGT TCG GG 3' (SEQ ID NO: 8), which removes an ApoI site to make pEAG872. Mutations were confirmed by DNA sequencing through a 0.59 kb NcoI-XhoI restriction fragment carrying the mutant C1II Shh. An expression vector was constructed by subcloning the mutant plasmid's NcoI-XhoI fragment into the phosphatase-treated 5.64 kb XhoI-NcoI pET11d vector backbone of p6H-SHH. Presence of the introduced restriction site change was reconfirmed in the expression vector for the C1II mutant, pEAG875. The expression vector was transformed into competent *E. coli* BL21(DE3)pLysS (Stratagene) following the manufacturer's recommended protocol and selected on LB agar plates containing 100 µg/mL ampicillin and 30 µg/mL chloramphenicol. Individual colonies were selected and transformed bacteria were grown to an $A_{600}$ of 0.4–0.6 and induced for 3 h with 0.5 mM IPTG. Bacterial pellets were analyzed as described above to confirm expression of mutant Shh protein.

Purification of Cys-1 mutants of human Sonic hedgehog. The His-tagged mutant hedgehog proteins were purified from the bacterial pellets as described for the wild type protein above except for two modifications. (1) The Phenyl Sepharose step was eliminated and instead the protein pool from the first NTA-Ni agarose column was dialyzed into 25 mM $Na_2HPO_4$ pH 8, 400 mM NaCl, 0.5 mM DTT in preparation for the enterokinase cleavage step. (2) The final ion exchange step was changed from step elution on SP-Sepharose Fast Flow to gradient elution from a CM-Poros column (Perseptive Biosystems). This was carried out in 50 mM $Na_2HPO_4$ pH 6.0 with a 0–800 mM NaCl gradient over 30 column volumes. The pooled peak fractions from this step were dialyzed into 5 mM $Na_2HPO_4$ pH 5.5, 150 mM NaCl and were stored at –80° C. Mass spectrometry of the purified proteins gave the predicted mass ions for each purified form.

Activity of the Cys-1 mutants of human Sonic hedgehog. As shown in Table 9 mutation of the N-terminal cysteine has a significant effect on the potency of the resulting hedgehog protein in the C3H10T1/2 assay. For single changes, potency generally correlates with the hydrophobicity of the substituted amino acid, that is phenylalanine and isoleucine give the greatest activation, methionine is less activating, while histidine and aspartic acid diminish activity compared to the wild type cysteine. Replacing the cysteine with two isoleucines gives an additional increase in activity over the single isoleucine substitution. Given that nine amino acids are categorized as more hydrophobic than cysteine (*Proteins: structures and molecular properties*, $2^{nd}$ ed, 1993, T. E. Creighton, W. H. Freeman Co. page 154), the substitutions tested above are clearly not an exhaustive survey of the possible mutations at the N-terminus that can give rise to more active forms of hedgehog. However, the results demonstrate that activation is not restricted to a single amino acid structure and that substitution of more than one amino acid can give a further increase in potency. Therefore, one skilled in the art could create forms of hedgehog with other amino acid substitutions at the N-terminus that would be expected to have greater potency than the wild type protein.

TABLE 9

Relative potency of amino acid modifications of human Sonic hedgehog in the C3H10T1/2 assay.

| N-TERMINUS | RELATIVE POTENCY |
|---|---|
| C (wild type) | 1X |
| M | 2X |
| F | 4X |
| I | 4X |
| II | 10X |

B. Genetically Engineered Mutations of Internal Residues

Construction of the C1II/A169C mutant. The soluble human Shh mutant C1II/A169C (with cysteine substituted for the dispensable C-terminal residue A169 which is predicted to have a high fractional solvent accessibility) was made by unique site elimination mutagenesis using a Pharmacia kit following the manufacturer's recommended protocol and employing the mutagenic oligo design principals described above. The following mutagenic primer 5' GAG TCA TCA GCC TCC CG TTT TGC GCA CAC CGA GTT CTC TGC TTT CAC C 3' (SEQ ID NO: 9) was used on C1II Shh template pEAG872 to add an FspI site to make pSYS049. The C1II/A169C mutations were confirmed by DNA sequencing through a 0.59 kb NcoI-XhoI restriction fragment. The expression vector pSYS050 was constructed by subcloning the NcoI-XhoI fragment into the phosphatase-treated 5.64 kb XhoI-NcoI pET11d vector backbone of p6H-SHH. Presence of the introduced restriction site change was reconfirmed in the expression vector. The expression vector was transformed into competent *E. coli* BL21 (DE3) pLysS, colonies were selected, induced, and screened for Shh expression as described above.

Purification of the C1II/A169C mutant. The C1II/A169C mutant was purified as described in Example 9 for wild type Shh except with the following modifications. (1) EDTA was left out of the lysis buffer, (2) the order of the NTA-Ni and SP Sepharose steps were switched and the Phenyl Sepharose step was omitted, (3) after clarification of the lysed bacteria by centrifugation, additional NaCl was added to the supernatant to a final concentration of 300 mM, (4) the elution buffer from the NTA-Ni column contained 25 mM $Na_2HPO_4$ pH 8.0, 200 mM imidazole, 400 mM NaCl, (5) the elution pool from the NTA-Ni column was diluted with 3 volumes of 100 mM MES pH 5.0 prior to loading onto the SP Sepharose column, (6) prior to addition of enterokinase, the SP Sepharose elution pool was diluted with half a volume of 50 mM $Na_2HPO_4$ pH 8.0, and (7) the DTT in the elution buffer from the final SP Sepharose column contained 0.2 mM DTT and the elution pool from this step was aliquoted and stored at −70° C.

Hydrophobic modification and activity of the C1II/A169C mutant. For modification with N-(1-pyrene) maleimide (Sigma), purified C1II/A169C at 4.6 mg/mL in 5 mM $Na_2HPO_4$ pH 5.5, 800 mM NaCl, 0.2 mM DTT was diluted with an equal volume of 50 mM MES pH 6.5 and to this a twentieth of a volume of pyrene maleimide from a 2.5 mg/mL stock in DMSO was added. The sample was incubated for 1 h at room temperature in the dark. At this time additional DTT was added to 0.5 mM and the sample incubated further for an additional hour at room temperature. The modified protein was tested directly for activity in the C3H10T1/2 assay as described in Example 3. Prior to modification, the specific activity of the protein was $EC_{50}$= 0.22 µg/mL, while after treatment with pyrene maleimide the specific activity was increased to $EC_{50}$=0.08 µg/mL. Increases in the specific activity of the modified product by up to 3-fold were observed frequently indicating that the addition of the hydrophobic group near the C-terminus of Shh resulted in a further increase in activity as compared to the C1II starting material. When compared to the wild type unmodified Sonic hedgehog protein, the N-(1-pyrene) maleimide-modified C1II protein was approximately 30-fold more potent. While pyrene maleimide provided a simple test system for evaluating modification at this site, other hydrophic maleimides or other cysteine targeted chemistries can also be used.

EXAMPLE 11

Comparison of the Potency of Various Hydrophobically-Modified Forms of Human Sonic Hedgehog in the C3H10T1/2 Assay The activity of various hydrophobically-modified forms of human Sonic hedgehog (prepared using the chemistries and genetic engineeering methods described in Section V) was tested in the C3H10T1/2 assay as described in Example 3.

Figure 13:
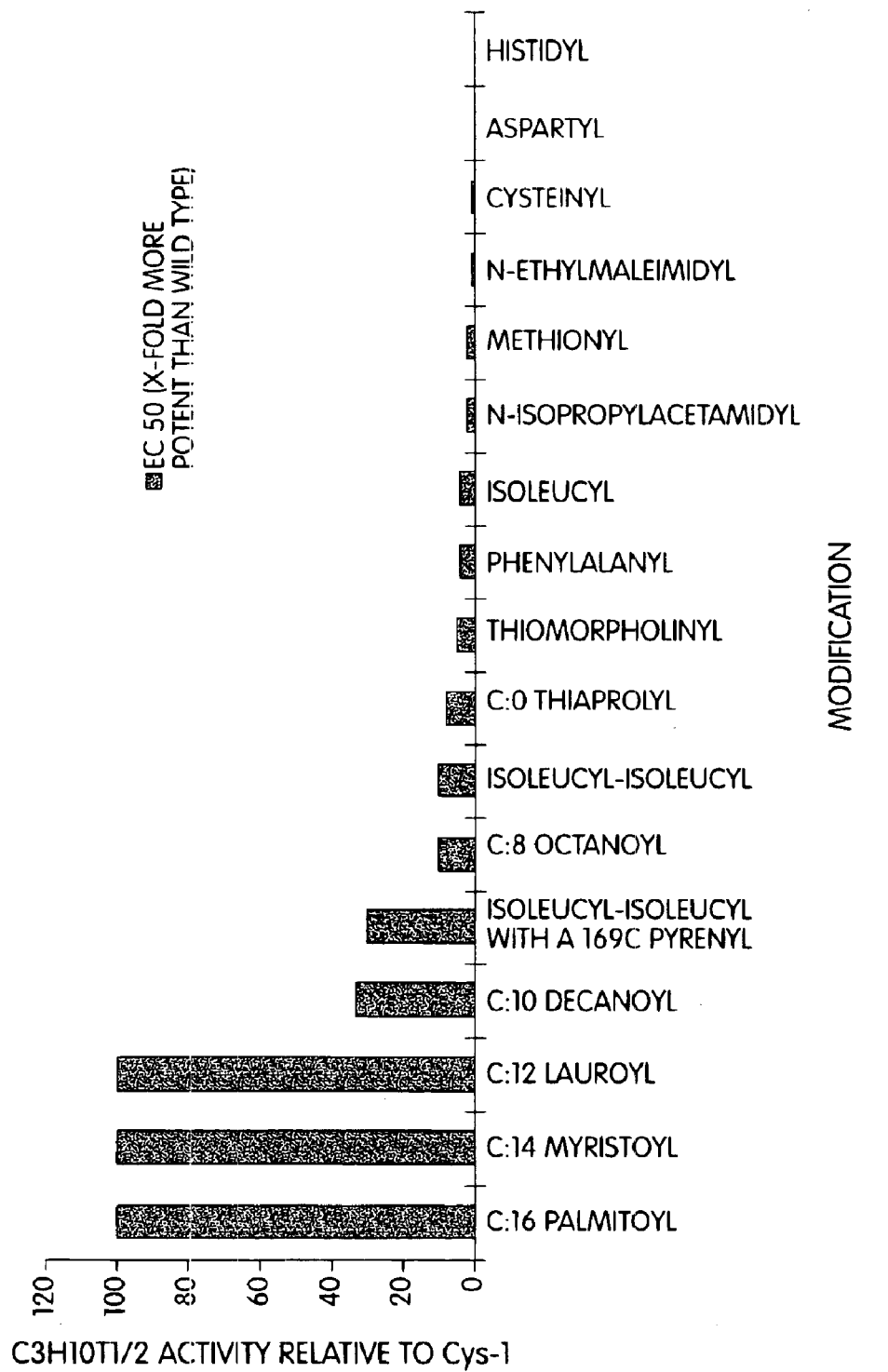
FIG. 13. Relative potency of various hydrophobically-modified forms of hedgehog in the C3H10T1/2 assay. The $EC_{50}$ (2 μg/ml) of unmodified wild type human Sonic hedgehog is designated as 1×. The potency of the other proteins is expressed as the ratio of the $EC_{50}$ of wild type protein divided by the $EC_{50}$ of the modified protein. Modifications are at the N-terminus of the protein unless designated otherwise.

The derivatives were assayed over a concentration range as described in Example 3. The concentration of hedgehog derivative that resulted in 50% of the maximum response in the assay was compared to the wild type concentration. The relative activities are shown in Table 10, below, and in FIG. 13.

TABLE 10

Relative Potency of Hedgehog Derivatives in the C3H10T1/2 assay.

| Modification | $EC_{50}$(x-fold more potent than wild type Shh) |
|---|---|
| C:16 palmitoyl | 100 |
| C:14 myristoyl | 100 |
| C:12 lauroyl | 100 |
| C:10 decanoyl | 33 |
| Isoleucyl-isoleucyl with A169C pyrenyl | 30 |
| C:8 octanoyl | 10 |
| Isoleucyl-isoleucyl | 10 |
| C:0 thiaprolyl | 8 |
| Thiomorpholinyl | 5 |
| Phenylalanyl | 4 |
| Isoleucyl | 4 |
| N-isopropylacetamidyl | 2 |
| Methionyl | 2 |
| N-ethylmaleimidyl | 1 |
| Cysteinyl (wild type) | 1 |
| Aspartyl | <1 |
| Histidyl | <1 |

The C3H10T1/2 assay demonstrates that a wide variety of hydrophobic modifications to hedgehog increase the protein's activity when compared to the wild type, unmodified protein. Hydrophilic modifications (aspartic acid and histidine) do not have this effect.

EXAMPLE 12

Evaluating the Efficacy of Hydrophobically-Modified Human Sonic Hedgehog in a Rat Malonate-Induced Striatal Lesion Assay Injection of malonate, an inhibitor of the mitochondrial enzyme succinate dehydrogenase, into the rat striatum (the rodent equivalent of the primate caudate and putamen) causes degeneration of striatal medium spiny neurons. In humans, degeneration of medium spiny neurons in the caudate and putamen is the primary pathological feature of Huntington's disease. Thus, the malonate-induced striatal lesion in rats can be used as a model to test whether hydrophobically-modified hedgehog proteins can prevent the death of the neurons which degenerate in Huntington's disease.

Sprague-Dawley rats were injected with various concentrations of hydrophobically-modified human Sonic hedgehog in the striatum using stereotaxic techniques. Stereotaxic injections (2 µL) were performed under sodium pentobarbital anesthesia (40 mg/kg) and placed at the following coordinates: 0.7 mm anterior to bregma, 2.8 mm lateral to the midline, and 5.5 mm ventral to the surface of the skull at bregma. At various times (usually 48 h) after injection of the hydrophobically-modified protein, rats were anesthetized with isoflurane and given a stereotaxic injection of malonate (2 µmol in 2 µL) at the same coordinates in the striatum. Four days after malonate injection, rats were sacrificed and their brains removed for histological analysis. Coronal sections were cut through the striatum at a thickness of 25 µm and stained for cytochrome oxidase activity to distinguish lesioned from unlesioned tissue. The volume of the lesion in the striatum is measured using an image analysis system.

Figure 14:
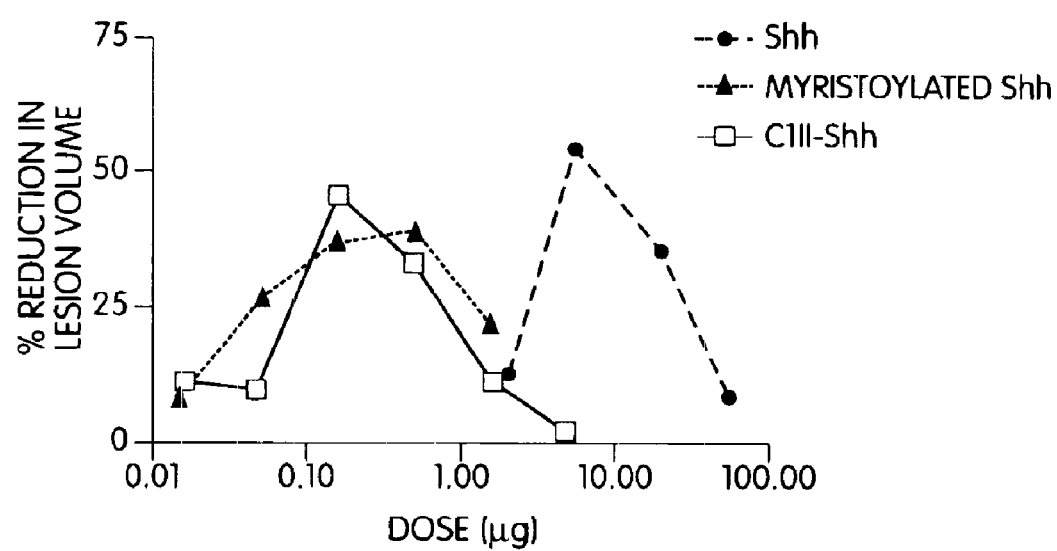
FIG. 14. Relative potency of the unmodified, myristoylated, and C1II mutant of human Sonic hedgehog in a malonate-induced rat striatal lesion assay. The figure shows the reduction in malonate-induced lesion volume which results from the administration of either unmodified, myristoylated, or the C1II mutant of human Sonic hedgehog to the rat striatum.
Figure 15:
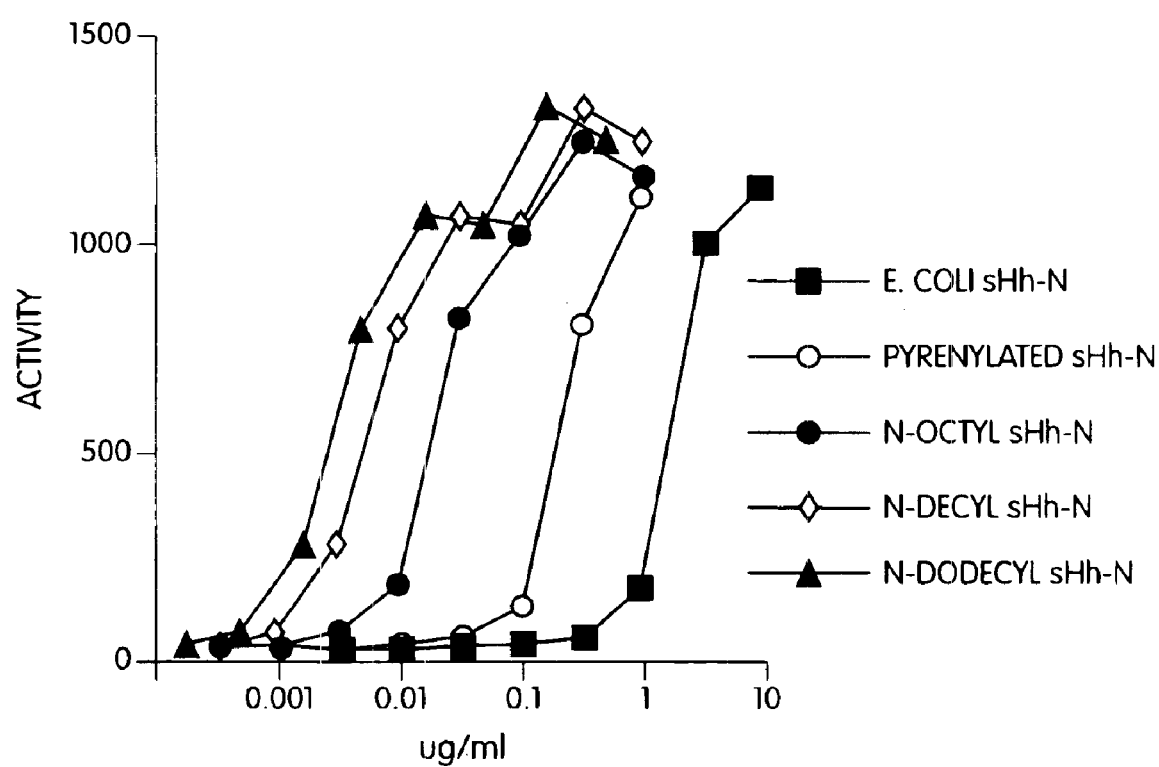
FIG. 15. illustrates the specific activities of maleimide modified and unmodified hedgehog polypeptides.

The effect of hydrophobically-modified human Sonic hedgehog protein in the malonate-induced rat striatal lesion model is shown in FIG. 14. Unmodified Sonic hedgehog (prepared as described in Example 9), myristoylated Shh (prepared as described in Example 8), and the C1II mutant of Shh (prepared as described in Example 10) all reduced lesion volume to a similar extent in this model. However, the hydrophobically-modified proteins (myristoylated Shh and C1II Shh) showed an increase in potency relative to the unmodified Sonic hedgehog.

EXAMPLE 13

N-Octylmaleimide Derivitization of sHh-N

For a 1 mg/ml Final Concentration

1) Make a 20 mM solution of octylmaleimide (m.w.=209) in DMSO (~4.2 mg/ml).

2) Dilute stock of 10 mg/ml sHh-N (in 5 mM NaPO4 pH 5.5, 150 mM NaCl, 0.5 mM DTT) 10-fold with PBS (Gibco product # 20012-027, pH 7.2) to give a 1 mg/ml (or 50 µM) sHh-N solution. [NOTE: DTT, which competes with sHh-N for maleimide in the subsequent reaction, is also 50 µM in this solution.]

3) Immediately add 1/200 vol. of octylmaleimide to the 1 mg/ml sHh-N (i.e. 5 µl/1 ml). This gives a 2:1 molar ratio (100 µM:50 µM) of octylmaleimide to sHh-N.

4) Mix this solution by gentle inversion of the tube and incubate for 1 hour at room temperature.

5) Finally, 1/1000 vol. of 0.35 M DTT was added to each tube to scavenge any remaining octylmaleimide and to serve as a reductant.

6) For a vehicle control, combine a solution of vehicle (5 mM NaPO4 pH 5.5, 150 mM NaCl, 0.5 mM DTT) with PBS (Gibco product # 20012-027, pH 7.2) in a 1:10 ratio. Add 1/400 vol. of 20 mM octylmaleimide in DMSO and a 1/400 vol. of DMSO to give a final concentration of 50 $\mu$M N-octylmaleimide and 0.5% DMSO. Finally, add 1:1000 vol. of 0.35 M DTT.

Approximate Composition of the 1 mg/ml N-octylmaleimide sHh-N Solution
PBS (~pH 7.2)
50 $\mu$M sHh-N conjugated to N-octylmaleimide
50 $\mu$M DTT conjugated to N-octylmaleimide
350 $\mu$M DTT
0.5% DMSO Approximate Composition of the N-octylmaleimide Vehicle Solution
PBS (~pH 7.2)
50 $\mu$M DTT conjugated to N-octylmaleimide
350 $\mu$M DTT
0.5% DMSO For a 3 m/ml Final Concentration 1) Make a 60 mM solution of octylmaleimide (m.w.=209) in DMSO (~12.6 mg/ml).

2) Dilute stock of 10 mg/ml sHh-N (in 5 mM NaPO4 pH 5.5, 150 mM NaCl, 0.5 mM DTT) 10-fold with PBS (Gibco product # 20012-027, pH 7.2) to give a 3 mg/ml (or 150 uM) sHh-N solution. [NOTE: DTT, which competes with sHh-N for maleimide in the subsequent reaction, is also 150 $\mu$M in this solution.]

3) Immediately add 1/200 vol. of octylmaleimide to the 3 mg/ml sHh-N (i.e. 5 $\mu$l/1 ml). This gives a 2:1 molar ratio (300 $\mu$M:150 $\mu$M) of octylmaleimide to sHh-N.

4) Mix this solution by gentle inversion of the tube and incubate for 1 hour at room temperature.

5) Finally, add 1/1000 vol. of 0.35 M DTT to each tube to scavenge any remaining octylmaleimide and to serve as a reductant.

6) For a vehicle control, combine a solution of vehicle (5 mM NaPO4 pH 5.5, 150 mM NaCl, 0.5 mM DTT) with PBS (Gibco product # 20012-027, pH 7.2) in a 3:7 ratio. Add 1/400 vol. of 60 mM octylmaleimide in DMSO and a 1/400 vol. of DMSO to give a final concentration of 150 $\mu$M N-octylmaleimide and 0.5% DMSO. Finally, add 1:1000 vol. of 0.5 M DTT.

Approximate Composition of the 3 mg/ml N-octylmaleimide sHh-N Solution
PBS (~pH 7.2)
150 $\mu$M sHh-N conjugated to N-octylmaleimide
150 $\mu$M DTT conjugated to N-octylmaleimide
500 $\mu$M DTT
0.5% DMSO Approximate Composition of the N-octylmaleimide Vehicle Solution
PBS (~pH 7.2)
150 $\mu$M DTT conjugated to N-octylmaleimide
500 $\mu$M DTT
0.5% DMSO
0.5% DMSO

REFERENCES

1. Perrimon, N. (1995) *Cell* 80, 517–520
2. Johnson, R. L., and Tabin, C. (1995) *Cell* 81, 313–316
3. Riddle, R. D. et al. (1993) *Cell* 75, 1401–1416
4. Niswander, L., et al. (1994) *Nature* 371, 609–612
5. Laufter, E., et al. (1994) *Cell* 79, 993–1003
6. Roberts, D. J., et al. (1995) *Development* 121, 3163–3174
7. Chiang, C., et al. (1996) *Nature* 382, 407–413
8. Bellusci, S., et al. (1997) *Development* 124, 53–63
9. Marigo, V., et al. (1996) *Nature* 384, 176–179
10. Stone, D. M., et al. (1996) *Nature* 384, 129–134
11. Alcedo, J., et al. (1996) *Cell* 86, 221–232.
12. Dominguez, M., et al. (1996) *Science* 272, 1621–1625
13. Alexandre, C., et al. (1996) *Genes & Dev.* 10, 2003–2013
14. Therond, P. P., et al. (1996) *Proc. Natl. Acad. Sci. USA* 93, 4224–4228
15. Lee, J. J., et al. (1994) *Science* 266, 1528–1536
16. Bumcrot, D. A., et al. (1995), *Mol. Cell Biol.* 15, 2294–2303
17. Porter, J. A., et al. (1995) *Nature* 374, 363–366
18. Porter, J. A., et al. (1996) *Science* 274, 255–258
19. Porter, J. A., et al. (1995) *Cell* 86, 21–34
20. Marigo, V., et al. (1995) *Genomics* 28, 44–51
21. Sanicola, M., et al. (1997) *Proc. Natl. Acad Sci. USA* 94, 6238–6243.
22. Spengler, B., et al. (1992) *Rapid Commun. Mass Spectrom.* 6, 105–108.
23. Spengler, B., et al. (1992) *J. Phys. Chem.* 96, 9678–9684
24. Caron, J. M. (1997) *Mol. Biol. Cell* 8, 621–636
25. Kinto, N., et al. (1997) *FEBS Letts.* 404, 319–323
26. Ericson, J., et al. (1996) *Cell* 87, 661–673
27. Wen, D., et al., (1996) *Biochemistry* 30, 9700–9709
28. Bizzozero, O. A. (1996) *Meth. Enzymol.* 250, 361–382
29. Wedegaertner, P. B., et al. (1995) *J. Biol. Chem.* 270, 503–506
30. Grosenbach, D. W., et al. (1997) *J. Biol. Chem.* 272, 1956–1964
31. Pepinsky, R. B., et al. (1991) *J. Biol. Chem.* 266, 18244–18249
32. Tanaka Hall, T. M., et al. (1995) *Nature* 378, 212–216
33. Mohler and Vani, (1992) *Development* 115, 957–971
34. Hall et al., (1995) *Nature* 378, 212–216
35. Ekker et al., (1995) *Current Biology* 5, 944–955
36. Fan et al., (1995) *Cell* 81, 457–465
37. Chang et al., (1994) *Development* 120, 3339–3353
38. Echelard et al., (1993) *Cell* 75, 1414–1430
39. Ericson et al., (1995) *Cell* 81, 747–756
40. Zoeller et al., (1984) *Proc. Natl. Acad. Sci. USA,* 81, 5662–66
41. Kaufman and Sharp, (1982) *Mol. Cell. Biol.,* 2, 1304–1319
42. Leung et al., (1989) *Technique* 1, 11–15
43. Mayers et al., (1989) *Science* 229, 242
44. Harang, S. A., (1983) *Tetrahedron* 39, 3
45. Itakura et al., (1984) *Ann. Rev. Biochem.* 53, 323
46. Cunningham and Wells, (1989) *Science* 244, 1081–1085
47. Adelman et al., (1983) *DNA* 2, 183
48. Wells et al., (1985) *Gene* 34, 315
49. W. D. Huse et al., (1989) *Science* 246, 1275–1281
50. H. L. Yin and T. P. Stossel, (1979) *Nature* 281, 583–586
51. Lindley, (1956) *Nature* 178, 647
52. Gross and Witkip, (1961) *J. Am. Chem. Soc.* 83, 1510
53. D. M. Haverstick and M. Glaser, (1987) *Proc. Natl. Acad. Sci. USA* 64, 4475–4478
54. Szoka et al., (1980) *Ann. Rev. Biophys. Bioeng.* 9, 467–508
55. Ohsawa et al., (1984) *Chem. Pharm. Bull.* 32, 2442
56. Batzri et al., (1973) *Biochim. Biophys. Acta* 298, 1015–1019
57. Szoka et al., (1978) *Proc. Natl. Acad. Sci. USA* 75, 4191–4199
58. Pick, (1981) *Arch. Biochem. Biophys.* 212, 186–194
59. Kasahara et al., (1977) *J. Biol. Chem.* 251, 7384–7390
60. Racker et al., (1979) *Arch. Biochem. Biophys.* 198, 470–477

61. Papahadjopoulos et al., (1991) *Proc. Natl. Acad. Sci. USA* 88, 11460–11464
62. Chou, T. C. and Lipmann, F. (1952) *J. Biol. Chem.* 196, 89
63. Kaminski et al., (1993) *New Engl. J. Med.* 329, 459
64. Tomac et al., (1995) *Nature* 373, 335–339
65. Gash et al., (1996) *Nature* 380, 252–255
66. Hoffer et al., (1994) *Neuroscience Lett.* 182, 107–111
67. Duchen, L. W. and Strich, S. J., (1968), *J. Neurol. Neurosurg. Psychiatry* 31, 535–542
68. Kennel et al., (1996) *Neurobiology of Disease* 3, 137–147
69. Ripps et al., (1995) *Proc. Natl. Acad Sci, USA,* 92: 689–693
71. Nicholson, L. et al., (1995) *Neuroscience* 66, 507–521
72. Beal, M. F. et al., (1993) *J. Neuroscience* 13, 4181–4192
73. Davies, S. et al., (1997) *Cell* 90, 537–548
74. Hebr-Katz, R. (1993) *Int. Rev. Immunol.* 9, 237–285
75. Borg et al., (1990) *Brain Res.,* 518, 295–298
76. Apfel et al., (1991) *Ann. Neurol.,* 29, 87–90
77. Noren, C. J. et al., (1989) *Science* 244, 182–188
78. Thorson, J. S. et al., (1998) *Methods Mol. Biol.* 77, 43–73
79. Das, A. K. et al., (1997) *J. Biol. Chem.* 272, 11021–11025
80. Berthiaume, L. & Resh, M. D. (1995) *J. Biol. Chem.* 270, 22399–22405
81. Raju, R. V. et al., (1995) *Mol. Cell. Biochem.* 149–150, pp. 191–202
82. Duronio, R. J. et al., (1993) in Lipid Modification of Proteins, M. J. Schlesinger, ed.
83. Krutsch, H. C. & Inman, J. K. (1993) *Anal. Biochem.* 209, 109–116
84. Heitz, J. R. et al., (1968) *Arch. Biochem. Biophys.* 12, 627–636
85. Stefanini, S. et al., (1972) *Arch. Biochem. Biophys* 151, 28–34
86. Kawaguchi, A. J. (1981) *Biochem.* (Tokyo) 89, 337–339
87. House, H. O. (1972) in Modern Synthetic Reactions, W. A. Benjamin, ed.

All of the above-cited references and publications are hereby incorporated by reference.

Equivalents

While we have described a number of embodiments of this invention, it is apparent to persons having ordinary skill in the art that our basic embodiments may be altered to provide other embodiments that utilize the compositions and processes of this invention. Therefore, it will be appreciated that the scope of this invention includes all alternative embodiments and variations which are defined in the foregoing specification and by the claims appended hereto; and the invention is not to be limited by the specific embodiments presented in the examples.

---

What is claimed is:

1. An isolated protein comprising an N-terminal amino acid and a C-terminal amino acid, wherein the protein comprises an amino acid sequence selected from:
   (a) an amino acid sequence with an N-terminal cysteine that is appended with at least one hydrophobic moiety;
   (b) an amino acid sequence with an N-terminal amino acid that is not a cysteine appended with at least one hydrophobic moiety; and
   (c) an amino acid sequence with at least one hydrophobic moiety substituted for the N-terminal amino acid;
   wherein the protein comprises an amino acid sequence at least 80% identical to any of SEQ ID NOs: 1–4 and binds patched, and wherein said hydrophobic moiety enhances a biological activity of the protein.

2. The protein of claim 1, wherein the hydrophobic moiety is a peptide comprising at least one hydrophobic amino acid.

3. The protein of claim 1, wherein the hydrophobic moiety is a lipid.

4. The protein of claim 3, wherein the lipid moiety is a fatty acid selected from saturated and unsaturated fatty acids having between 2 and 24 carbon atoms.

5. The protein of claim 1, wherein the protein further comprises a hydrophobic moiety substituted for, or appended to, the C-terminal amino acid.

6. The protein of claim 1, wherein the protein is an extracellular signaling protein.

7. The protein of claim 1, wherein the N-terminal amino acid is a functional derivative of a cysteine.

8. The protein of claim 1, wherein the protein is modified at both the N-terminal amino acid and the C-terminal amino acid.

9. The protein of claim 5 or 8, wherein the protein has a hydrophobic moiety substituted for, or appended to, at least one internal amino acid.

10. The protein of claim 1, wherein the protein has a hydrophobic moiety substituted for, or appended to, at least one amino acid intermediate to the N-terminal and C-terminal amino acids.

11. The protein of claim 1, further comprising a vesicle in contact with the hydrophobic moiety.

12. The protein of claim 11, wherein the vesicle is selected from a cell membrane, a micelle, and a liposome.

13. The protein of claim 1, wherein said protein binds patched and comprises an amino acid sequence at least 90% identical to any of SEQ ID NOs: 1–4.

14. An isolated protein having a C-terminal amino acid and an N-terminal thioproline group, said group formed by reacting an aldehyde with an N-terminal cysteine of the protein, wherein said protein comprises an amino acid sequence at least 80% identical to any of SEQ ID NOs: 1–4 and binds patched.

15. An isolated protein having a C-terminal amino acid and an N-terminal amide group, said group formed by reacting a fatty acid thioester with an N-terminal cysteine of the protein, wherein said protein comprises an amino acid sequence at least 80% identical to any of SEQ ID NOs: 1–4 and binds patched.

16. An isolated protein having a C-terminal amino acid and an N-terminal maleimide group, said N-terminal maleimide group formed by reacting a maleimide group with the N-terminal cysteine of the protein, wherein said protein comprises an amino acid sequence at least 80% identical to any of SEQ ID NOs: 1–4 and binds patched.

17. The isolated protein of claims 14, 15 or 16, wherein the C-terminal amino acid of the protein is modified with a hydrophobic moiety.

18. The protein of any of claims 14, 15 or 16, wherein said protein binds patched and comprises an amino acid sequence at least 90% identical to any of SEQ ID NOs: 1–4.

19. The protein of claim 18, wherein said protein comprises an amino acid sequence identical to any of SEQ ID NOs: 1–4.

20. A method for modifying a physico-chemical property of a protein, comprising introducing at least one hydrophobic moiety to an N-terminal cysteine of the protein or to a functional equivalent of the N-terminal cysteine, wherein said protein comprises an amino acid sequence at least 80% identical to any of SEQ ID NOs: 1–4 and binds patched.

21. The method of claim 20, further comprising contacting the hydrophobic moiety with a vesicle.

22. The method of claim 21, wherein the step of contacting comprises contacting with a vesicle selected from a cell membrane, liposome and micelle.

23. The method of claim 20, wherein the hydrophobic moiety is either a lipid moiety selected from saturated and an unsaturated fatty acids having between 2 and 24 carbon atoms or is a hydrophobic protein.

24. A modified protein, produced by the method of claim 20.

25. The method of claim 20, wherein said protein binds patched and comprises an amino acid sequence at least 90% identical to any of SEQ ID NOs: 1–4.

26. A method for modifying a protein having a biological activity and containing an N-terminal cysteine, comprising reacting the N-terminal cysteine with a fatty acid thioester to form an amide, wherein such modification enhances the protein's biological activity, wherein said protein comprises an amino acid sequence at least 80% identical to any of SEQ ID NOs: 1–4 and binds patched.

27. A method for modifying a protein having a biological activity and containing an N-terminal cysteine, comprising reacting the N-terminal cysteine with a maleimide group, wherein such modification enhances the protein's biological activity, wherein said protein comprises an amino acid sequence at least 80% identical to any of SEQ ID NOs: 1–4 and binds patched.

28. A method for modifying a protein that binds to an extracellular receptor, comprising appending a hydrophobic peptide to the protein, wherein the protein has a biological activity and the hydrophobic peptide enhances the biological activity, and wherein said protein comprises an amino acid sequence at least 80% identical to any of SEQ ID NOs: 1–4 and binds patched.

29. The method of claim 28, wherein the hydrophobic peptide is appended to an amino acid of the protein selected from the N-terminal amino acid, the C-terminal amino acid, an amino acid intermediate between the N-terminal amino acid, and the C-terminal amino acid, and combinations of the foregoing.

30. The method of claim 29, wherein the step of appending comprises replacing at least the N-terminal amino acid of the protein with at least one hydrophobic amino acid.

31. The method of claim 30, wherein the at least one hydrophobic amino acid is a plurality of isoleucine residues.

32. The method of claim 30, further comprising chemically modifying at least one of the isoleucine residues.

33. An isolated protein having a C-terminal amino acid and an N-terminal acetamide group, said group formed by reacting a substituted acetamide with an N-terminal cysteine of the protein, wherein said protein comprises an amino acid sequence at least 80% identical to any of SEQ ID NOs: 1–4 and binds patched.

34. An isolated protein having a C-terminal amino acid and an N-terminal thiomorpholine group, said group formed by reacting a haloketone group with an N-terminal cysteine of the protein, wherein said protein comprises an amino acid sequence at least 80% identical to any of SEQ ID NOs: 1–4 and binds patched.

35. A method for modifying a protein that binds to an extracellular domain of a cell membrane-associated receptor and contains an N-terminal cysteine, comprising reacting the N-terminal cysteine with a substituted acetamide group, wherein said protein has a biological activity, and the acetamide group enhances the biological activity of the protein, and wherein said protein comprises an amino acid sequence at least 80% identical to any of SEQ ID NOs: 1–4 and binds patched.

36. A method for modifying a protein having a biological activity and containing an N-terminal cysteine, comprising reacting the N-terminal cysteine with a haloketone group, wherein such modification enhances the protein's biological activity, wherein said protein comprises an amino acid sequence at least 80% identical to any of SEQ ID NOs: 1–4 and binds patched.

37. A method for modifying a protein that binds an extracellular domain of a cell membrane-associated receptor, comprising treating the protein with an active thioester under conditions sufficient to acylate the protein, wherein said protein has a biological activity, and acylation of the protein enhances the biological activity of the protein, and wherein said protein comprises an amino acid sequence at least 80% identical to any of SEQ ID NOs: 1–4 and binds patched.

38. The method of claim 37, wherein the protein is acylated at an amino acid selected from the N-terminal amino acid, the C-terminal amino acid, an amino acid intermediate between the N-terminal amino acid and the C-terminal amino acid, and combinations of the foregoing.

39. A method for modifying a protein that binds an extracellular domain of a cell membrane-associated receptor and contains an N-terminal cysteine, comprising reacting the N-terminal cysteine with a fatty acid active thioester to form an amide, wherein said protein has a biological activity, and the modification enhances the biological activity of the protein, and wherein said protein comprises an amino acid sequence at least 80% identical to any of SEQ ID NOs: 1–4 and binds patched.

40. An isolated polypeptide ligand for a receptor, which receptor includes an extracellular domain and which receptor is membrane-associated, wherein the ligand comprises an amino acid sequence at least 80% identical to any of SEQ ID NOs: 1–4 and binds patched, and wherein said ligand is covalently attached to a hydrophobic moiety that enhances the biological activity of the ligand relative to the biological activity of the ligand in the absence of the hydrophobic moiety.

41. The ligand of claim 40, wherein the hydrophobic moiety is a peptide comprising at least one hydrophobic amino acid.

42. The ligand of claim 40, wherein the hydrophobic moiety is a lipid.

43. The ligand of claim 42, wherein the lipid moiety is a fatty acid selected from saturated and unsaturated fatty acids having between 2 and 24 carbon atoms.

44. The ligand of claim 40, wherein the protein further comprises a hydrophobic moiety substituted for, or appended to, the C-terminal amino acid.

45. The ligand of claim 40, wherein the protein is an extracellular signaling protein.

46. The ligand of claim 40, wherein the N-terminal amino acid is a functional derivative of a cysteine.

47. The ligand of claim 40, wherein the ligand is modified at both the N-terminal amino acid and the C-terminal amino acid.

48. The ligand of claim 44 or 47, wherein the ligand has a hydrophobic moiety substituted for, or appended to, at least one internal amino acid.

49. The ligand of claim 40, wherein the ligand has a hydrophobic moiety substituted for, or appended to, at least one amino acid intermediate to the N-terminal and C-terminal amino acids.

50. The ligand of claim 40, further comprising a vesicle in contact with the hydrophobic moiety.

51. The ligand of claim 50, wherein the vesicle is selected from a cell membrane, a micelle, and a liposome.

* * * * *

SEQUENCE LISTING

```
<160> NUMBER OF SEQ ID NOS: 9

<210> SEQ ID NO 1
<211> LENGTH: 175
<212> TYPE: PRT
<213> ORGANISM: human

<400> SEQUENCE: 1

Cys Gly Pro Gly Arg Val Val Gly Ser Arg Arg Arg Pro Pro Arg Lys
 1               5                  10                  15

Leu Val Pro Leu Ala Tyr Lys Gln Phe Ser Pro Asn Val Pro Glu Lys
            20                  25                  30

Thr Leu Gly Ala Ser Gly Arg Tyr Glu Gly Lys Ile Ala Arg Ser Ser
        35                  40                  45

Glu Arg Phe Lys Glu Leu Thr Pro Asn Tyr Asn Pro Asp Ile Ile Phe
    50                  55                  60

Lys Asp Glu Glu Asn Thr Gly Ala Asp Arg Leu Met Thr Gln Arg Cys
65                  70                  75                  80

Lys Asp Arg Leu Asn Ser Leu Ala Ile Ser Val Met Asn Gln Trp Pro
                85                  90                  95

Gly Val Lys Leu Arg Val Thr Glu Gly Trp Asp Glu Asp Gly His His
            100                 105                 110

Ser Glu Glu Ser Leu His Tyr Glu Gly Arg Ala Val Asp Ile Thr Thr
        115                 120                 125

Ser Asp Arg Asp Arg Asn Lys Tyr Gly Leu Leu Ala Arg Leu Ala Val
    130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Ala Lys Thr Gly Gly
                165                 170                 175
```

<210> SEQ ID NO 2
<211> LENGTH: 174
<212> TYPE: PRT
<213> ORGANISM: human

<400> SEQUENCE: 2

Cys Gly Pro Gly Arg Gly Phe Gly Lys Arg Arg His Pro Lys Lys Leu
 1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Ser Arg Asn Ser Glu
         35                  40                  45

Arg Phe Lys Glu Leu Thr Pro Asn Tyr Asn Pro Asp Ile Ile Phe Lys
     50                  55                  60

Asp Glu Glu Asn Thr Gly Ala Asp Arg Leu Met Thr Gln Arg Cys Lys
 65                  70                  75                  80

Asp Lys Leu Asn Ala Leu Ala Ile Ser Val Met Asn Gln Trp Pro Gly
                 85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 3
<211> LENGTH: 176
<212> TYPE: PRT
<213> ORGANISM: human

<400> SEQUENCE: 3

Cys Gly Pro Gly Arg Gly Pro Val Gly Arg Arg Tyr Ala Arg Lys
 1               5                  10                  15

Gln Leu Val Pro Leu Leu Tyr Lys Gln Phe Val Pro Gly Val Pro Glu
             20                  25                  30

Arg Thr Leu Gly Ala Ser Gly Pro Ala Glu Gly Arg Val Ala Arg Gly
         35                  40                  45

Ser Glu Arg Phe Arg Asp Leu Val Pro Asn Tyr Asn Pro Asp Ile Ile
     50                  55                  60

Phe Lys Asp Glu Glu Asn Ser Gly Ala Asp Arg Leu Met Thr Glu Arg
 65                  70                  75                  80

Cys Lys Glu Arg Val Asn Ala Leu Ala Ile Ala Val Met Asn Met Trp
                 85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
        115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Val
145                 150                 155                 160

```
His Val Ser Val Lys Ala Asp Asn Ser Leu Ala Val Arg Ala Gly Gly
            165                 170                 175
```

```
<210> SEQ ID NO 4
<211> LENGTH: 176
<212> TYPE: PRT
<213> ORGANISM: human
<220> FEATURE:
<221> NAME/KEY: SITE
<222> LOCATION: (6)
<223> OTHER INFORMATION: Xaa= Val or Gly
<220> FEATURE:
<221> NAME/KEY: SITE
<222> LOCATION: (7)
<223> OTHER INFORMATION: Xaa= Val, Phe, or Pro
<220> FEATURE:
<221> NAME/KEY: SITE
<222> LOCATION: (8)
<223> OTHER INFORMATION: Xaa= Gly or Val
<220> FEATURE:
<221> NAME/KEY: SITE
<222> LOCATION: (9)
<223> OTHER INFORMATION: Xaa= Ser or Gly
<220> FEATURE:
<221> NAME/KEY: SITE
<222> LOCATION: (10)
<223> OTHER INFORMATION: Xaa= Arg or Lys
<220> FEATURE:
<221> NAME/KEY: SITE
<222> LOCATION: (13)
<223> OTHER INFORMATION: Xaa= Pro, His, or Tyr
<220> FEATURE:
<221> NAME/KEY: SITE
<222> LOCATION: (14)
<223> OTHER INFORMATION: Xaa= Pro or Ala
<220> FEATURE:
<221> NAME/KEY: SITE
<222> LOCATION: (15)
<223> OTHER INFORMATION: Xaa= Arg or Lys
<220> FEATURE:
<221> NAME/KEY: SITE
<222> LOCATION: (17)
<223> OTHER INFORMATION: Xaa= any amino acid
<220> FEATURE:
<221> NAME/KEY: SITE
<222> LOCATION: (19)
<223> OTHER INFORMATION: Xaa= Val or Thr
<220> FEATURE:
<221> NAME/KEY: SITE
<222> LOCATION: (22)
<223> OTHER INFORMATION: Xaa= Ala or Leu
<220> FEATURE:
<221> NAME/KEY: SITE
<222> LOCATION: (27)
<223> OTHER INFORMATION: Xaa= Ser, Ile, or Val
<220> FEATURE:
<221> NAME/KEY: SITE
<222> LOCATION: (29)
<223> OTHER INFORMATION: Xaa= Asn or Gly
<220> FEATURE:
<221> NAME/KEY: SITE
<222> LOCATION: (31)
<223> OTHER INFORMATION: Xaa= Pro or Ala
<220> FEATURE:
<221> NAME/KEY: SITE
<222> LOCATION: (41)
<223> OTHER INFORMATION: Xaa= Tyr or Ala
<220> FEATURE:
<221> NAME/KEY: SITE
<222> LOCATION: (45)
<223> OTHER INFORMATION: Xaa= Ile or Val
<220> FEATURE:
<221> NAME/KEY: SITE
<222> LOCATION: (46)
<223> OTHER INFORMATION: Xaa= Ala or Ser
<220> FEATURE:
<221> NAME/KEY: SITE
```

```
<222> LOCATION: (48)
<223> OTHER INFORMATION: Xaa= Ser, Asn, or Gly
<220> FEATURE:
<221> NAME/KEY: SITE
<222> LOCATION: (54)
<223> OTHER INFORMATION: Xaa= Glu or Asp
<220> FEATURE:
<221> NAME/KEY: SITE
<222> LOCATION: (56)
<223> OTHER INFORMATION: Xaa= Thr or Val
<220> FEATURE:
<221> NAME/KEY: SITE
<222> LOCATION: (71)
<223> OTHER INFORMATION: Xaa= Thr or Ser
<220> FEATURE:
<221> NAME/KEY: SITE
<222> LOCATION: (79)
<223> OTHER INFORMATION: Xaa= Gln or Glu
<220> FEATURE:
<221> NAME/KEY: SITE
<222> LOCATION: (83)
<223> OTHER INFORMATION: Xaa= Asp or Glu
<220> FEATURE:
<221> NAME/KEY: SITE
<222> LOCATION: (84)
<223> OTHER INFORMATION: Xaa= Arg or Lys
<220> FEATURE:
<221> NAME/KEY: SITE
<222> LOCATION: (85)
<223> OTHER INFORMATION: Xaa= Leu or Val
<220> FEATURE:
<221> NAME/KEY: SITE
<222> LOCATION: (91)
<223> OTHER INFORMATION: Xaa= Ser or Ala
<220> FEATURE:
<221> NAME/KEY: SITE
<222> LOCATION: (95)
<223> OTHER INFORMATION: Xaa= Gln or Met
<220> FEATURE:
<221> NAME/KEY: SITE
<222> LOCATION: (114)
<223> OTHER INFORMATION: Xaa= Ser or Ala
<220> FEATURE:
<221> NAME/KEY: SITE
<222> LOCATION: (115)
<223> OTHER INFORMATION: Xaa= Glu or Gln
<220> FEATURE:
<221> NAME/KEY: SITE
<222> LOCATION: (116)
<223> OTHER INFORMATION: Xaa= Glu or Asp
<220> FEATURE:
<221> NAME/KEY: SITE
<222> LOCATION: (135)
<223> OTHER INFORMATION: Xaa= Asn or Ser
<220> FEATURE:
<221> NAME/KEY: SITE
<222> LOCATION: (139)
<223> OTHER INFORMATION: Xaa= Leu or Met
<220> FEATURE:
<221> NAME/KEY: SITE
<222> LOCATION: (157)
<223> OTHER INFORMATION: Xaa= Lys or Arg
<220> FEATURE:
<221> NAME/KEY: SITE
<222> LOCATION: (158)
<223> OTHER INFORMATION: Xaa= Ala or Asn
<220> FEATURE:
<221> NAME/KEY: SITE
<222> LOCATION: (160)
<223> OTHER INFORMATION: Xaa= Val or Ile
<220> FEATURE:
<221> NAME/KEY: SITE
<222> LOCATION: (162)
<223> OTHER INFORMATION: Xaa= Cys or Val
<220> FEATURE:
<221> NAME/KEY: SITE
<222> LOCATION: (166)
<223> OTHER INFORMATION: Xaa= Ser or Ala
<220> FEATURE:
```

```
<221> NAME/KEY: SITE
<222> LOCATION: (167)
<223> OTHER INFORMATION: Xaa= Glu or Asp
<220> FEATURE:
<221> NAME/KEY: SITE
<222> LOCATION: (168)
<223> OTHER INFORMATION: Xaa=His or Asn
<220> FEATURE:
<221> NAME/KEY: SITE
<222> LOCATION: (170)
<223> OTHER INFORMATION: Xaa= Ala, Val, or Lys
<220> FEATURE:
<221> NAME/KEY: SITE
<222> LOCATION: (173)
<223> OTHER INFORMATION: Xaa= Lys or Arg
<220> FEATURE:
<221> NAME/KEY: SITE
<222> LOCATION: (174)
<223> OTHER INFORMATION: Xaa= Thr, Ser or Ala

<400> SEQUENCE: 4

Cys Gly Pro Gly Arg Xaa Xaa Xaa Xaa Xaa Arg Arg Xaa Xaa Xaa Lys
 1               5                  10                  15

Xaa Leu Xaa Pro Leu Xaa Tyr Lys Gln Phe Xaa Pro Xaa Val Xaa Glu
            20                  25                  30

Lys Thr Leu Gly Ala Ser Gly Arg Xaa Glu Gly Lys Xaa Xaa Arg Xaa
        35                  40                  45

Ser Glu Arg Phe Lys Xaa Leu Xaa Pro Asn Tyr Asn Pro Asp Ile Ile
    50                  55                  60

Phe Lys Asp Glu Glu Asn Xaa Gly Ala Asp Arg Leu Met Thr Xaa Arg
65                  70                  75                  80

Cys Lys Xaa Xaa Xaa Asn Ser Leu Ala Ile Xaa Val Met Asn Xaa Trp
                85                  90                  95

Pro Gly Val Lys Leu Arg Val Thr Glu Gly Trp Asp Glu Asp Gly His
            100                 105                 110

His Xaa Xaa Xaa Ser Leu His Tyr Glu Gly Arg Ala Val Asp Ile Thr
        115                 120                 125

Thr Ser Asp Arg Asp Arg Xaa Lys Tyr Gly Xaa Leu Ala Arg Leu Ala
130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa Xaa Ser Xaa Ala Ala Xaa Xaa Gly Gly
                165                 170                 175

<210> SEQ ID NO 5
<211> LENGTH: 39
<212> TYPE: DNA
<213> ORGANISM: Primer

<400> SEQUENCE: 5
ggcgatgacg atgacaaatt cggaccgggc aggggttc                    39

<210> SEQ ID NO 6
<211> LENGTH: 39
<212> TYPE: DNA
<213> ORGANISM: Primer

<400> SEQUENCE: 6
ggcgatgacg atgacaaaat aggaccgggc aggggttc                    39

<210> SEQ ID NO 7
<211> LENGTH: 42
<212> TYPE: DNA
```

-continued

```
<213> ORGANISM: Primer

<400> SEQUENCE: 7
ggcgatgacg atgacaaaat gggcccgggc aggggttcg gg                42

<210> SEQ ID NO 8
<211> LENGTH: 47
<212> TYPE: DNA
<213> ORGANISM: Primer

<400> SEQUENCE: 8
gcggcgatga cgatgacaaa atcatcggac cgggcagggg gttcggg          47

<210> SEQ ID NO 9
<211> LENGTH: 49
<212> TYPE: DNA
<213> ORGANISM: Primer

<400> SEQUENCE: 9
gagtcatcag cctcccgatt ttgcgcacac cgagttctct gctttcacc        49
```